(12) United States Patent
Perumal et al.

(10) Patent No.: US 9,220,680 B2
(45) Date of Patent: Dec. 29, 2015

(54) COMPOSITIONS AND METHODS FOR LOCALIZED DRUG DELIVERY THROUGH MAMMARY PAPILLAE

(71) Applicant: South Dakota State University, Brookings, SD (US)

(72) Inventors: Omathanu P Perumal, Brookings, SD (US); Kaushalkumar Dave, Brookings, SD (US); Chandradhar Dwivedi, Brookings, SD (US); Sreevidy Santha, Brookings, SD (US)

(73) Assignee: South Dakota State University, Brookings, SD (US)

( * ) Notice: Subject to any disclaimer, the term of this patent is extended or adjusted under 35 U.S.C. 154(b) by 0 days.

(21) Appl. No.: 13/942,686

(22) Filed: Jul. 15, 2013

(65) Prior Publication Data

US 2014/0088059 A1    Mar. 27, 2014

Related U.S. Application Data

(60) Provisional application No. 61/671,597, filed on Jul. 13, 2012.

(51) Int. Cl.
| | | |
|---|---|---|
| *A61K 31/56* | (2006.01) | |
| *C12N 5/02* | (2006.01) | |
| *A61K 9/00* | (2006.01) | |
| *A61K 9/107* | (2006.01) | |
| *A61K 31/138* | (2006.01) | |
| *A61K 31/513* | (2006.01) | |
| *A61K 31/565* | (2006.01) | |
| *A61K 47/10* | (2006.01) | |
| *A61K 31/282* | (2006.01) | |
| *A61K 31/337* | (2006.01) | |
| *A61K 31/57* | (2006.01) | |
| *A61K 31/58* | (2006.01) | |
| *A61K 31/675* | (2006.01) | |
| *A61K 31/7008* | (2006.01) | |

(52) U.S. Cl.
CPC ............ *A61K 9/0041* (2013.01); *A61K 9/1075* (2013.01); *A61K 31/138* (2013.01); *A61K 31/282* (2013.01); *A61K 31/337* (2013.01); *A61K 31/513* (2013.01); *A61K 31/565* (2013.01); *A61K 31/57* (2013.01); *A61K 31/58* (2013.01); *A61K 31/675* (2013.01); *A61K 31/7008* (2013.01); *A61K 47/10* (2013.01)

(58) Field of Classification Search
None
See application file for complete search history.

(56) References Cited

U.S. PATENT DOCUMENTS

| | | |
|---|---|---|
| 6,406,706 B1 | 6/2002 | Haque et al. |
| 8,431,555 B2 | 4/2013 | Schwartz et al. |
| 2008/0058413 A1 | 3/2008 | Singh et al. |
| 2009/0281063 A1 | 11/2009 | Inagi et al. |
| 2011/0212157 A1 | 9/2011 | Edelson et al. |
| 2013/0005830 A1* | 1/2013 | Clements et al. ............. 514/729 |

FOREIGN PATENT DOCUMENTS

| | | |
|---|---|---|
| CN | 101760314 A * | 6/2010 |
| WO | WO 2011/109411 A2 | 9/2011 |

OTHER PUBLICATIONS

Cameron et al. (Br. J. Cancer, 1994, 70, 120-124).*
Zhang (CN101760314A; published Jun. 30, 2010; English Abstract).*
Sterns et al., Sci Translational Medicine (2011) 3(106): 1-19.

* cited by examiner

*Primary Examiner* — Dennis Heyer
*Assistant Examiner* — Daniel M Podgorski

(57) ABSTRACT

The invention provides compositions and methods for the prevention, diagnosis, or treatment of conditions affecting breast tissue. The compositions can include one or more therapeutic agents or diagnostic agents, and an effective carrier. The composition can be specifically adapted for transdermal permeation through the mammary papilla, areola, or a combination thereof, and into underlying breast tissue.

10 Claims, 40 Drawing Sheets

Hydrophilic dye (SRB)

Hydrophobic dye (NR)

(Bar= 100 μm)

Effects of α-santalol on the distribution of MCF-7 cells

Total drug in the mammary papilla = 39.26 +/- 2.4 µmol/g tissue.

Medicated devices for physical permeation enhancement techniques

Medicated devices for nipple piercing

Medicated aerosols for spraying over nipple

Microneedle based drug delivery (drug loaded soluble microneedles or solid/hollow microneedles)

Drug application followed by application of heat

Drug depot formation by injecting thermo-reversible gel

Medicated pad, patch and nipple shield like medicated devices

COMPOSITIONS AND METHODS FOR LOCALIZED DRUG DELIVERY THROUGH MAMMARY PAPILLAE

CROSS REFERENCE TO RELATED APPLICATION

This application claims benefit under 35 U.S.C. §119(e) to U.S. Provisional Application No. 61/671,597, filed Jul. 13, 2012, which is incorporated by reference herein in its entirety.

BACKGROUND OF THE INVENTION

1. Field of the Invention

This present invention relates generally to chemotherapeutic treatments, and more specifically to treatment of conditions affecting breast tissue, including the disclosure of compositions which enhance permeation of agents through the mammary papilla and methods of using such compositions.

2. Background Information

Breast cancer is the second leading cause of cancer related deaths in women worldwide. One in eight women carries an increased risk of breast cancer. Ninety-five percent of breast cancer originates in the ducts and mammary glands of the breast. Breast cancer treatments include chemotherapy, radiation and tissue excision surgery. Traditional breast cancer therapy includes systemic chemotherapy that can be accompanied by severe side effects and potentially life threatening risks. Many current approaches are limited by their systemic side effects, thus warranting alternative approaches (Stearns et al., Sci. Transl. Med. 2011, 3, (106), 106-108).

Breast cancer is a cancer that occurs in mammary gland tissues. Breast cancer can be classified into lobular carcinoma arising from acinus and breast ductal carcinoma arising from breast ducts. The state of cancer limited within lobules or breast ducts and not disseminating to surrounding tissue is called non-infiltrating cancer. Cancer cells that proliferate in breast ducts, destroy basement membrane, and develop metastasis to the neighboring tissues are called infiltrating cancer cells. Adjuvant chemotherapy, where an anticancer agent is administered after surgery that excises affected parts, is a common treatment method for breast cancer. However, many systemically administered anticancer agents cause side effects such as nausea, loss of appetite, and alopecia when administered systemically.

Mastitis can be classified as stagnation mastitis or acute suppurative mastitis. Stagnation mastitis develops just after the puerperium where milk stagnates within breast ducts. Acute suppurative mastitis develops by infection of bacteria such as *staphylococcus*, *Escherichia coli*, and *streptococcus*. Acute suppurative mastitis is often treated systemically with anti-inflammatory analgesic agents; however the systemic agents can have a variety of negative side effects.

Accordingly, there is a need for compositions and methods to treat conditions of the breast by effectively and efficiently administering active agents to the breast tissue by means other than systemic administration. There is also a need for compositions and methods for treating conditions of the breast that can be effective, at lower doses and with significantly reduced side effects.

SUMMARY OF THE INVENTION

The mammary papilla (nipple) is a projection on the breast to deliver milk from mammary gland. It is a leaky structure connected to the ducts and thus to the lobules of the breast. The inventors have found that the mammary papilla can be used for the effective and efficient delivery of therapeutics for cancer and other conditions of the breast.

The nipple has openings (10-50 µm) that directly connects to glands and ducts, which can be the target site for effective chemotherapy. Such administration through the mammary papilla can result in high local drug concentrations, and therefore reduced doses. Reduced doses can reduce issues associated with toxicity. Additionally, the localized delivery itself can reduce side effects due to minimal system adverse effects. A lower incidence of side effects results in higher patient compliance. Low compliance is a significant issue for many current chemotherapeutic methods. Patient compliance and convenience is further increased by the ease of application and removal of the treatment compositions. The invention thus provides safe, localized delivery and improved efficacy compared other treatments.

This disclosure demonstrates the in vitro effectiveness of delivering drugs to the breast tissue through the mammary papilla. Examples of model actives include 5-fluorouracil (5FU; Log P=−0.89) and estradiol (EST: Log P=3.6), which generally model hydrophilic and lipophilic drug, respectively. The invention thus provides compositions and methods for drug delivery to the breast through the mammary papilla (nipple).

Accordingly, the invention provides compositions for the prevention, diagnosis, or treatment of a condition affecting breast tissue. The composition can include a therapeutic agent or a diagnostic agent, and an effective carrier, where the composition is adapted for transdermal permeation through the mammary papilla, areola, or a combination thereof, and into underlying breast tissue. The agent can be, for example, a chemopreventive agent, a diagnostic agent, or a chemotherapeutic agent. The agent can also be a hydrophilic agent, a lipophilic agent, or a macromolecular agent. In some embodiments, the agent is 5-fluorouracil, cyclophosphamide, tamoxifen, adriamycin, danazol, progesterone, doxorubicin, paclitaxel, cisplatin, docetaxel, or a diagnostic agent. In one specific embodiment, the agent is alpha-santalol.

The invention also provides a method of reducing the occurrence or severity of breast cancer or mastitis. The method can include administering an effective prophylactic amount of a composition described herein to the mammary papilla or areola, wherein the therapeutic agent permeates into the breast deeper than the mammary papilla or areola.

The invention further provides a method of diagnosing a condition of the breast comprising administering an effective diagnostic amount of a composition described herein to the mammary papilla or areola, wherein the diagnostic agent permeates into the breast deeper than the mammary papilla or areola, and at least part of the composition interacts with tissue affected by the condition of the breast, if present. The interaction of the diagnostic agent and tissue affected by the condition can then be identified, analyzed, located, or a combination thereof.

The invention yet further provides a method of treating breast cancer or mastitis comprising administering an effective therapeutic amount of a composition described herein to the mammary papilla or areola, wherein the therapeutic agent permeates into the breast deeper than the mammary papilla or areola, and the breast cancer is thereby treated. For example, the administering of the composition described herein can kill cancer cells in the breast or inhibit the grown or proliferation of cancer cells in the breast.

In some embodiments, the therapeutic or diagnostic agent is a hydrophilic agent. In other embodiments, the therapeutic or diagnostic agent is a lipophilic agent. In some embodiments, the therapeutic or diagnostic agent is a macromolecular agent.

The invention also provides for the use of the compositions described herein for use in medical therapy. The medical therapy can be treating cancer, for example, breast cancer. The invention also provides for the use of a composition described herein for the manufacture of a medicament useful for the treatment of a condition in a mammal, for example, cancer or an infection in a human. The medicament can include a pharmaceutically acceptable diluent, excipient, or carrier.

In embodiments, a composition for the prevention, diagnosis, or treatment of a condition affecting breast tissue is disclosed including an alcoholic component, a therapeutic agent or a diagnostic agent, and an effective carrier, the composition being adapted for transdermal permeation through the mammary papilla, areola, or a combination thereof, and into underlying breast tissue, wherein the carrier is an extract of sandalwood oil.

In one aspect, the agent is chemopreventive agent, a diagnostic agent, or a chemotherapeutic agent. In another aspect, the agent is a hydrophilic agent, a lipophilic agent, or a macromolecular agent.

In one aspect, the agent is 5-fluorouracil, cyclophosphamide, tamoxifen, adriamycin, danazol, progesterone, doxorubicin, paclitaxel, cisplatin, docetaxel, or a diagnostic agent.

In another aspect, the carrier is a α-santalol. In a further aspect, the composition is substantially a microemulsion, or alternatively, the composition is substantially a hydroalcoholic solution.

In one aspect, the composition comprises at least about 5% α-santalol (v/v). In a related aspect, the composition comprises between about 5% to about 25% α-santalol (v/v).

In another aspect, the therapeutic agent or a diagnostic agent has a molecular weight of between about 4000 to 60000 daltons or between about 10000 to 50000 daltons.

In another embodiments, a method of enhancing the permeation characteristics of lipophilic molecules across mammary papilla tissue is disclosed including combining one or more lipophilic molecules with a carrier, where the carrier is an extract of sandalwood oil to form a mixture; combining the mixture with a surfactant or an alcohol to form an emulsion or a solution; and applying the emulsion or solution to mammary papilla tissue, where the one or more lipophilic molecules in the emulsion or solution exhibit one or more of the following characteristics relative to one or more of the same lipophilic molecules in the absence of said emulsion or solution, where the characteristics include increased flux across said tissue, increased applied dose permeated across said tissue, greater retention of said one or more lipophilic molecules within said tissue, reduced lag time, and combinations thereof.

In a related aspect, the method further includes exposing the mammary papilla with a sufficient amount of alcohol to remove a keratin plug from the tissue prior to applying the emulsion or said solution. In another related aspect, the sandalwood extract is α-santalol.

In a further related aspect, the one or more lipophilic molecules include nitrosoureas, tamoxifens, camptothecins, lipophilic statins, retinoids, and daunomycin. In another related aspect, the enhancement method is carried out in vivo or in situ. In a further related aspect, the enhancement method is carried out in vitro.

In one embodiment, a composition is disclosed including α-santalol, an alcohol, optionally a surfactant, and a compound including 5-fluorouracil, cyclophosphamide, tamoxifen, adriamycin, danazol, progesterone, doxorubicin, paclitaxel, cisplatin, docetaxel, nitrosoureas, camptothecins, lipophilic statins, retinoids, and daunomycin.

In another embodiment, a method of treating a subject with breast cancer is disclosed including applying sufficient alcohol to the outer surface of mammary papillae tissue of the subject to remove the keratin plug therein; and (b) administering a composition as disclosed herein to the alcohol treated mammary papillae at a sufficient dose to produce a therapeutic effect.

In a related aspect, the surface is dry prior to the administering step. In another related aspect, the composition comprises α-santalol, an alcohol, a surfactant and a tamoxifen in the form of a microemulsion. In a further related aspect, the tamoxifen will exhibit one or more of the following characteristics relative to tamoxifen in the absence of the α-santalol, where the characteristics include increased flux across said tissue, increased applied dose permeated across said tissue, greater retention of said tamoxifen within said tissue, reduced lag time, and combinations thereof.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION OF THE INVENTION

Figure 1:
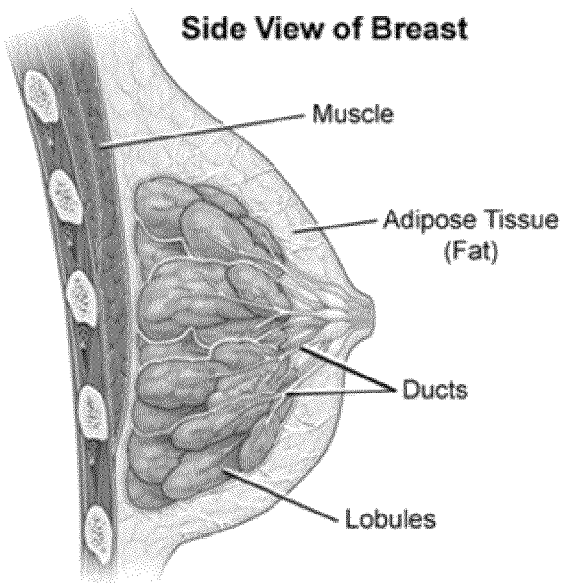
FIG. 1. Anatomy of the female breast.

Before the present composition, methods, and methodologies are described, it is to be understood that this invention is not limited to particular compositions, methods, and experimental conditions described, as such compositions, methods and conditions may vary. It is also to be understood that the terminology used herein is for purposes of describing particular embodiments only, and is not intended to be limiting, since the scope of the present invention will be limited only in the appended claims.

DEFINITIONS

As used herein, the recited terms have the following meanings. All other terms and phrases used in this specification have their ordinary meanings as one of skill in the art would understand. Such ordinary meanings may be obtained by reference to technical dictionaries, such as Hawley's Condensed Chemical Dictionary 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one or skill in the art, particularly when read in context of its usage. For example, one or more can refer to one or two, one to three, one to four, one to five, one to six, etc.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or tow integers greater than and/or less than a recited integer at each end of the range. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and subcombinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment," and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "chemoprevention" refers to the use of chemical agents to prevent cancer development in high-risk individuals. Chemopreventive agents slow, block, suppress, or reverse the effects of cancer causing factors. Chemopreventive agents may interfere with initiation, promotion, progression, or all stages of multistage carcinogenesis. Selective estrogen receptor modulators (SERMs) are currently used for the prevention and treatment of breast cancer. They act by binding to estrogen receptors (ER) and interfering with the action of estrogen induced cell proliferation in the breast. However, the use of SERMs such as tamoxifen and raloxifene, are associated with severe side effects such as blood clots, stroke, uterine cancer, and cataracts. These side-effects have led to poor patient compliance with SERMs. Thus there is a need for developing safe and effective chemopreventive agents for breast cancer.

The compound "santalol" refers to both alpha-santalol and beta santalol. α-Santalol is a natural terpene. The liquid α-santalol is the major constituent (~61%) of the essential oil of Sandalwood oil. While both enantiomers can be effective for treating various conditions, alpha-santalol has been found to be suitably effective as described herein. The chemical structure of alpha-santalol is:

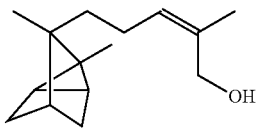 [SMILES: C/C(=C/CCC1(C)C2CC3C(C2)C31C)CO]

The chemopreventive properties of α-santalol against both chemical and UV-induced skin cancer have been extensively studied (Dwivedi, C, Abu-Ghazaleh, A.; Eur. J. Cancer Prev. 1997; 6:399-401). However, prior to this disclosure, its effects against breast cancer were not known. This disclosure demonstrates that α-santalol be an effective chemopreventive/chemotherapeutic agent for breast cancer.

Figure 2:
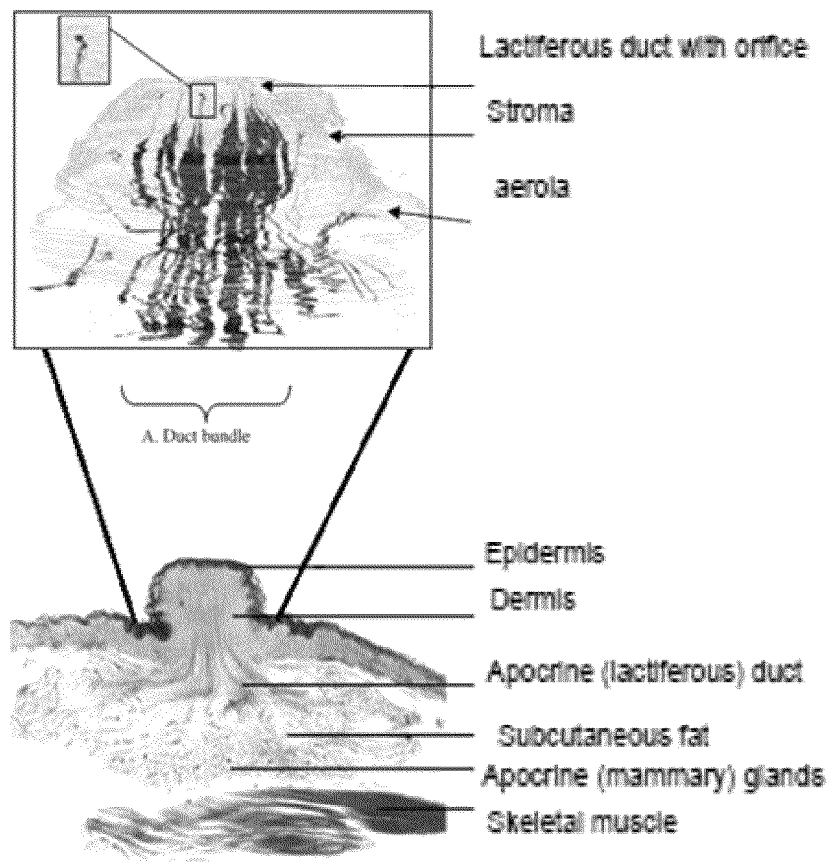
FIG. 2. Anatomy of a mammary papilla.

The "mammary papilla" or "nipple" is a projection on the breast used for delivering milk to offspring by female mammals. Milk is produced in lobules of the mammary glands and the milk is delivered via ducts that open on the surface of the mammary papilla (FIG. 1). The mammary papilla is mainly composed of the epidermis and the dermis (FIG. 2). Each mammary papilla includes approximately 10-15 ducts that lead from the surface of the mammary papilla to various lobules. Mammalian ducts are typically about 10-60 microns in diameter. Corneocytes, which are stratified keratinocytes, are the cells mainly responsible for the barrier function of the skin. The corneocytes of the mammary papilla epidermis are smaller and less concentrated than the corneocytes for other skin (600 corneocytes per cm2 for mammary papilla and 800 corneocytes per cm2 for normal skin). This difference results in the mammary papilla being a more permeable tissue than normal skin. There are also fewer layers of corneocytes in the mammary papilla compared to normal skin, resulting in a higher rate of transepidermal water loss compared to normal skin, indicating the less obstructive nature of the mammary papilla.

The majority of breast cancers originate in the epithelial cells lining the ducts in the breast. Therefore, localized delivery of chemopreventive/chemotherapeutic agents could be a promising approach for prevention and treatment of breast cancer (Lee et al., Int. J. Pharm. 2010, 387, (1-2), 161-166). The mammary papilla is the exit point for delivering milk through ducts produced in globules. The openings on the surface of the mammary papilla are in the size range of 50-60 μm (Rusby et al., Breast Cancer Res. Treat. 2007, 106, (2), 171-179).

Furthermore, the epidermis is thinner in the mammary papilla compared to the surrounding breast skin (14 layers of corneocytes compared to 17) (Kikuchi et al., Br. J. Dermatol. 2011, 164, (1), 97-102). Therefore, by topical application on the mammary papilla, therapeutic agents can be directly delivered to the ducts and lobules in the breast. This invention provides compositions and methods of using mammary papilla as a route for localized drug delivery to the breast.

The invention provides compositions and methods for drug delivery to the breast through the mammary papilla (nipple). Studies were performed with excised porcine mammary papilla. 5-fluorouracil (5FU; MW=103 Da; Log P=−0.89), estradiol (EST; MW=273 Da; Log P=3.6) and bovine serum albumin (BSA; MW=67 kDa) were used as model hydrophilic, hydrophobic and macromolecular compounds, respectively. Microscopic studies were performed after treatment with hydrophilic dye sulforhodamine B (SRB) and lipophilic dye Nile Ned (NR). The retention of 5FU and EST in the mammary papilla was similar but higher amounts of 5FU were found to be transported across the tissue. BSA was mainly retained in the mammary papilla and did not travel across it. Microscopic studies showed that both dyes are taken up into the ducts of the mammary papilla. There were differences in the distribution of the dyes in the mammary tissue based on the physicochemical properties of the dyes. The transport of therapeutic agents into and across the mammary papilla is dependent on the physicochemical properties of the drug as well as the properties of the delivery vehicle composition. Overall, the study showed that the mammary papilla is a favorable route for drug delivery. The invention therefore provides effective delivery strategies for the prevention and treatment of breast cancer and adverse conditions of the breast.

Accordingly, this invention deals with a novel delivery route through the breast nipple to treat breast cancer and other mammary diseases. The method utilizes the microscopic openings in the nipple to deliver drugs directly to the nipple and underlying breast tissue. This can result in a high local concentration with minimal systemic concentration thereby reducing the dose, dosing frequency and more importantly reducing the system side effects of drugs. These results can be achieved by direct topical application on the mammary papilla and/or the surrounding areola.

The invention identifies the type of molecules that can be delivered through the breast nipple in various embodiments. It was found that the drug delivery to and through the breast nipple is strongly influenced by the physicochemical properties of drug molecules. The studies were carried out in vitro using excised porcine breast tissue.

The invention provides a variety of methods to enable the efficient and effective delivery of actives through nipple. Based on our in vitro findings, novel formulations for nipple drug delivery have been developed. The novel formulations can include emulsions, lotions, creams, ointments, gels, nanoparticles, micelles, liposomes, and the like, each of which can be optimized to maximize breast delivery of the active.

Physical enhancement methods such as iontophoresis can also be used to enhance the delivery. Iontophoresis uses a small electric current to deliver charged molecules across membranes. Several novel formulation and device designs have been developed. Additionally, the natural chemopreventive agent santalol can be delivered into the breast for prevention of breast cancer.

The compositions and methods of various embodiments can provide one or more of the following advantages.

1. Localized drug delivery. Currently, most of anticancer agents for breast cancer are administered orally or by injection. These routes are often characterized by systemic side effects. The delivery methods described herein provide localized drug delivery to the target site in the breast.

2. The delivery strategy described herein can be used as a simple topical formulation applied directly on the breast. This method can be particularly advantages for preventive therapies for breast cancer. For example, the active agent or active agent composition can be incorporated in a body lotion, gel, or the like.

3. Localized delivery will lead to reduced dose and dosing frequency. More importantly, the localized delivery will reduce the side effects associated with systemic therapy.

4. Unlike systemic routes, the therapy can be easily discontinued by removing the formulation, for example, by washing or removing the device from the breast.

5. Topical breast delivery can overcome the limitations of oral delivery such as degradation in the gastrointestinal tract and first pass metabolism in the liver.

6. The delivery can also be useful for patients who cannot take the drug orally due to vomiting or diarrhea associated with certain actives and oral formulations.

7. The prophylactic and therapeutic approaches described herein can lead to enhanced efficacy and reduced side-effects of anticancer and other therapeutic agents for breast conditions, leading to high patient compliance.

In some instances there can be issues with regard to skin irritation from certain actives and formulations. The issues can be overcome by formulation approaches such as encapsulation in liposomes or nanoparticles, and also using sustained release formulations. The depth of penetration into mammary tissue can also be enhanced by using physical method such as iontophoresis, ultrasound, microneedles, and the like. Furthermore, the delivery carriers (liposomes or others) can be combined with various physical approaches (e.g., iontophoresis and the like).

As disclosed herein, the methods and compositions surprisingly afford significant transport of macromolecules through the nipple. Further, the disclosure provides that transport through the nipple/aerola is higher than through surrounding breast skin. Similarly the localized delivery into the breast tissue is higher when delivered through nipple/aerola than through surrounding breast skin. The present disclosure also shows that hydrophilic, hydrophobic and macromolecules can be delivered via the transmammary route using various formulations, and that certain formulations achieve higher penetration than others (e.g., alcoholic solution vs. microemulsion). Another surprising observation relates to the removal of keratin plugs by simple alcohol swab, such an action was found to significantly increases transmammary transport, and while not being bound by theory, does not seem to involve the alcohol as carrier, since it has evaporated prior to composition addition.

Compositions of the Invention

The compositions of the invention can include one or more active agents, as well as one or more solvents, adhesive base materials, and the like. Examples of solvents include water; polyhydric alcohols such as ethylene glycol, diethylene glycol, triethylene glycol, ethylene glycol monoethyl ether, ethylene glycol monobutyl ether, diethylene glycol monomethyl ether, polyethylene glycol, propylene glycol, dipropylene glycol, 1,3-butylene glycol, dipropylene glycol polyethylene glycol, 2-ethyl-1,3-hexane diol, polypropylene glycol 2000, polypropylene glycol, glycerin, butyl alcohol, pentaerythritol and D-sorbitol liquid; alcohols such as ethanol, isopropanol, benzyl alcohol, lauryl alcohol, cetanol, stearyl alcohol, oleyl alcohol and lanolin alcohol; diisopropyl adipate triacetin, diisopropyl sebacate, triisooctane acid and esters such as triglycerides of medium chain fatty acids having 6 to 12 carbon atoms; ketones such as crotamiton; or a combination thereof.

Examples of adhesive base materials include water-soluble adhesive base materials such as polyacrylic acid, sodium polyacrylate, partially neutralized polyacrylic acid and N-vinyl acetamide-acrylic acid co-polymers, and hydrophobic adhesive base materials such as ester gums, alicyclic saturated hydrocarbon resins, aliphatic hydrocarbon resins, polybutene, rosin, or a combination thereof.

Base materials, thickening agents, preservatives, pH adjusters, oil ingredients, flavoring agents, stabilizers, surfactants, curing agents and chemical enhancers can also be included in the composition.

Examples of base materials include sodium alginate, ethyl cellulose, carrageenan, carmellose sodium (carboxymethylcellulose sodium), agar, xanthan gum, gelatin, kaolin, bentonite, montmorillonite, zinc oxide, titanium oxide, silicic anhydride, D-sorbitol, talc, terpene resins, hydroxypropylcellulose (HPC), hydroxypropylmethylcellulose (HPMC), and combinations thereof.

Examples of thickening agents include carboxyvinyl polymer, urea, polyvinyl alcohol, sodium metaphosphate, and combinations thereof.

Examples of preservatives include phenolic substances such as methyl para-hydroxybenzoate, phenol and cresol, neutral substances such as chlorobutanol and phenylethyl alcohol, invert soaps such as benzalkonium chloride and benzethonium chloride, acidic substances such as benzoic acid, sorbic acid, dehydro acid and salicylic acid, and combinations thereof.

Examples of pH adjusters include citric acid, sodium citrate, hydrochloric acid, glycine, succinic acid, acetic acid, diisopropanolamine, tartaric acid, potassium hydroxide, sodium hydroxide, lactic acid, boric acid, malic acid and phosphoric acid, and combinations thereof.

Examples of oil ingredients include olive oil, camellia oil, castor oil, safflower oil, sunflower oil, sasanqua oil, soybean oil, cottonseed oil, sesame oil, coconut oil, palm oil, clove oil, and combinations thereof.

Examples of flavoring agents include fennel oil, cinnamon oil, clove oil, peppermint oil, and combinations thereof.

Examples of stabilizers include anti-oxidants such as vitamin E and butylhydroxyanisol, reducing agents such as ascorbic acid, sodium hydrogen sulfite and sodium thiosulfate, and synergistic agents such as sodium citrate, sodium tartrate, lecithin, EDTA, and combinations thereof.

Examples of surfactants include anionic surfactants such as calcium stearate, magnesium stearate and sodium lauryl sulfate, cationic surfactants such as benzalkonium chloride, benzethonium chloride and cetylpyridinium chloride, nonionic surfactants such as glyceryl monostearate, sugar fatty acid esters, polyoxyethylene hydrogenated castor oil, polyoxyethylene sorbitan fatty acid esters, and combinations thereof.

Examples of chemical enhancers include nonionic surfactants such as monostearic acid glyceryl and sugar fatty acid esters, water-soluble polymer compounds such as carboxylic acids, aromatic carboxylic acid compounds such as salicylic acid and the derivatives thereof, aliphatic carboxylic acid compounds such as capric acid and oleic acid, terpenes such as L-menthol, esters such as isopropyl myristate and diethyl sebacate, bile salt, hydrogenated lanoline, Azone (laurocapram), and combinations thereof.

The compositions described herein can be used to deliver actives to the breast using a variety of products, including but not limited to, gels, creams, lotions, ointments, patches, bra pads, nipple pads, nipple shields, and the like. The medicated nipple shield can be, for example, made of silicone and can include an insert at the inner portion of the nipple that includes an active agent or a composition described herein. The content of the active ingredient in the composition can be 0.01 to 40 mass %, preferably 0.1 to 10 mass %.

In some embodiment, the preparation of topical formulations can be carried out using commonly used semi-solid dermatological bases (Thomson J. E.; A practical guide to contemporary pharmacy practice; 2nd Ed., Lippincott Williams & Wilkins, Hagerstown, Md., 2004; pp. 30.1-30.6), including hydrocarbon bases, anhydrous absorption bases, water in oil emulsion bases, oil in water emulsion bases and water soluble bases. For example, to prepare an α-santalol formulation, α-santalol (50 mg) can be dissolved in 70% alcohol and incorporated into a portion of the base, then diluted with remaining portion of the base to make 10 g of the formulation (5% w/w). For a gel preparation, hydroxypropyl methyl cellulose (10 g) can be added to water at 60-65° C. and then stirred to cool to room temperature (~23° C.): α-santalol (20 mg) in 70% alcohol can be added gradually to the gel with stirring to homogenously disperse the α-santalol in the gel. The α-santalol concentration in the formulations can be determined after extraction using GC-MS methods.

Methods of the Invention

The compositions described herein can be used, for example, for the prevention and treatment of breast cancer. Almost all (>95%) breast cancers start from the duct and the lobules in the breast. Therefore, the compositions and methods described herein provide attractive alternatives for current breast cancer treatments. In particular, α-santalol has been identified as an effective chemopreventive/chemotherapeutic agent for breast cancer. The methods can be used for treating both estrogen receptor (ER)-positive breast cancer cells and estrogen receptor (ER)-negative breast cancer cells, thus α-santalol is a broad anti-proliferative agent against each of the different types of breast cancer. Accordingly, the compositions and methods described herein can be useful for the treatment of a variety of cancer types, including ductal carcinoma in-situ (DCIS), infiltrating ductal carcinoma (IDC), medullary carcinoma, infiltrating lobular carcinoma (ILC), tubular carcinoma, mucinous carcinoma (Colloid), or inflammatory breast cancer (IBC).

The compositions described herein can also be used as an adjuvant treatment for conventional chemotherapy and/or radiotherapy in breast cancer. Similarly, they can be used as a follow up or prior to breast surgery. The compositions can also be used for the delivery of chemopreventive agents to women with a high risk of breast cancer.

In some embodiments, the compositions can be used for the delivery of diagnostics to the breast. In various other embodiments, the compositions can be used for treating early stage breast cancer. In further embodiments, the compositions can be used for treatment of nipple disease such as Paget's disease.

Because the mammary gland has a rich lymphatic supply, the compositions can be used for treating metastatic breast cancer. Similarly, the lymphatic system can be used for vaccine delivery.

Furthermore, the approach can be used for both men and women. Additionally, in the veterinary field, this approach can be used for treating mastitis and other breast diseases in animals. The invention provides several formulations and devices that can be used for transmammary drug delivery, including emulsions, gels, creams, lotions, ointments, patches, and the like.

In some embodiments, the compositions and methods described herein can be used in conjunction with iontophoresis, such as the methods described in U.S. patent application 2009/0281063 (Inagi et al.).

Active Agents

Examples of anticancer agents that can be delivered by compositions and methods described herein include: alkylating agents such as ifosfamide, cyclophosphamide, and ThioTEPA; platinum compounds such as carboplatin, cisplatin, nedaplatin and oxaliplatin; anticancer agents such as irinotecan hydrochloride, etoposide, docetaxel hydrate, vincristine sulfate, vinblastine sulfate, paclitaxel vinorelbine ditartrate, eribulin mesylate, and ixabepilone; hormones such as tamoxifen, tamoxifen citrate, 4-hydroxy tamoxifen, endoxifen, toremifene, estradiol, fadrozole hydrochloride hydrate, flutamide and medroxyprogesterone acetate; estrogen receptor antagonists such as fulvestrant; progestins such as megestrol acetate; anticancer antibiotics such as doxorubicin hydrochloride, idarubicin hydrochloride, zinostatin stimalamer, daunorubicin hydrochloride, bleomycin hydrochloride, epirubicin hydrochloride, mitoxantrone hydrochloride, pirarubicin hydrochloride and mitomycin C, as well as their free bases; antimetabolites such as capecitabine, carmofur, cytarabine, doxifluridine, gemcitabine, hydroxycarbamide, methotrexate, mercaptopurine, gemcitabine hydrochloride, fluorouracil and capecitabine; linear surfactin having a lactone type cyclohepta-peptide structures; aromatase inhibitors such as anastrozole, exemestane, and letrozole; GnRH analogues such as goserelin; Selective Estrogen Receptor Modulators (SERM) such as raloxifene; and tyrosine kinase inhibitors such as lapatinib.

Examples of the non-steroidal anti-inflammatory agents that can be delivered by compositions and methods described herein, such as for the treatment of breast cancer and/or mastitis, include indomethacin, acemetacin, salicylic acid, sodium salicylate, aspirin, acetaminophen, diclofenac sodium, anfenac sodium, ibuprofen, sulindac, naproxen, ketoprofen, flufenamic acid, ibufenac, fenbufen, alclofenac, phenylbutazone, mefenamic acid, benzadac, piroxicam, flurbiprofen, pentazocine, buprenorphine hydrochloride, butophanol tartrate, celecoxib, rofecoxib, valdecoxib, etoricoxib, Lumiracoxib, parecoxib Na, etodolac NS-398 and meloxicam.

Examples of macromolecular agents that can be delivered by compositions and methods described herein include proteins, antibodies, gene therapy agents, and the like. Specific examples of therapeutic macromolecules include monoclonal antibodies and humanized monoclonal antibodies. Specific examples include: monoclonal antibodies such as trastuzumab; angiogenesis inhibitors such as bevacizumab, a humanized monoclonal antibody; Human Epidermal Growth Factor Receptor (HER2) inhibitors such as trastuzumab, a humanized monoclonal antibody; and HER2 dimerization inhibitors such as pertuzumab, another humanized monoclonal antibody.

Further examples of cancer drugs approved by the Food and Drug Administration (FDA) for breast cancer can be found at the National Cancer Institute website, hosted by the National Institutes of Health (NIH), Bethesda, Md.

Cancer Chemotherapy

Currently all approved breast cancer therapeutics are delivered orally or by injection. When cancer therapeutics are administered by these routes, the entire body, including healthy organs, can be exposed to the therapeutics, which can have toxicity toward normal tissue. Such systemic administration can lead to severe side effects including, but not limited to, uterine cancer, leukemia, cardiac dysfunction, cognitive dysfunction, and neuropathy. For example, the use of current chemopreventive agents for breast cancer, such as tamoxifen, is limited in clinical practice by the severe side effects of these drugs. There is therefore a strong need for developing new and safe chemopreventive agents and methods.

Figure 3A:
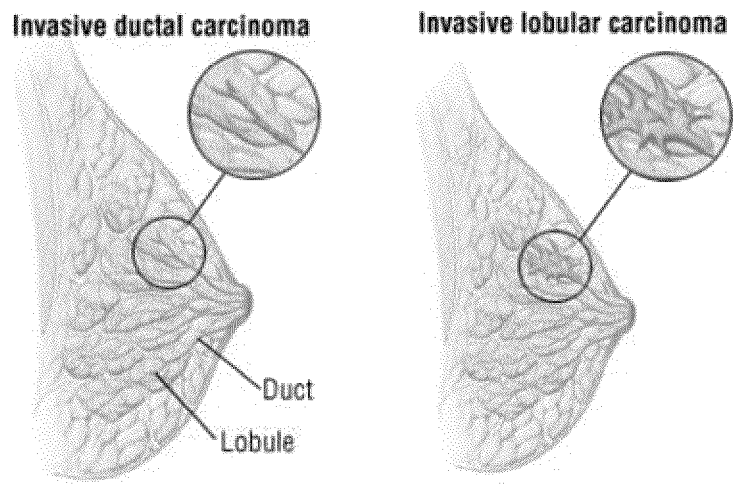
FIG. 3 (A) Schematic illustrations of invasive ductal carcinoma and invasive lobular carcinoma; and (B) an example of a device that can be used to facilitate delivery of the compositions described herein, according to one embodiment.
Figure 3B:
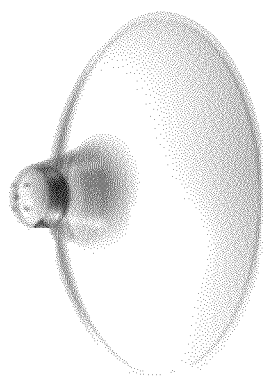

In various embodiments, this disclosure provides compositions of α-santalol as a chemopreventive/chemotherapeutic agent for breast cancer. Due to the relatively permeable epidermis of the mammary papilla and the multi-micron sized openings of nipple, the mammary papilla can be an effective route to provide cancer therapeutics with reduced systemic effects. Furthermore, drug delivery through the nipple can deliver actives to the ductal epithelium where more than 95% of breast cancers arise (FIG. 3). Administration of the compositions can be by localized delivery through the mammary papilla (nipple) using a topical formulation. Such compositions have been found to be effective against several forms of breast cancer cells through their anti-proliferative and apoptotic effects. Accordingly, drug delivery via the mammary papilla can target specific areas, thereby protecting other healthy organs against often cytotoxic drugs and their various adverse effects.

α-Santalol is a major component of sandalwood oil and is a chemopreventive agent against skin cancer. However, the use of α-santalol for prevention/treatment of breast cancer has heretofore not been studied. This disclosure provides the research and data necessary to show that α-santalol can be delivered via the mammary papilla for the treatment of breast cancer.

The localized delivery to the breast tissue through the mammary papilla using santalol is a novel concept. Cancer cell growth is regulated by cell cycle and signaling pathways that control cell proliferation survival and apoptosis. Therefore based on the studies described herein, the invention provides for the transmammary delivery of α-santalol as an effective chemopreventive/chemotherapeutic agent for breast cancer through its anti-proliferative and apoptotic effects as broad chemopreventive agents against all known types of breast cancer. Due to its small molecular weight and lipophilicity, α-santalol can be transported through the mammary papilla to produce a high local concentration in the breast tissue.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Evaluation of In-Vitro Penetration and Permeation Via Mammary Papillae

Drug penetration and permeation studies were performed to evaluate the feasibility of delivering various drug compounds into breast tissue through the mammary papilla. The compounds 5-fluorouracil (5FU), estradiol (EST), and bovine serum albumin (BSA) were used as examples of model hydrophilic, hydrophobic, and macromolecular drugs. The study determined whether these drug compounds can enter and pass through the mammary papilla by evaluating them in vitro using excised porcine mammary papilla.

Figure 4:
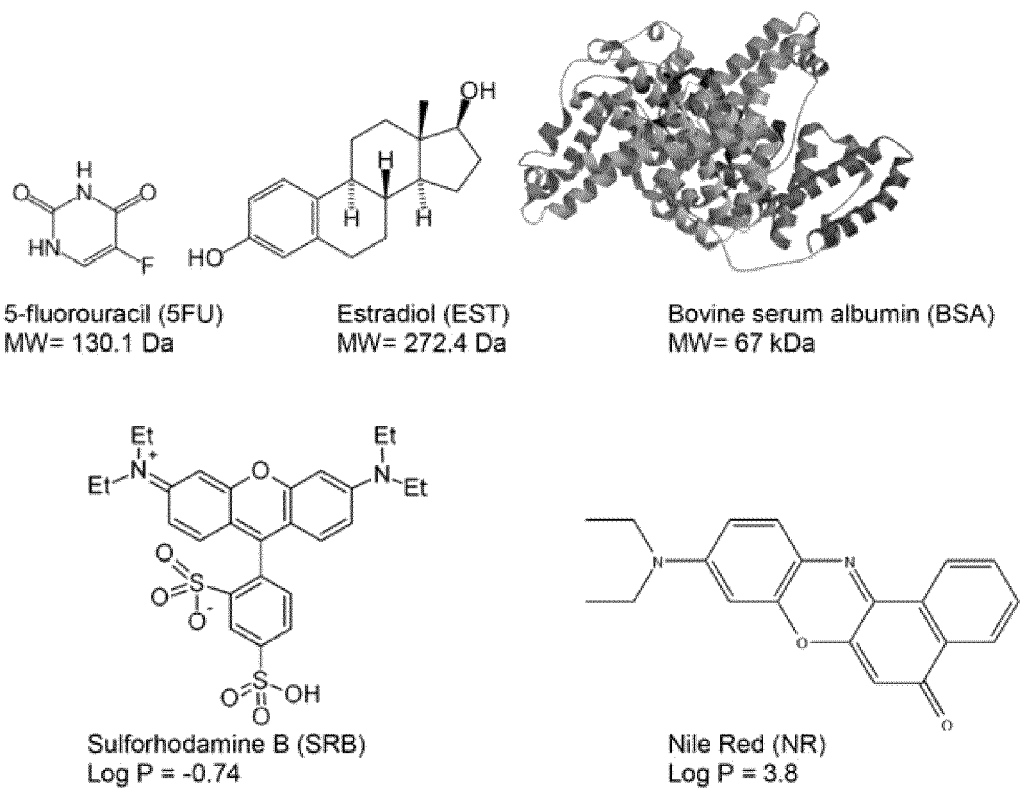
FIG. 4. Structures of certain therapeutic agents and model drug compounds.

Drug penetration and permeation via mammary papillae was performed in a Franz diffusion cell using excised porcine mammary papilla. Mammary papillae were individually treated with a saturated solution of 5FU spiked with 14C-5FU, a saturated solution of EST spiked with 3H-EST in ethanol:water (50:50), and a sub-saturated solution of BSA (10 mg/ml) in phosphate buffer spiked with 14C-BSA (FIG. 4). The receptor medium was phosphate buffer (pH 7.4) for 5FU and BSA, while ethanol: phosphate buffer (20:80) was used for EST. The transport studies were performed at time points for 6 and 48 hours.

In a separate study to evaluate the drug retention and disposition, the treatment was removed after 6 hours and the study was continued until the 48 hour mark. Samples were withdrawn from the receptor compartment at different time points. At the end of study, the mammary papilla was cut to 2 mm thick cylindrical sections from the top to the base of the tissue and was digested using a tissue solubilizer. The drug concentrations were determined by liquid scintillation counting.

For dye penetration studies, 10 mM of the dye sulforhodamine B (SRB) in 1:1 of ethanol:phosphate buffer and 0.32 mM of Nile Red (NR) in propylene glycol were applied on the mammary papillae for 12 hours. The structures of SRB and NR are shown in FIG. 4. At the end of the study, the tissue was washed, cut into 2 mm thick sections as described earlier and placed on a glass slide for confocal microscopy study. Confocal images of mammary papilla were taken from approximately 5 mm below the surface of the mammary papilla.

Methods for the preparation of porcine mammary papilla. Freshly excised strips of porcine mammary papilla (6-7 months old animals) were washed with deionized water followed by removal of subcutaneous fatty tissue using a scalpel. Keeping the mammary papilla in the center, 3 cm×3 cm sized specimens of the tissue were excised, subcutaneous fat tissue was removed, and the tissue was frozen at −20° C. until used for the drug penetration and permeation studies.

Methods for the penetration and permeation studies for 5FU and EST via mammary papilla. Breast tissue was mounted between the two compartments of a vertical Franz diffusion cell (FDC) with breast tissue sandwiched between donor and receptor compartments. A mammary papilla was set in upright position inside the donor compartment of Franz diffusion cell. Reception medium was phosphate buffer (pH 7.4) for 5FU and ethanol:phosphate buffer (20:80) for EST, (n=3). The mammary papilla was treated via the donor chamber with saturated solution of 5FU (spiked with 14C-5FU) and EST (spiked with 3H-EST), both prepared in ethanol: water (50:50). Samples were withdrawn from the receptor at different time points for 48 hours to determine drug concentration by radioactive count. At the end of 48 hours, tissue samples were taken for drug content determination.

The first study was a 6 hour study where the drugs were applied continuously for 6 hours and permeation was evaluated for 6 hours. This analysis parallels recommended procedures for using commercially available topical formulations, which are typically applied every 6 hours.

In a second study, the mammary papillae in Franz diffusion cells were treated with the drugs for 48 hours and the permeation was followed through 48 hours. This analysis provided information regarding any saturation from drug treatment for extended periods of time.

In a third study, the mammary papillae in Franz diffusion cells were treated with the drugs for 6 hours and the permeation profile analysis was continued through 48 hours. Thus, at the sixth hour, the drug was removed from the surface of nipple but samples were collected from the receiving cell through 48 hours.

Extraction of drugs from the mammary papilla. At the end of permeation study, the mammary papilla was removed from Franz diffusion cell and thoroughly washed with deionized water and blotted dried. Approximately 2 mm thick sections of the tissue were taken using a scalpel. These sections were homogenized, the drug was extracted, and the drug concentration was determined by radioactive counts.

Results and Discussion. A significant amount of 5FU passes through the mammary papilla when treated for 6 or 48 hours. Even in the case of the 6 hour treatment, 5FU passage continued to increase through 48 hours, potentially due to drug depot formation in the nipple that then passed into the receptor chamber over time.

Figure 5:
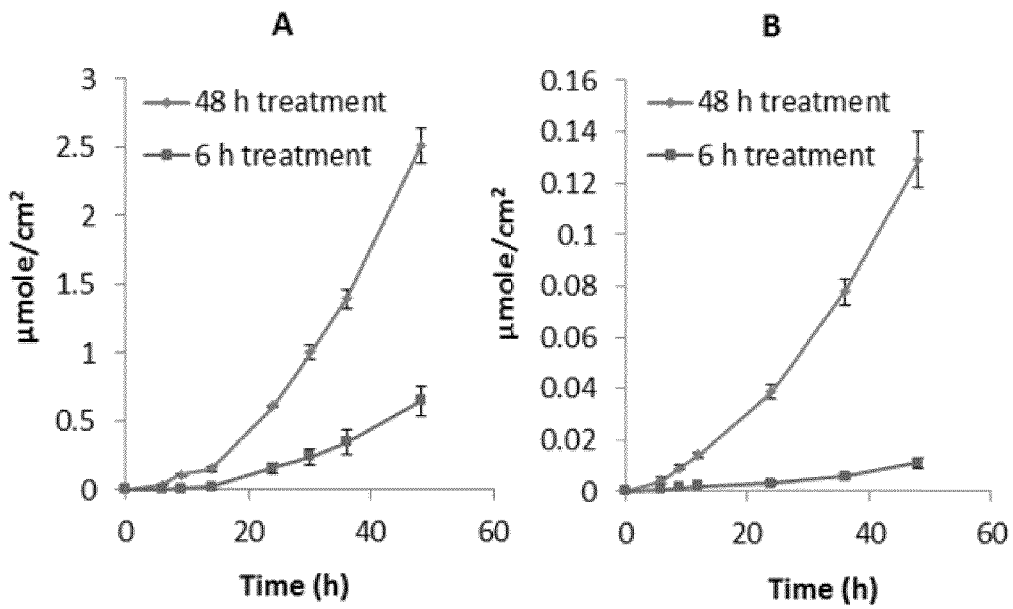
FIG. 5. Profile of (A) 5FU and (B) EST permeation across mammary papillae after treatment for 6 and 48 hours. In the 6 hours study, the treatment was removed after 6 hours and the disposition was measured until 48 hours. Each data point is represented as mean±SD (n=3).

After treating the mammary papilla for 6 hours and removing the 5FU treatment, the drug retained in the tissue was found to be continuously transported across the papilla for 48 hours, as shown in FIG. 5A. The y axis shows the amount of drug permeating across the nipple per cm2. The upper line data (marked by diamonds) illustrates the permeation data over the course of 48 hours of treatment. The lower line data (marked by squares) illustrates the permeation data over the course of 48 hours, where after the sixth hour the drug was removed from the donor chamber and samples were collected through 48 hours. Thus, longer applications of 5FU on the mammary papilla resulted in significantly higher permeation across the tissue.

In contrast to the hydrophilic drug 5FU, the permeation of hydrophobic drug EST across mammary papilla was relatively less after 6 hours of treatment (FIG. 5B). The difference can be attributed to formation of EST depots in the lipophilic matrix of the mammary papilla. This is evident from the considerably retention of EST in the mammary papilla (FIG. 6B). However, with extended treatment, i.e. 48 hours, significant EST transport across the mammary papilla was found, likely because of saturation of the binding to the mammary papilla matrix. During 48 hours of treatment, this binding with fat appears to reach a saturation point, thereby allowing excess EST to cross the nipple tissue, as shown by the upper line of FIG. 5B (marked by diamonds). This is not the case with the 6 hour treatment where little drug passes through the nipple through 48 hours.

Figure 7:
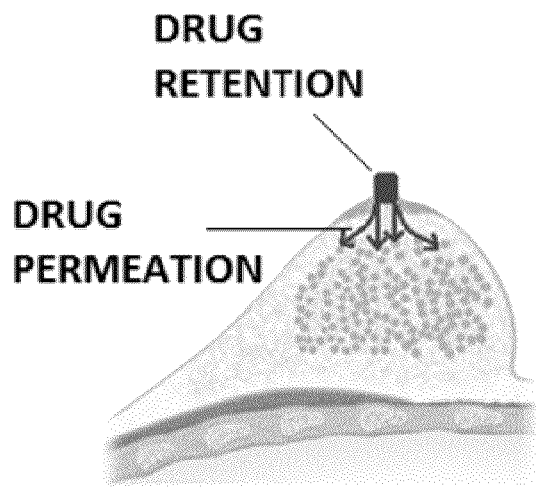
FIG. 7. Schematic representing the locations of drugs when retained in the mammary papilla and when permeation through the mammary papilla occurs.

Table 1 shows the data obtained from the mammary papilla permeation studies (see also FIG. 7).

TABLE 1

Mammary papilla permeation parameters for 5FU and EST.

| Drug name | Lag time (h) | Flux × 10³ ($\mu M \cdot cm^2 \cdot hr^{-1}$) | Permeability coefficient × 10³ ($cm^2 \cdot hr^{-1}$) | Cumulative amount permeated ($\mu M$) | Cumulative % permeated |
|---|---|---|---|---|---|
| 5FU | 8.18 ± 0.79 | 38.46 ± 2.38 | 0.25 ± 0.015 | 4.38 ± 0.04 | 5.71 ± 0.06 |
| EST | 7.07 ± 0.29 | 2.57 ± 0.15 | 0.05 ± 0.002 | 0.23 ± 0.02 | 1.03 ± 0.08 |

Results are presented as Mean ± SEM (n = 3).

Figure 6:
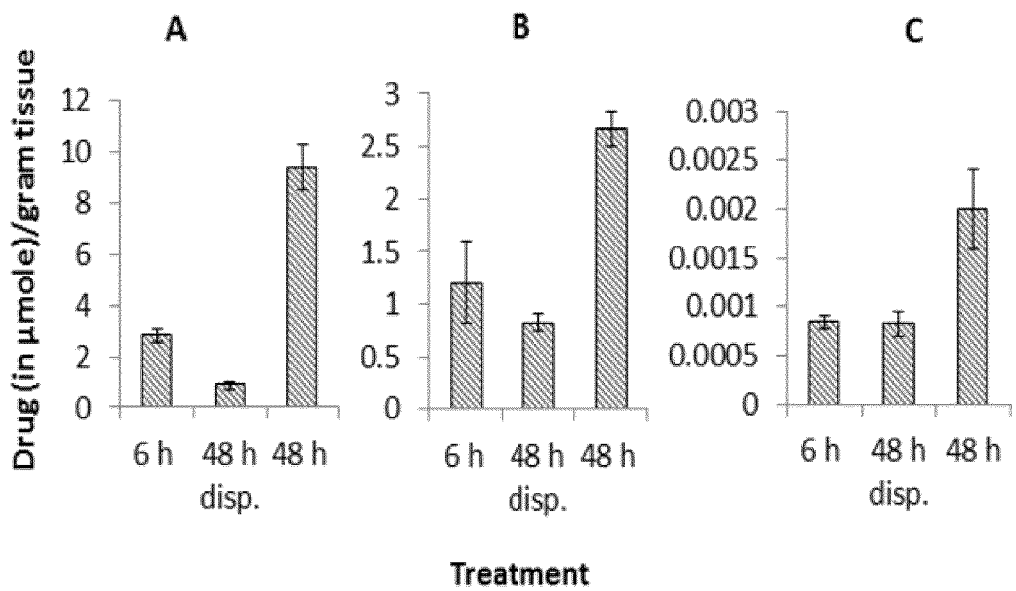
FIG. 6. Retention of (A) 5FU, (B) EST and (C) BSA in mammary papilla after 6 hours treatment, 6 hours treatment followed by 48 hours disposition study, and 48 hours treatment. Each value is represented as mean±SD (n=3).

In FIG. 6, the x axis provides the category of the three treatments. The first column shows the data for the 6 h treatment, the second column shows the data for the 6 h treatment in combination with 48 h disposition studies, and the third column shows the data for the 48 h treatment study. The y axis shows the amount of drug in $\mu$moles per gram of nipple tissue.

The retention of 5FU and EST was also higher with longer applications (FIGS. 6A and B, respectively). Evaluation of the large biomolecule BSA showed that no significant amounts of BSA passed into or across the nipple for both the 6 hour treatment and the 6 hour permeation studies. The BSA was not found to penetrate across the mammary papilla to a significant extent, even after treatment of 48 hours. The BSA was mainly retained in the mammary papilla tissue. There was no significant difference in the retention of BSA immediately after 6 hours and at the end of 48 hours (FIG. 6C). This can be attributed to relatively high molecular weight of BSA compared to 5FU and EST.

Even for 5 FU and EST, treatment for 6 hours did not result in significant penetration across the mammary papilla; a lag time of 7-8 hours was apparent. This can be attributed to the composition of mammary papilla and the path length that the drug has to cross to reach the receptor medium. The drugs may also form depots in the ducts and then slowly pass further down from the ducts toward the globules.

For the hydrophilic drug 5FU data, the highest retention is observed with 48 hours of treatment. The 6 hours of treatment showed significant retention, whereas the 48 h disposition group shows significantly less retention. Analysis of EST showed a significantly smaller difference between the 6 hour treatment and the 48 hour disposition study. This is likely because of a strong binding of EST with the fatty tissue of the mammary papilla.

Table 2 shows the data obtained from the mammary papilla retention studies (see also FIG. 7).

TABLE 2

Mammary papilla retention for 5FU and EST.

| Drug name | Drug extraction from 2 mm thick mammary papilla sections ($\mu M \cdot g^{-1}$) | | | | Cumulative amount retained ($\mu M$) | Cumulative % retained |
|---|---|---|---|---|---|---|
| | Section A (tip) | Section B | Section C | Section D (base) | | |
| 5FU | 13.47 ± 1.35 | 11.78 ± 1.69 | 9.80 ± 1.44 | 5.84 ± 1.69 | 3.80 ± 0.56 | 4.94 ± 0.74 |
| EST | 5.45 ± 0.49 | 3.63 ± 0.26 | 2.53 ± 0.31 | 1.55 ± 0.53 | 1.02 ± 0.13 | 4.52 ± 0.59 |

Results are presented as Mean ± SEM (n = 3).

Accordingly, skin permeation and retention studies indicate that hydrophilic drugs can readily pass through the nipple while lipophilic drugs are mainly retained in mammary papilla tissue. Additionally, large molecules such as BSA are significantly less able to pass into and through the mammary papilla.

To evaluate the transport pathways followed by the 5FU and EST through the mammary papilla, fluorescent dye penetration studies were performed. Sulforhodamine B (SRB) was used as a model hydrophilic dye (Log P=−0.74) and Nile Red (NR) as a model hydrophobic dye (Log P=3.8).

Figure 8:
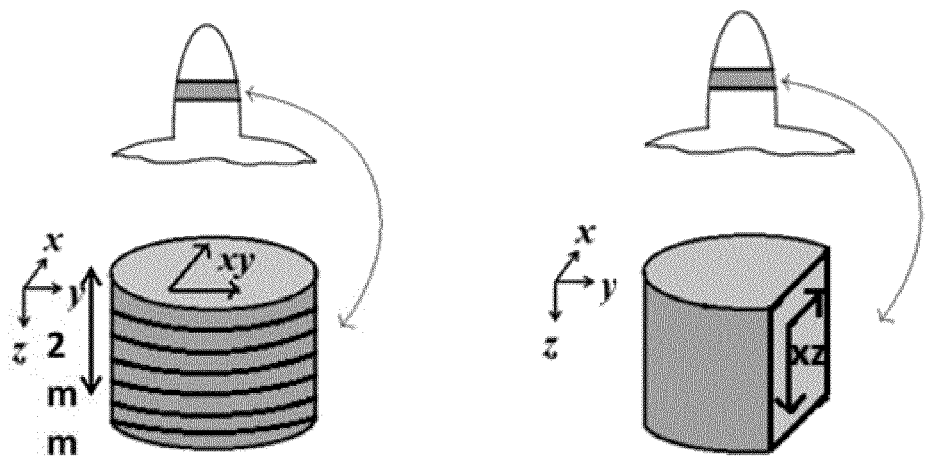
FIG. 8. Schematic representing sectioning of a mammary papilla for confocal laser scanning microscopy (sections A, B, C and D; each section was approximately 2 mm thick).
Figure 9:
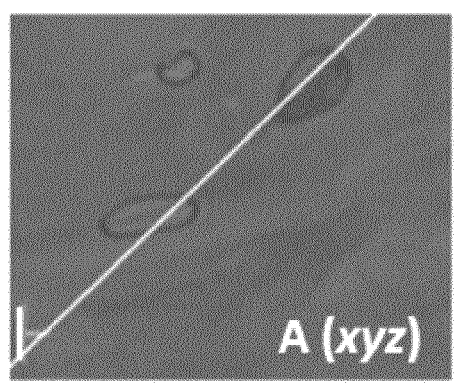
FIG. 9. Confocal microscopic images of xy and xz dimensional views of 2 mm thick sections of mammary papilla after treatment with SRB (A) and NR (B). These sections were 5 mm below from the surface of mammary papilla. The xz scans from surface to 500 μm in tissue section were taken at the position of lines drawn on the xy images. (Bar=100 μm).
Figure 9:
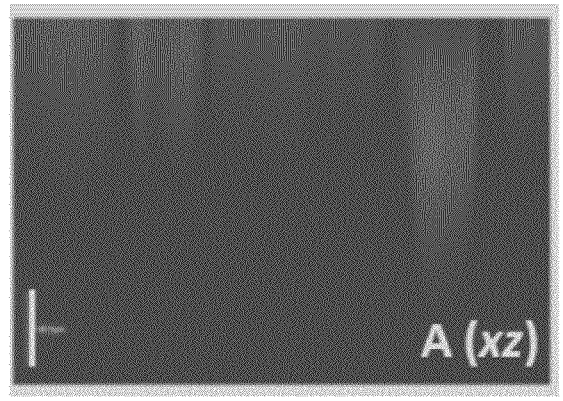
Figure 9:
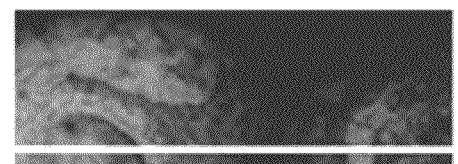
Figure 9:
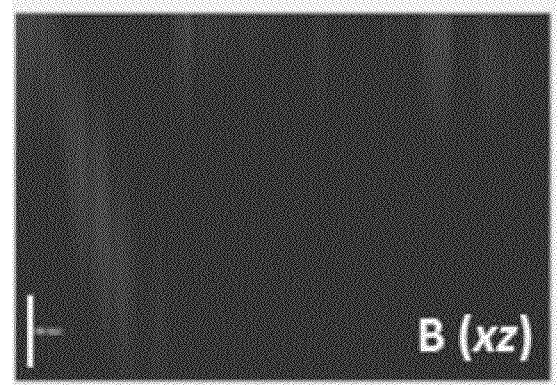

Mammary papillae were treated with each dye for 12 hours. Then, starting from tip, 2 mm thick sections of papillae were taken (FIG. 8). Section B was taken from middle of mammary papilla and studied with confocal laser scanning microscopy. From this 2 mm thick section, xy dimensional images were taken at different depths starting from 0 to 500 μm. Because xy views are taken at different depths (the dimension z), these are xyz images. The upper image is an xyz view after treatment with hydrophilic dye SRB. Fluorescence of the hydrophilic dye SRB shows the distribution of the dye in both the ducts and in the surrounding tissue (FIG. 9A). The xz views of the mammary papillae were also analyzed. In contrast to FIG. 9A, fluorescence of the lipophilic dye NR is observed only in and around the ducts (FIG. 9B). Thus, the xz view indicates that SRB is transported to all areas while the NR is transported primarily by the duct. Accordingly, confocal microscopy indicates that SRB is transported by ducts as well as the surrounding tissue, while NR is transported only through the ducts. These findings demonstrate the different transport pathways for hydrophilic and lipophilic drugs, and the results further support the drug penetration studies.

Figure 10:
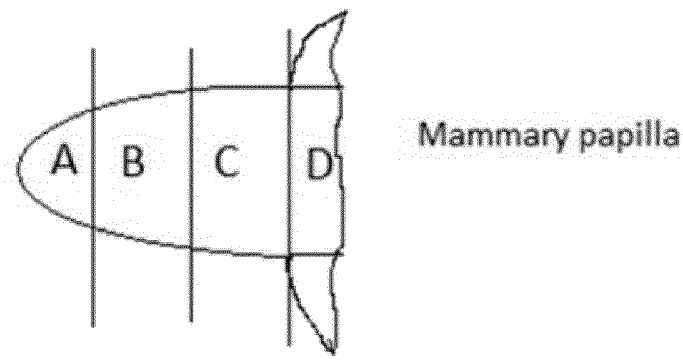
FIG. 10. Schematic representing sectioning of a mammary papilla for fluorescence microscopy.
Figure 11:
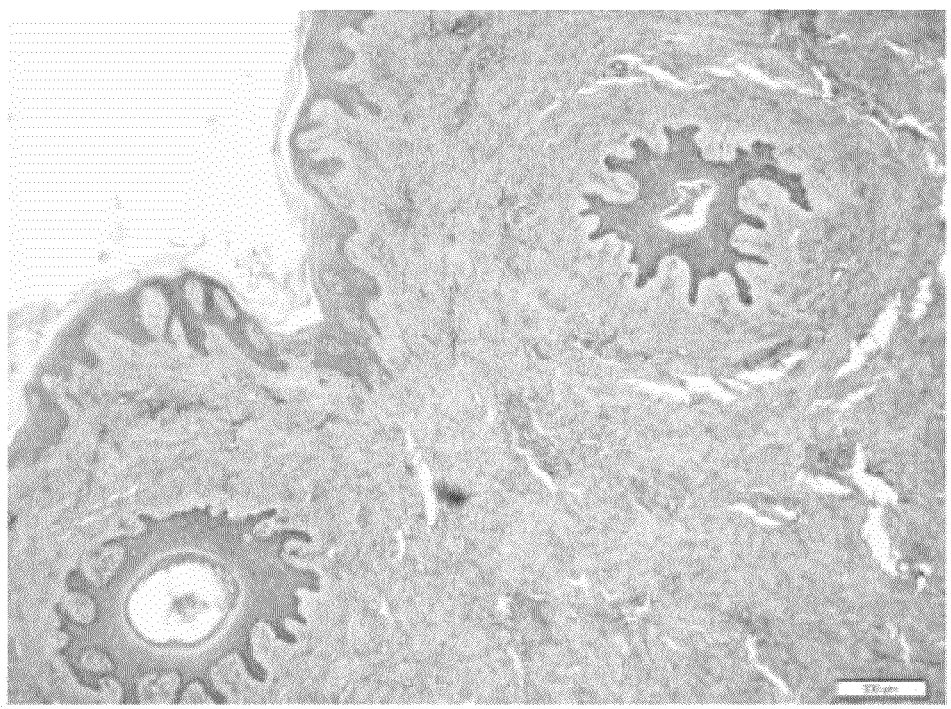
FIG. 11. Histology of a normal mammary papilla section after H&E staining.
Figure 12:
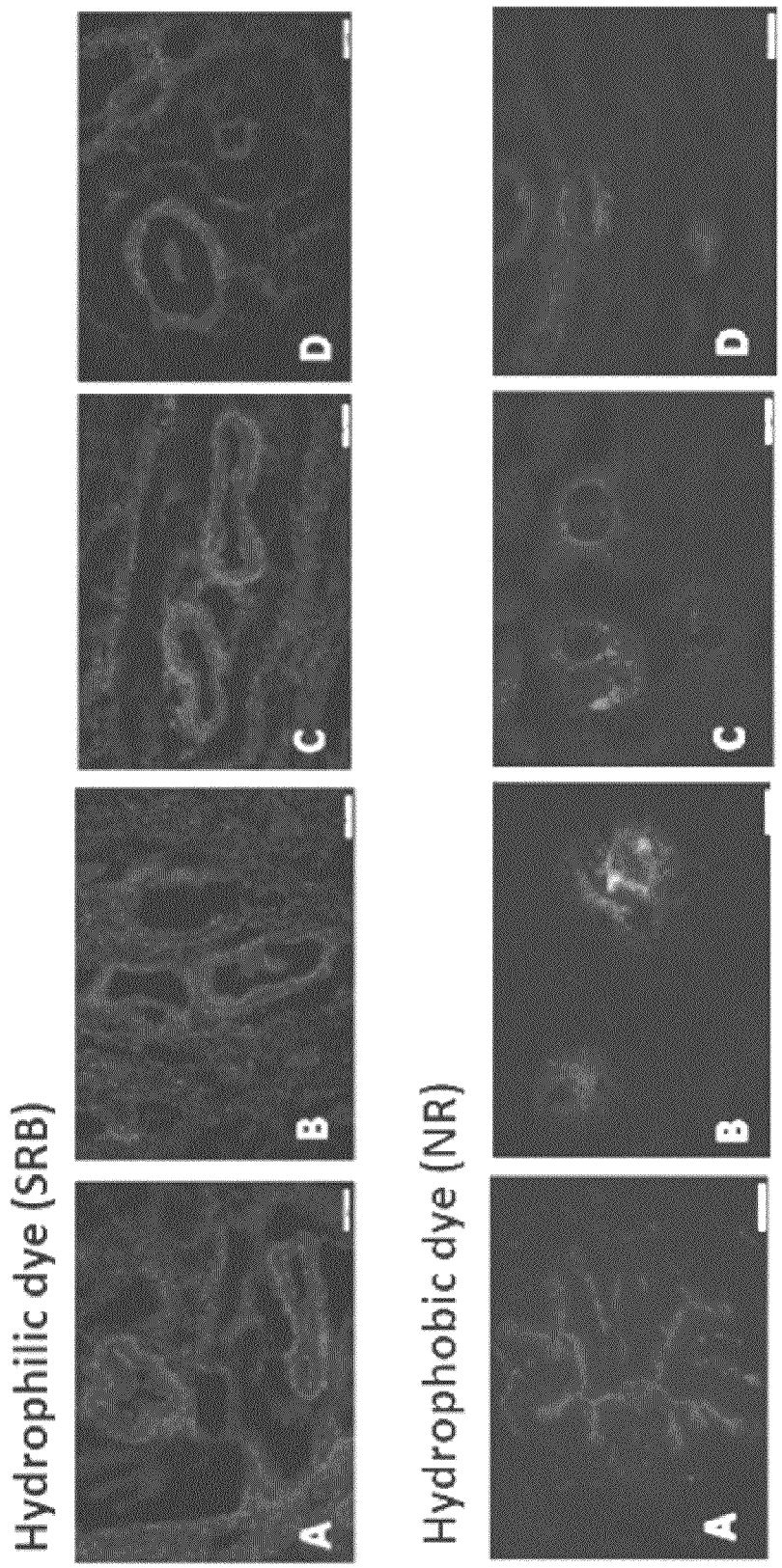
FIG. 12. Staining by the hydrophilic dye SRB (top row) and by the hydrophobic dye NR (bottom row).

Fluorescence Microscopy. To verify the confocal data, cryo-sectioning of mammary papillae was performed after 12 hours treatment with the dyes. Mammary papillae were frozen after dye treatment and 8 μm thick cryo-sections were collected from the papilla starting from the tip (FIG. 10). Sections from various different depths of the papilla and studied by fluorescence microscopy. FIG. 11 shows the histology of a normal mammary papilla section after H&E staining. Blue staining around the circular ducts are epithelial cells and pink stain is the connective tissue. FIG. 12 shows the staining by the hydrophilic dye SRB and by the hydrophobic dye NR. The top row shows the hydrophilic dye (SRB) stained sections. The fluorescent onto and around the circles are the ducts, which can be observed at all depth of the papilla.

In the NR treated papilla sections, fluorescence is found only on the ducts and almost no fluorescence is observed in the connective tissue. This data confirms the results of the confocal microscopy indicating that hydrophilic compounds are transported into the papillae by ducts as well as the surrounding tissues, while hydrophobic compounds are transported only through the ducts.

Conclusions. This study demonstrates that the mammary papilla is an effective route for drug delivery to the breast. Agents that can be delivered include both hydrophilic and lipophilic agents. These studies show that drugs can be delivered into and across mammary papilla, and that the relative retention and transport across the mammary papilla is highly dependent on the physiochemical properties of the drug. Thus, the compositions and methods described herein can be used to provide localized prevention or treatment strategies for breast cancer.

Example 2

Santalol Induces Caspase-Dependent Apoptosis and G2/M Phase Cell Cycle Arrest in Human Breast Cancer Cells Alpha-santalol, a major component of sandalwood oil, has chemopreventive effects on skin cancer both in vitro and in vivo. This example evaluated the effects of alpha-santalol on estrogen receptor-positive (MCF-7) and estrogen receptor-negative (MDA-MB-231) human breast cancer cell lines. Additionally, mechanisms of action were also studied.

Figure 13:
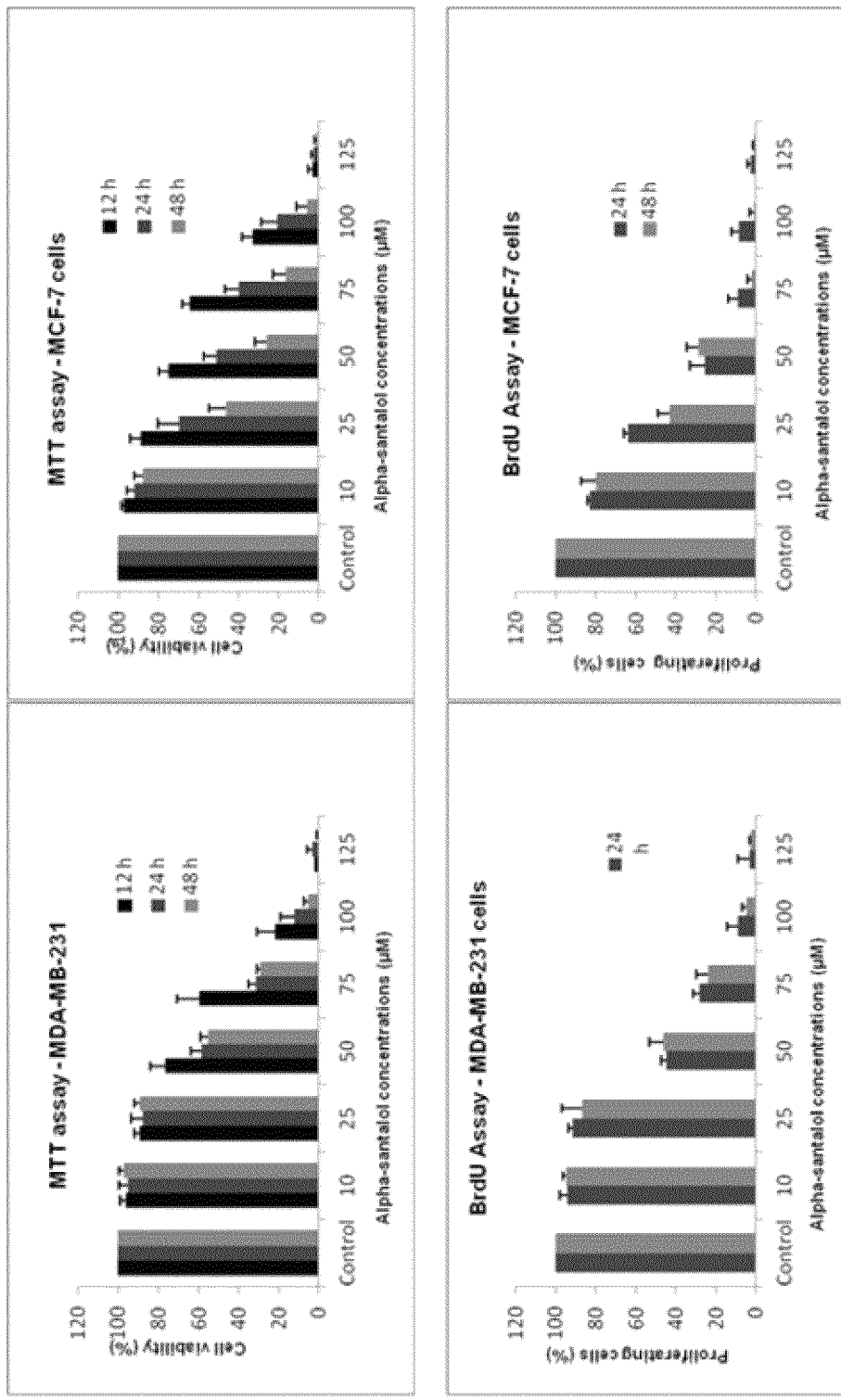
FIG. 13. Concentration and time dependent effects of alpha-santalol on cell viability and Proliferation in MDA-MB-231 and MCF-7 cells.
Figure 14:
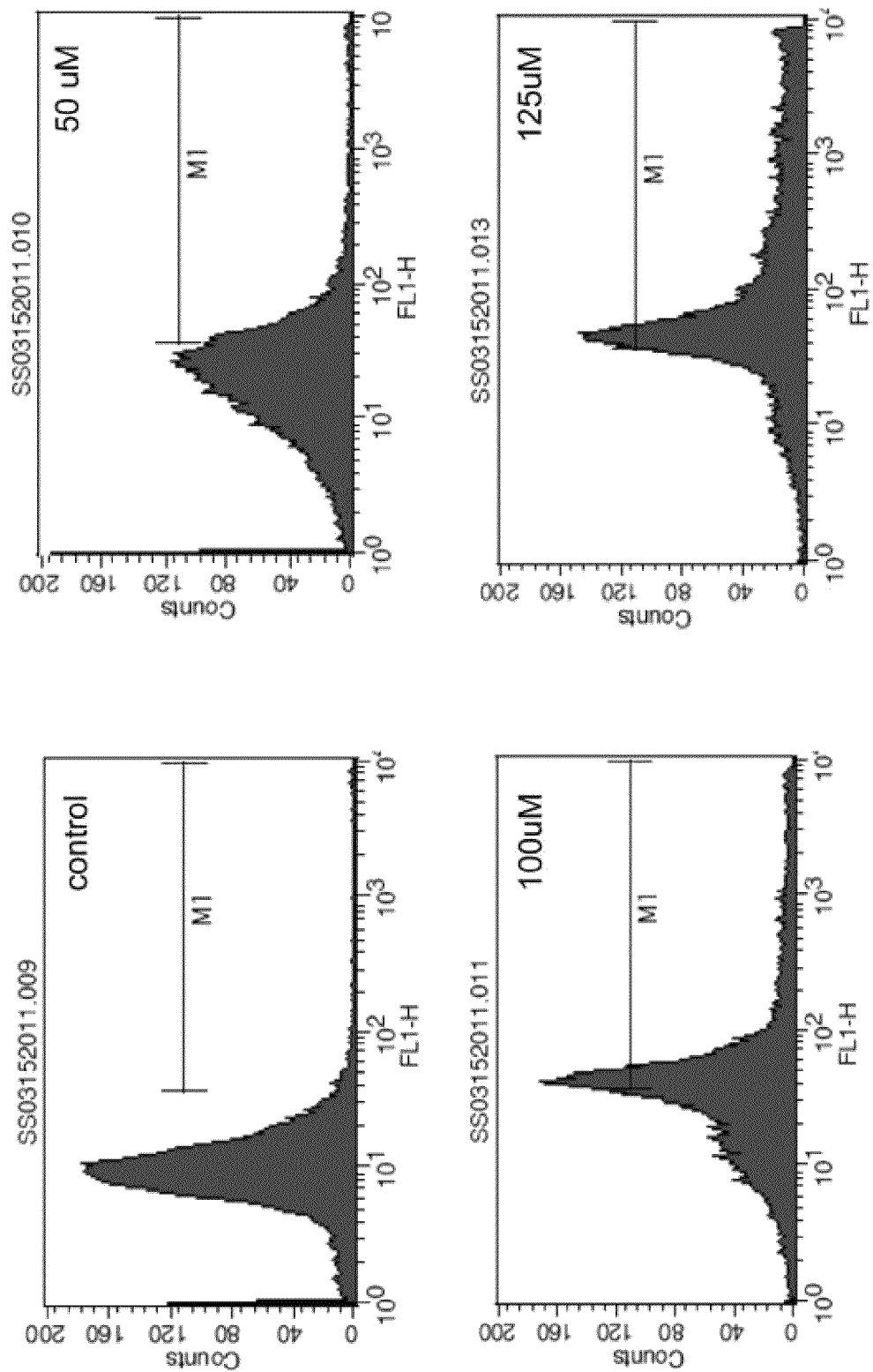
FIG. 14. Effects of alpha-santalol on DNA fragmentation by TUNEL Assay in MDA-MB-231 cells.
Figure 15:
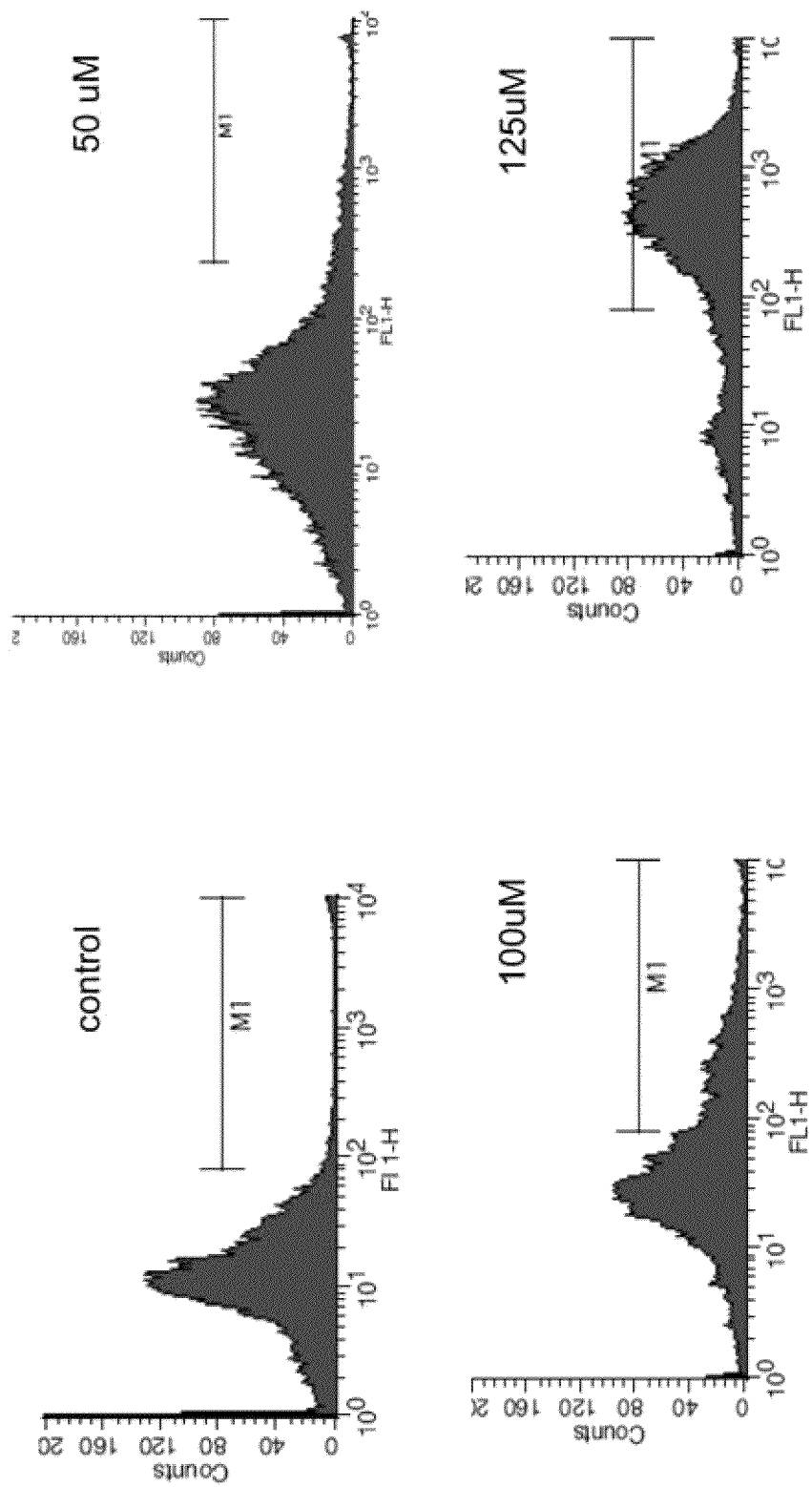
FIG. 15. Effects of alpha-santalol on DNA fragmentation by TUNEL Assay in MCF-7 cells.
Figure 16:
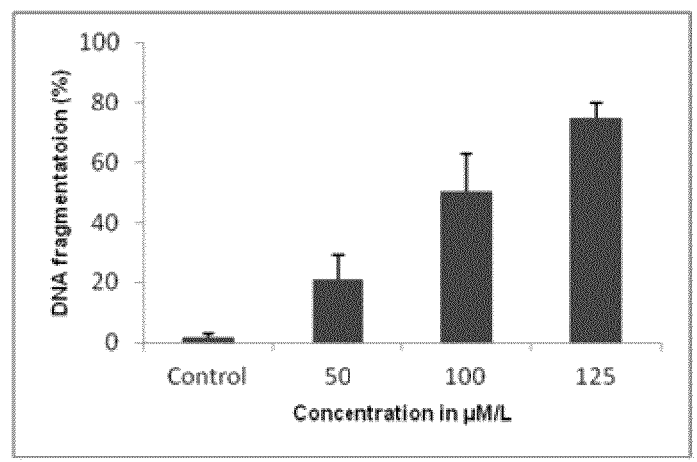
FIG. 16. Effects of alpha-santalol on DNA fragmentation by TUNEL Assay in MDA-MB-231 cells.
Figure 17:
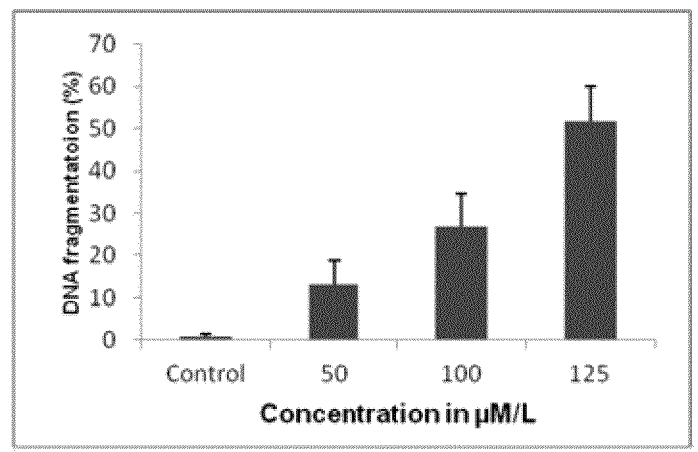
FIG. 17. Effects of alpha-santalol on DNA fragmentation by TUNEL Assay in MCF-7 cells.
Figure 18:
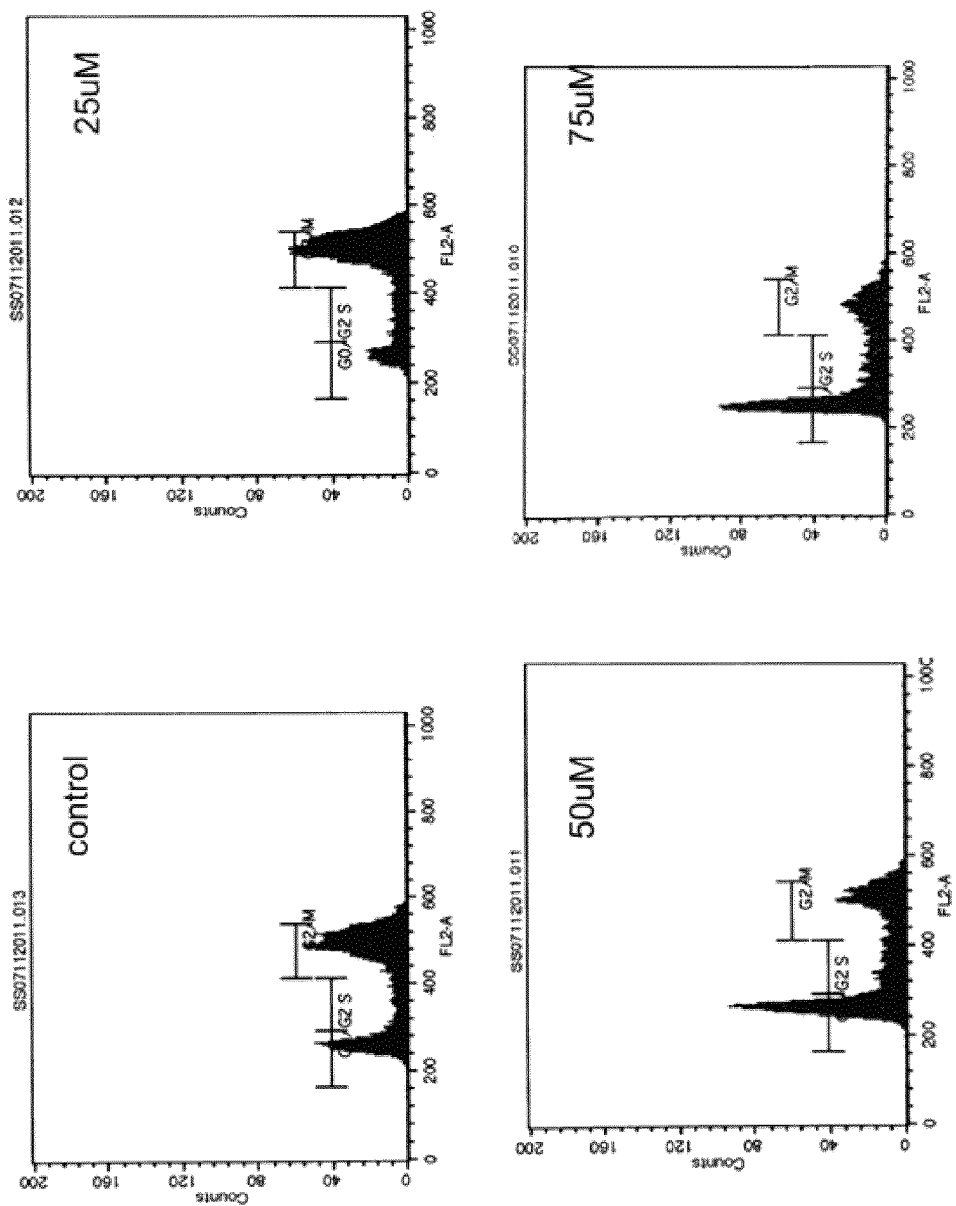
FIG. 18. Effects of alpha-santalol on the distribution of MDA-MB-231 cells in different phases of cell cycle.
Figure 19:
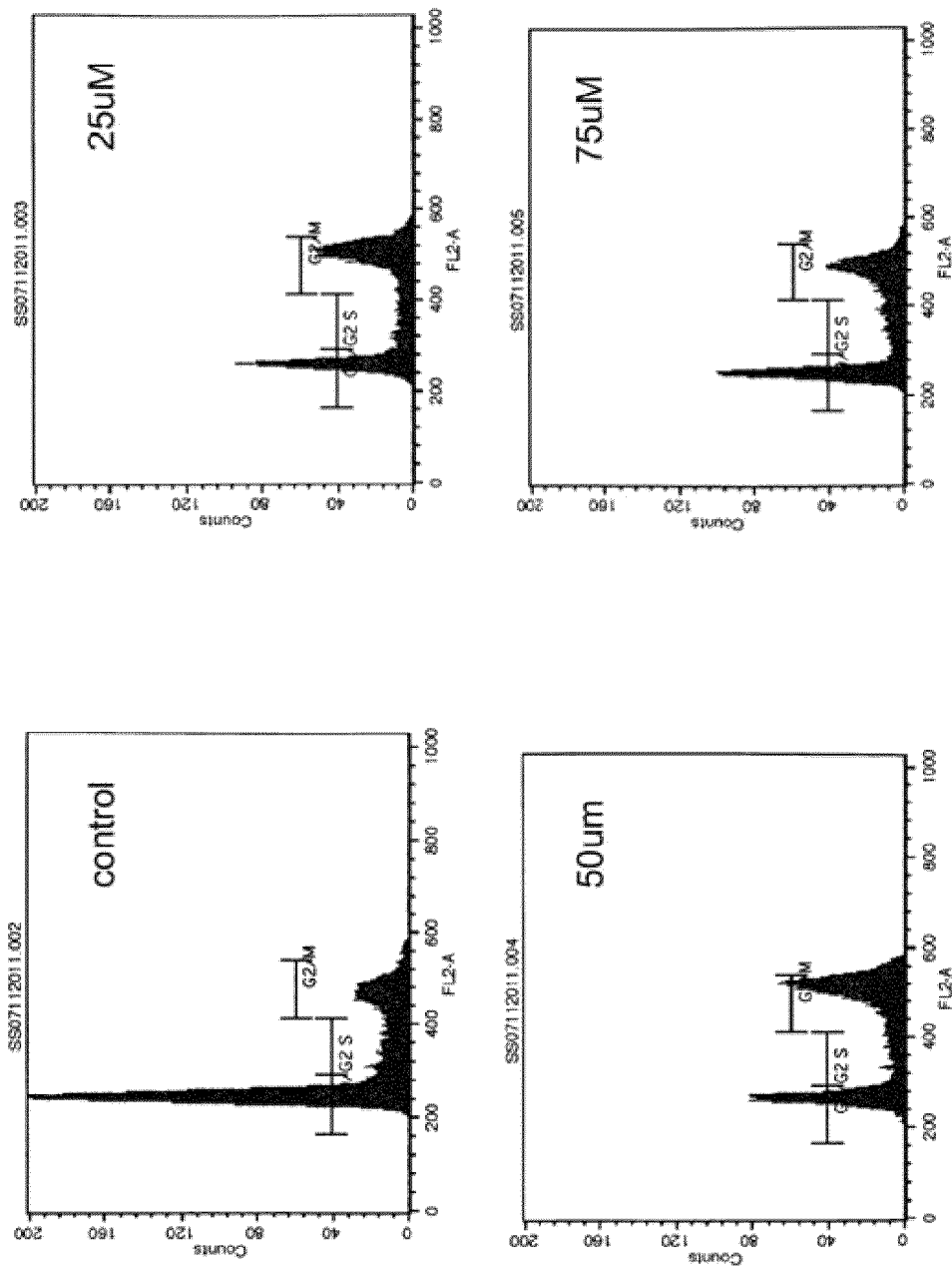
FIG. 19. Effects of alpha-santalol on the distribution of MCF-7 cells.
Figure 20:
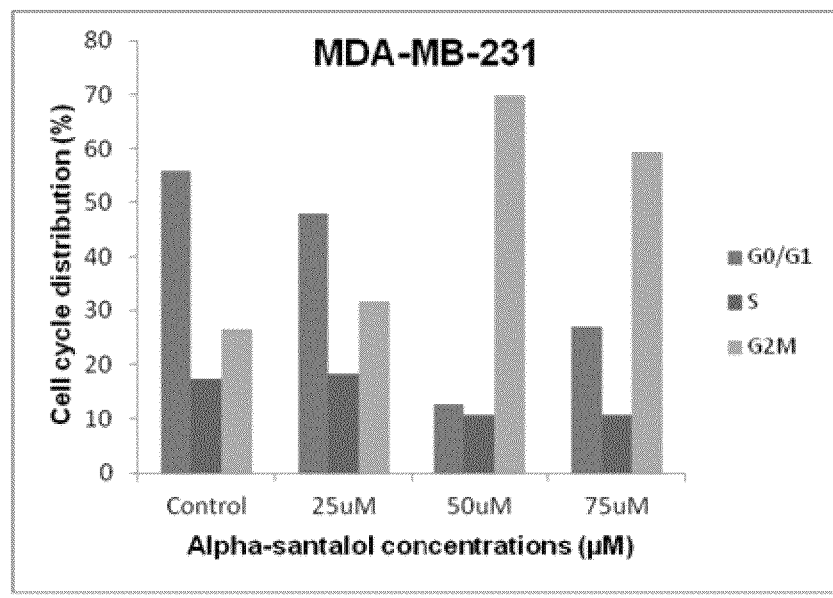
FIG. 20. Effects of alpha-santalol on the distribution of MDA-MB-231 cells in different phases of cell cycle.
Figure 21:
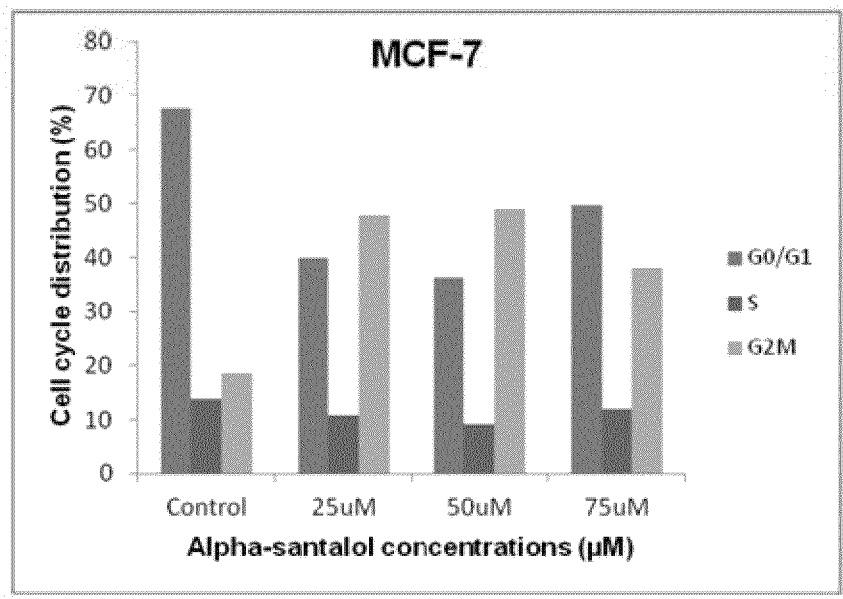
FIG. 21. Effects of alpha-santalol on the distribution of MCF-7 cells.
Figure 22:
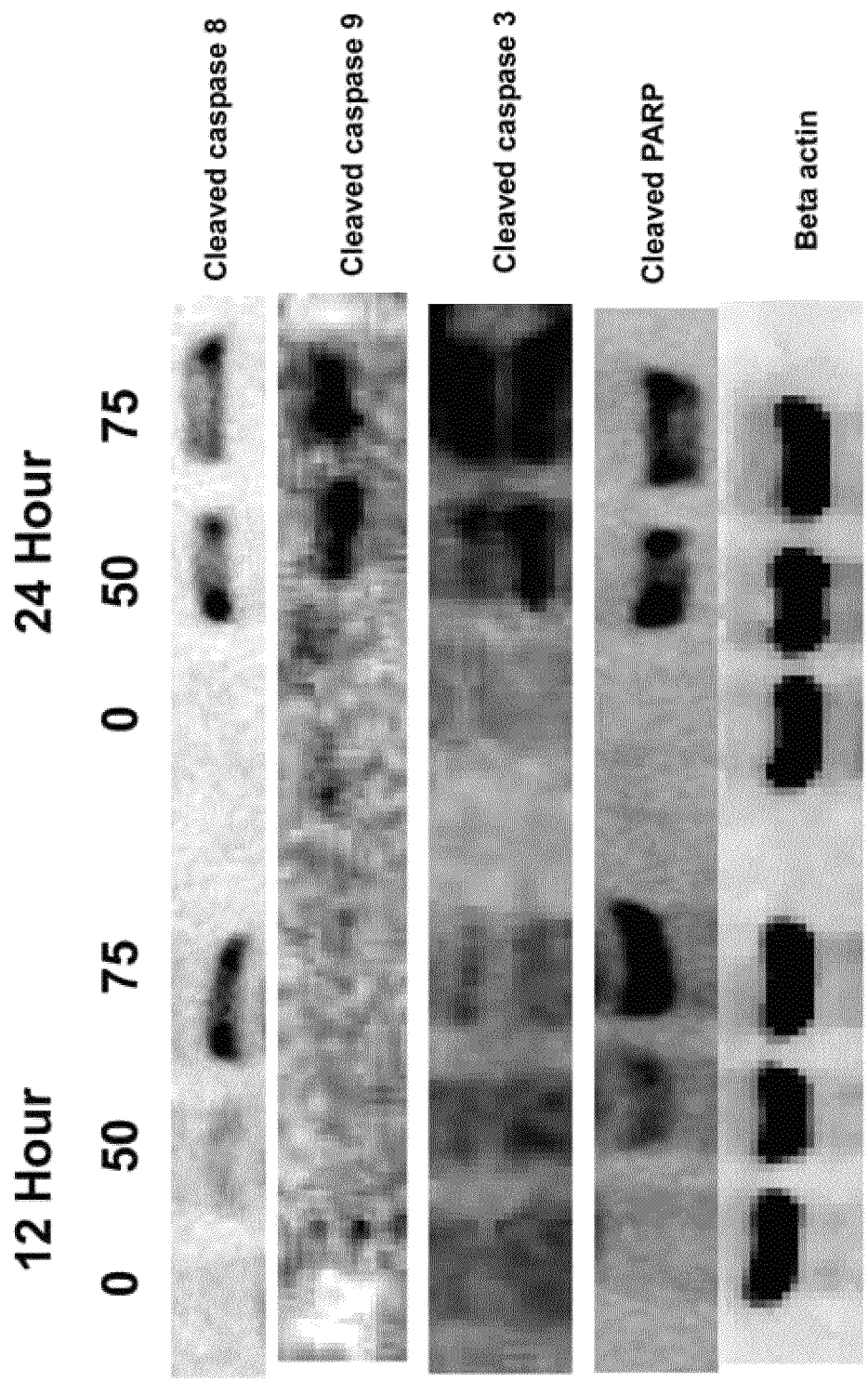
FIG. 22. Effects of alpha-santalol on apoptotic proteins MDA-MB-231 cells.
Figure 23:
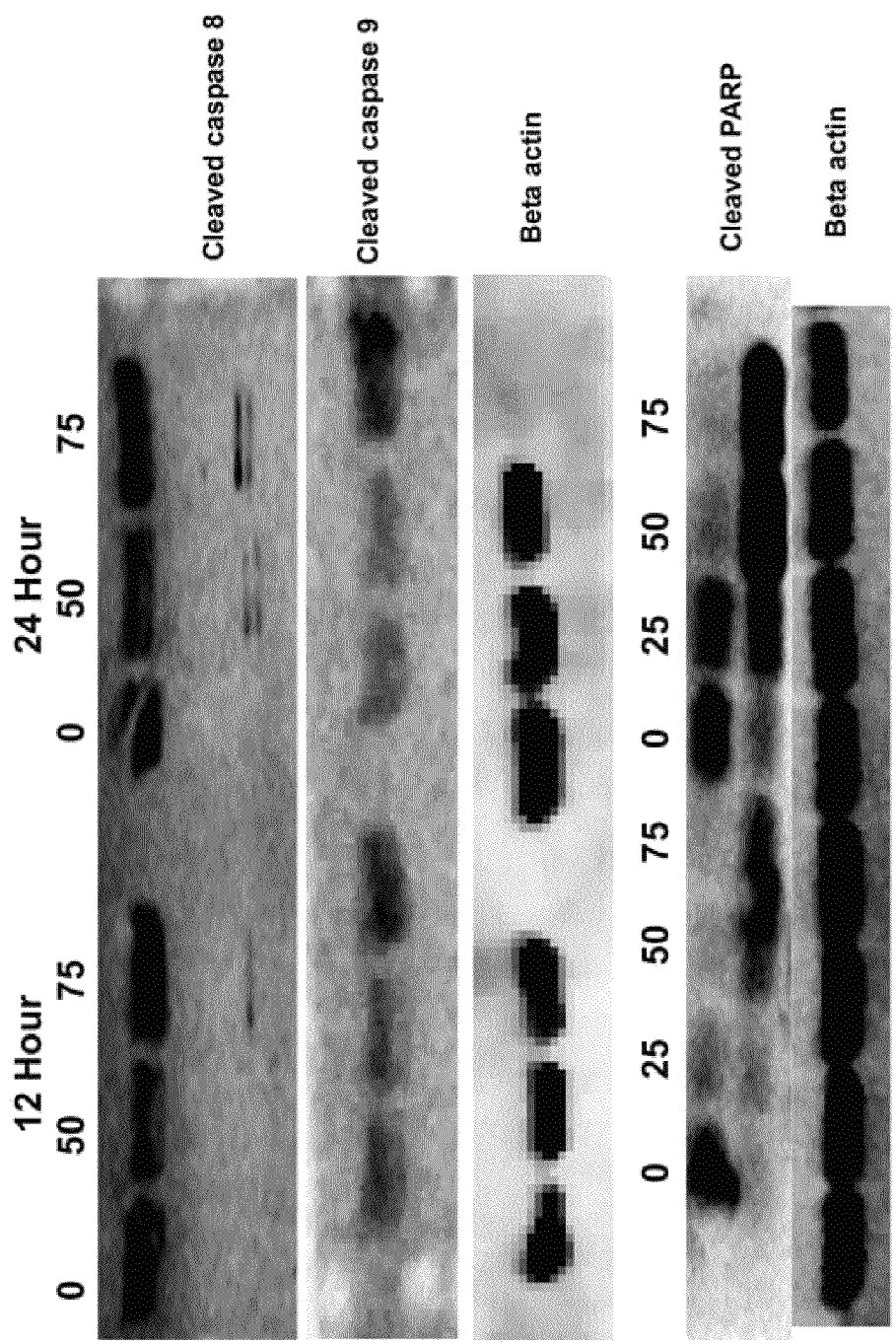
FIG. 23. Effects of alpha-santalol on apoptotic proteins MCF-7 cells.

MTT and BrdU cell proliferation ELISA showed inhibition of cell viability and proliferation in a time and dose-dependent manner in both cell lines (FIG. 13). In addition, TUNEL assay and flow cytometry results revealed that alpha-santalol significantly induced apoptosis in MCF-7 and MDA-MB-231 cells (FIGS. 14-21). Furthermore, western blot analysis of apoptotic proteins showed involvement of caspase-3, -8 and -9 in apoptotic cell death (FIGS. 22-25).

Figure 24:
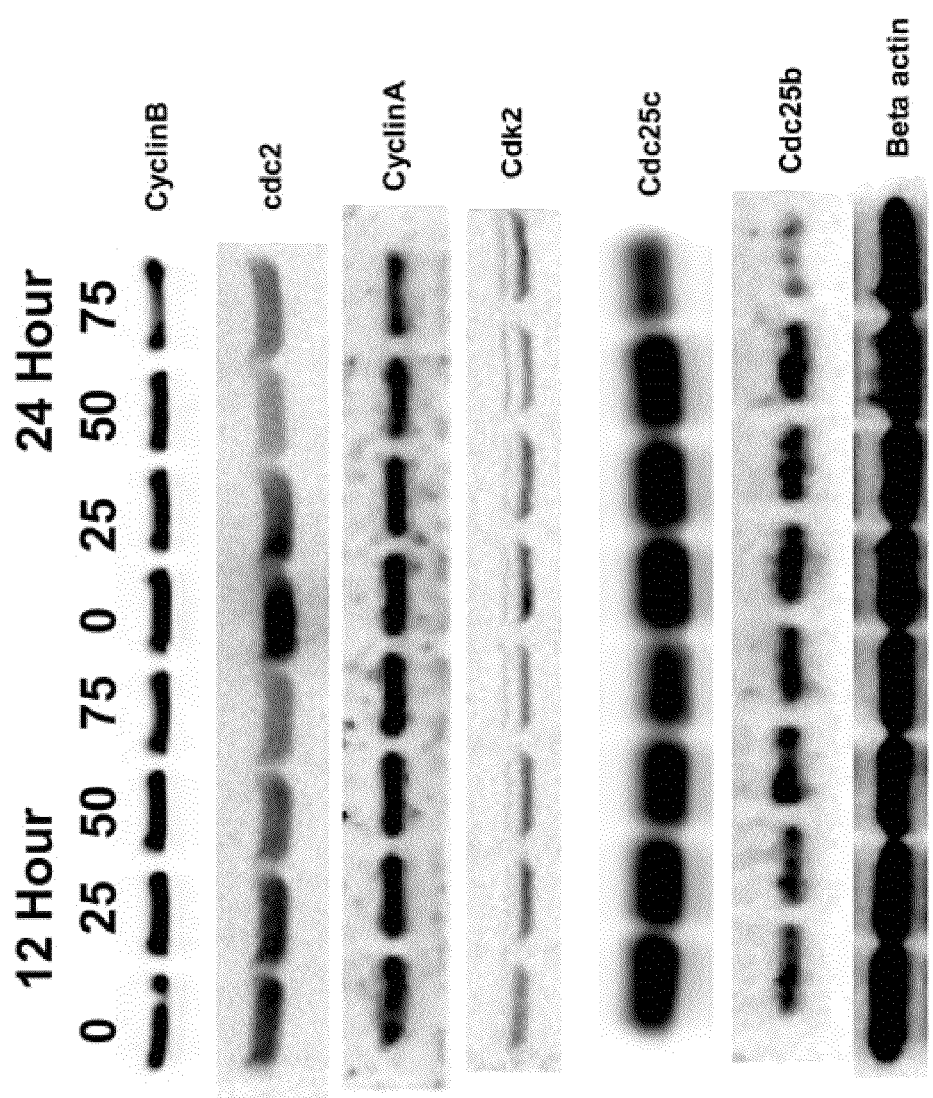
FIG. 24. Effects of alpha-santalol on cell cycle regulators in MDA-MB-231 cells.
Figure 25:
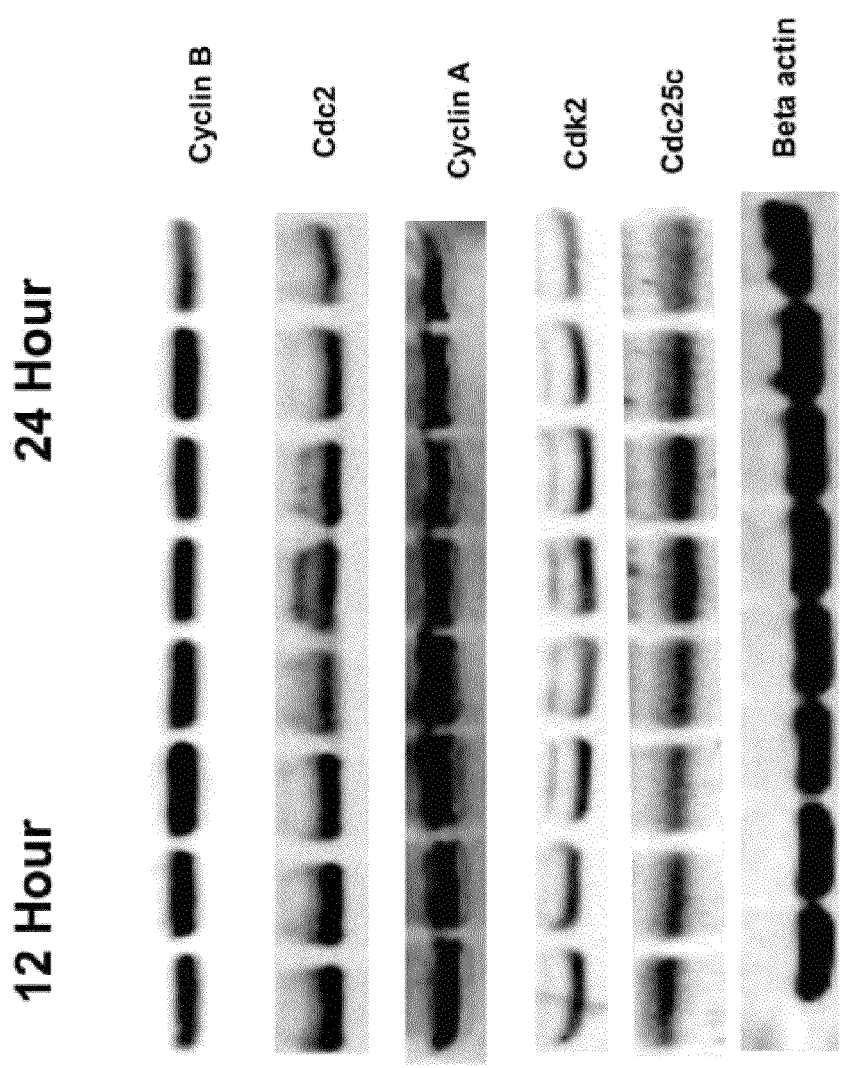
FIG. 25. Effects of alpha-santalol on cell cycle regulators in MCF-7 cells.

Induction of apoptosis by alpha-santalol was further confirmed by detecting the cleavage of PARP. Cell cycle distribution of alpha-santalol treated MCF-7 and MDA-MB-231 cells were checked by propidium iodide staining and were analyzed by flow cytometry (FIGS. 18-21). Alpha-santalol treatment arrested cell cycles at the G2/M phase 25 μM-75 μM concentrations in both cell lines. Treatment with alpha-santalol altered expressions of cell cycle proteins such as cyclin A, cyclin B1, Cdc2, Cdk2, Cdc25b, and Cdc25c (FIG. 24). Taken together, these studies provide a mechanism for the chemopreventive effect of alpha-santalol on ER-positive and ER-negative breast cancer cells through induction of apoptosis and cell cycle arrest at the G2/M phase. Alpha-santalol is therefore an effective therapeutic agent for treating and controlling breast cancer.

Materials and Methods.

MTT Assay: After treatment with different concentrations of α-santalol for different time points, cells were incubated with MTT and subsequently solubilized in DMSO. Absorbance was measured at 570 nm. See FIG. 13.

BrdU Cell Proliferation ELISA: Used to quantitate cell proliferation based on the measurement of Brdu incorporation during DNA synthesis in proliferating cells. At the end of 24 and 48 hours of treatment, cells were labeled with BrdU, fixed, denatured, and then incubated with Anti-BrdU POD. Absorbance was measured at 405 nm. See FIG. 13.

TUNEL Assay and Flow Cytometry: After incubation with alpha-santalol, cells were fixed with paraformaldehyde and ethanol. DNA strand breaks were labeled with BrdUTP. Brdu incorporation at DNA strand breaks was detected by Alexa Fluor 488 dye-labeled anti-BrdU antibodies. Samples were analyzed by Flow Cytometry. See FIGS. 14-17.

Cell Cycle Analysis: After 12 hours of treatment with alpha-santalol, cells were fixed with 70% ethanol in PBS, treated with RNaseA, followed by staining with propidium iodide. Cells were analyzed by flow cytometry to determine cell-cycle distribution. See FIGS. 18-21.

Western Blotting: Cells were treated with various concentrations of α-santalol and incubated for 12, 24 or 48 hours. Cell lysates were made and subjected to western blot analysis to determine the expression of different proteins. See FIGS. 22-25.

Conclusions. α-Santalol treatment induces time and concentration dependent growth inhibition in MDA-MB-231 and MCF-7 cells. Treatment with α-Santalol also induces time and concentration dependent apoptosis. α-Santalol treatment causes caspase-3 and PARP cleavage in MDA-MB-231 and PARP cleavage in MCF-7 cells. Apoptosis in α-santalol treated cells are mediated through the activation of caspase-8 and -9 activity in breast cancer cells. Furthermore, α-Santalol induces G2/M phase cell cycle arrest and altered the expression of proteins involved in G2/M phase transition in MCF-7 and MDA-MB-231 cells. Finally, α-Santalol is therefore an effective agent for breast cancer treatment and control.

Example 3

Transmammary Delivery of α-Santalol

A mammary papilla was set in an FSD and kept under saturation conditions for 12 hours. The solution was spiked with 4 μL $^{14}$C 5FU per ml solution. 400 μL was added to the donor cell. 7.4 PBS was added to the receptor cell. Three 40 μL samples of donor solution were taken to determine DPM of donors. 200 μL of sample was taken at each time point. After 48 hours, the mammary papilla was taken, washed, weighed and solubilized using a tissue solubilizer. After 24 hours, it was measured for DPM counts using, Cytoscint® cocktail.

TABLE 3

Experimental Design for Example 3.

| Experiment design | |
|---|---|
| Donor | 5% alpha-santalol in 2:1 ethanol:PBS (500 μL) |
| Control | No control |
| Receptor | 1:1 ethanol:PBS |
| Treatment | Drug treatment and sampling for 48 hours |
| Skin saturation | Skin was set up and kept for 6 hours with no drug in donor (only PBS) but receptor (1:1 ethanol:PBS) |
| Sampling | 200 μL sample each time |

Results.

TABLE 4

Delivery of α-Santalol.

| Mode | Lag time (hr) | Flux (μg/cm²/hr) | P (cm²/hr) | Cum. amt. permeated (μg) | DC (cm²/hr) | Cum. % Release | Tissue retention (μg/mg tissue) |
|---|---|---|---|---|---|---|---|
| 5% α-santalol in 2:1 ethanol:PBS (500 μg) | — | — | — | 109.41 (13.92) | — | 0.44 (0.05) | 8.64 (0.53) |

In this permeation study, α-santalol was found only in the receptor cell of the 48 hour sample. Previous hour samples showed non santalol in the receptor. The above shown cumulative amount permeated refers to the amount found in the 48 hour sample.

Figure 26:
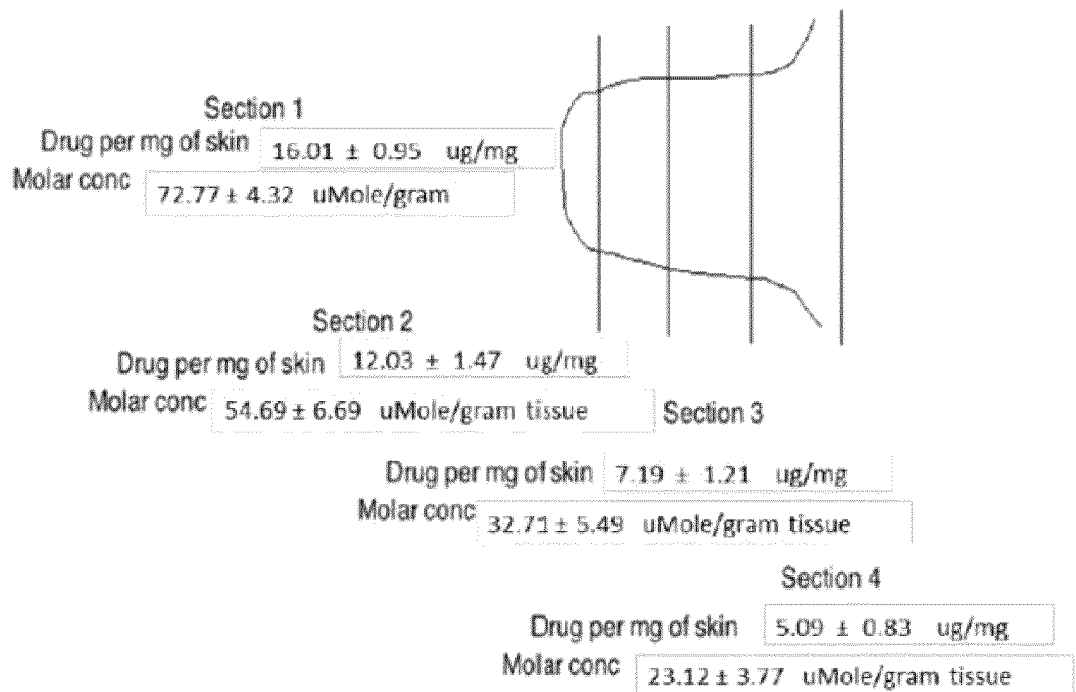
FIG. 26. An illustration of data obtained from drug retention in mammary papilla.

Drug retention at different depths of the mammary papilla is shown in FIG. 26.

Example 4

Pharmaceutical Dosage Forms

The following formulations illustrate representative pharmaceutical dosage forms that may be used for the therapeutic or prophylactic administration of an active or a composition described herein (hereinafter referred to as 'Composition X'):

TABLE 5

Compositions and Dosage Forms.

| Aerosol | mg/can | Topical Gel 1 | wt. % |
|---|---|---|---|
| Composition X | 20 | Composition X | 5% |
| Oleic Acid | 10 | Carbomer 934 | 1.25% |
| Trichloromonofluoromethane | 5,000 | Triethanoamine (pH adjusted to 5-7) | q.s. |
| Dichlorodifluoromethane | 10,000 | Methyl paraben | 0.2% |
| Dichlorotetrafluoromethane | 5,000 | Purified water | q.s. to 100 g |

| Topical Gel 2 | wt. % | Topical Ointment | wt. % |
|---|---|---|---|
| Composition X | 5% | Composition X | 5% |
| Methylcellulose | 2% | Propylene glycol | 1% |
| Methyl paraben | 0.2% | Anhydrous ointment base | 40% |
| Propyl paraben | 0.02% | Polysorbate 80 | 2% |
| Purified water | q.s. to 100 g | Methyl paraben | 0.2% |
| | | Purified water | q.s. to 100 g |

TABLE 5-continued

Compositions and Dosage Forms.

| Topical Cream 1 | wt. % | Topical Cream 2 | wt. % |
|---|---|---|---|
| Composition X | 5% | Composition X | 5% |
| White bees wax | 10% | Stearic acid | 10% |
| Liquid paraffin | 30% | Glyceryl monostearate | 3% |
| Benzyl alcohol | 5% | Polyoxyethylene stearyl ether | 3% |
| Purified water | q.s. to 100 g | Sorbitol | 5% |
| | | Isopropyl palmitate | 2% |
| | | Methyl paraben | 0.2% |
| | | Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Composition X'. Aerosol formulation (i) may be used in conjunction with a standard, metered dose aerosol dispenser. Additionally, the specific ingredients and proportions are for illustrative purposes. Additionally, the specific ingredients and proportions are for illustrative purposes. Ingredients may be exchanged for suitable equivalents and proportions may be varied, according to the desired properties of the dosage form of interest.

Example 5

Various Novel Formulation and Device Design for Transmammary Drug Delivery

Figure 27:
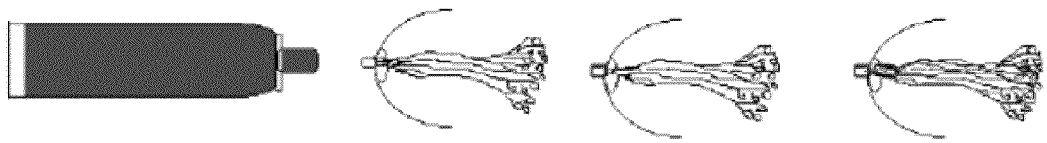
FIG. 27. Examples of various formulations and devices for transmammary drug deliver.
Figure 27:
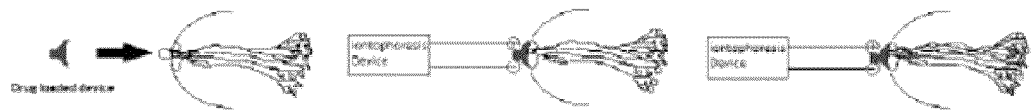
Figure 27:
Figure 27:
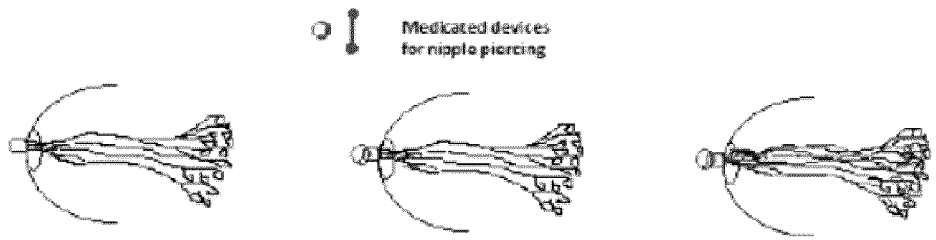
Figure 27:
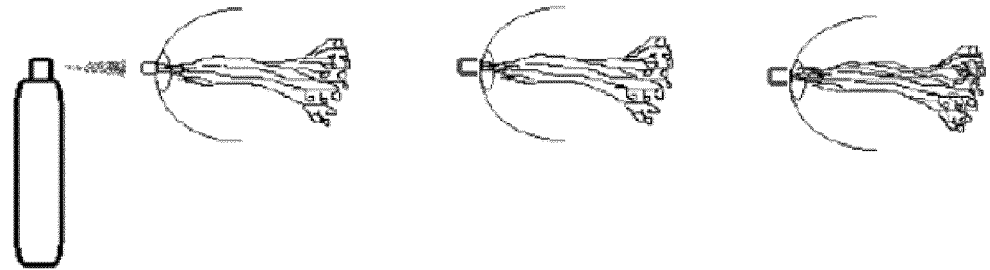
Figure 27:
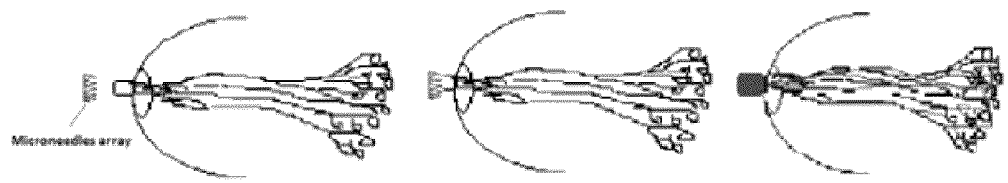
Figure 27:
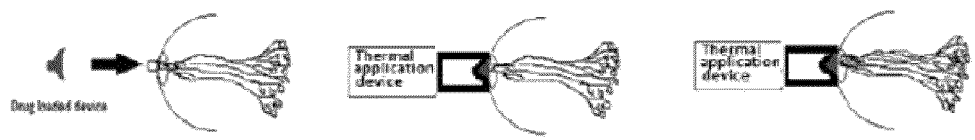
Figure 27:
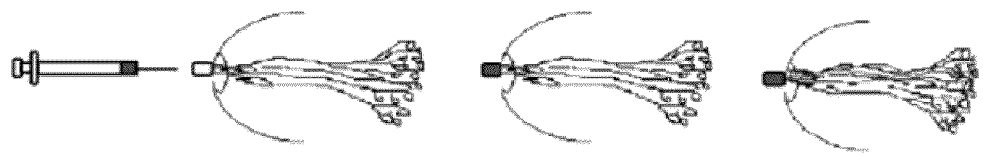
Figure 27:
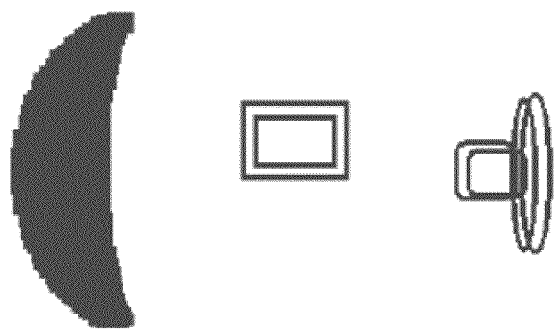
Figure 27:
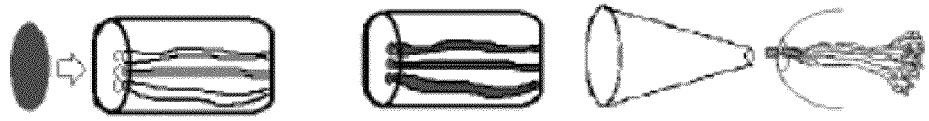

Examples of various formulations and devices for transmammary drug deliver are shown in FIG. 27. Examples of such compositions include creams, gels, thermo-reversible gels, ointments, aerosol sprays, medicated pads, patches or nipple shields, and keratin plugs. Methods of delivering the compositions described herein include topically applying the aforementioned compositions, alone or in combination with heat, iontophoresis, medicated devices for physical permeation enhancement, medicated devices for nipple piercing, and/or microneedle based drug delivery methods.

Example 6

Removal of the Keratin Plug from the Surface of Human and Porcine Mammary Papilla Background Keratin plug sits on the top of the mammary papilla at duct openings to prevent entry of microorganism from the outer environment. Number of keratin plug may depend on the number of duct openings on the surface of mammary papilla. So in human there might be 7-10 duct openings and thus 7-10 keratin plugs while in porcine it could be 2-3 keratin plugs as reports suggest that there are 2-3 duct openings on the surface of mammary papilla in pigs.

Procedure

Keratin plug was removed from human and porcine mammary papilla using an alcoholic cotton swab. The swab was gently rubbed on the surface of the mammary papilla. The mammary papilla was observed under the microscope to confirm the removal of the plug from the surface and to confirm that epidermis of the mammary papilla was not damaged during this procedure.

Results

Figure 28:
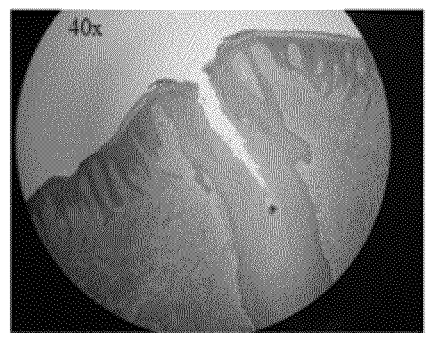
FIG. 28. Microscopic image of a section of porcine mammary papilla after removal of the keratin plug (40×).
Figure 29:
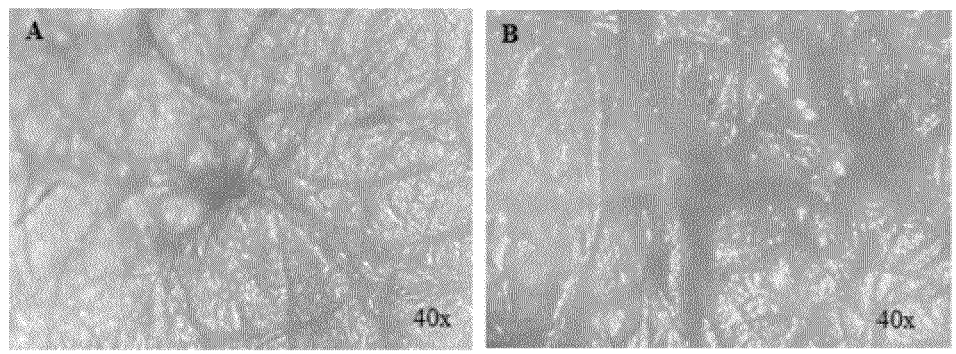
FIG. 29. Microscopic images of human mammary papilla with keratin plug removal (A) and without keratin plug removal (B) (40×).

Images showing removal of keratin plug upon mild squeezing and gentle wiping with ethanolic cotton swab (see FIGS. 28 and 29).

Experiment 7

Transmammary Permeation of 5FU across Porcine Mammary Papilla with and without Removal of the Keratin Plug

TABLE 6

Experimental design for Experiment 7.

| Experiment design | |
|---|---|
| Treatment | 20 mg/ml 5FU (500 µl) in 50:50 of ethanol:water spiked with C14 5FU-permeation of 5FU across porcine mammary papilla with keratin plugs removed |
| Control | Permeation of above across porcine mammary papilla without keratin plug removal |
| Receptor | 7.4 pH PBS with 0.05% w/v sodium azide |
| Skin saturation | Tissue was set up and kept for 12 hours with no donor but receptor |
| Sampling | 200 µl sample each time |

Experimental Procedure

Figure 30:
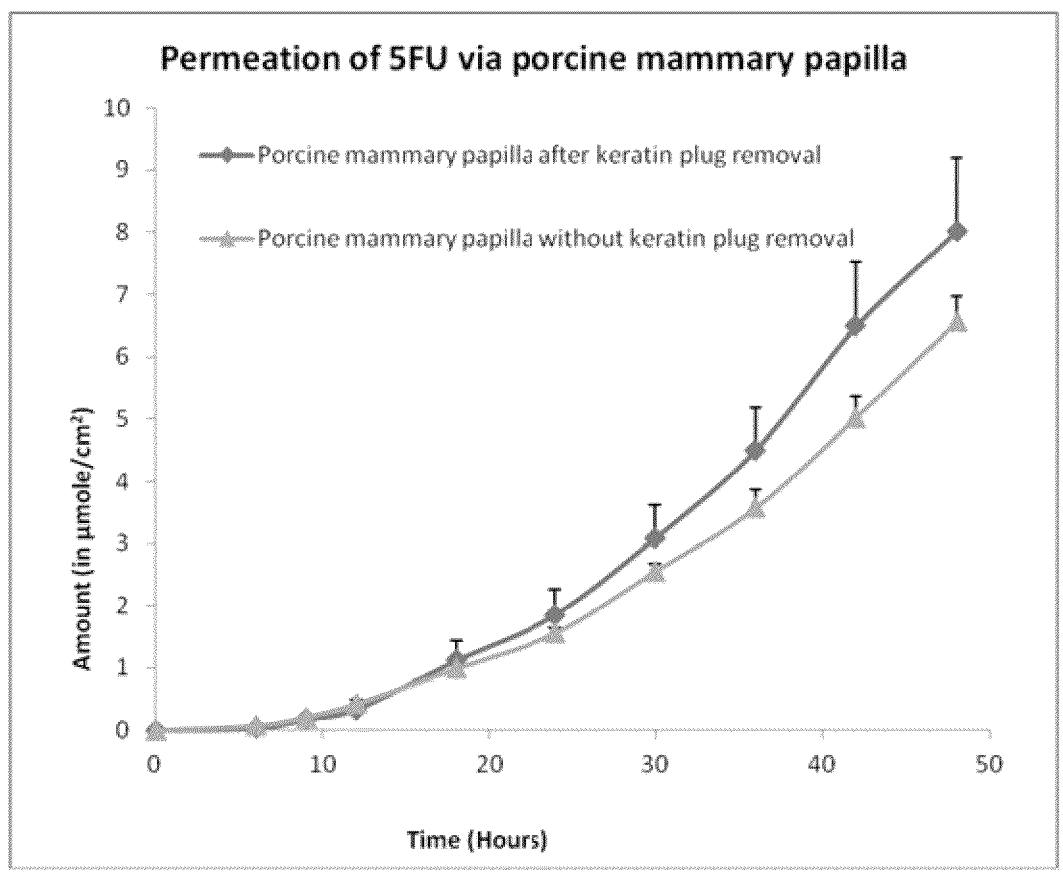
FIG. 30. 5FU permeation across porcine mammary papilla with and without removal of the keratin plug. Each point represented as mean±SEM (n=4).

Tissues were set in FDC and kept for saturation for 12 hours. The drug solutions were spiked with radioactive substances. Now 500 µl of the formulation was placed in the donor. Receptor medium was PBS with 7.4 pH. Three 400 µl samples of donor were taken to determine DPM of donors. 200 µl samples were taken from the receptor at pre-determined time points. At the end of 48 hours, tissues were taken, washed, weighed and solubilized using the tissue solubilizer (0.5 M Q ammonium hydroxide in toluene). After 24 hours, it was measured for DPM counts using Cytoscint® cocktail. Results can be seen in FIG. 30.

Conclusion:

This study suggests that upon removal of the keratin plugs, permeation of 5 FU increases slightly, though statistically not significant.

Experiment 8

Transmammary Permeation of Estradiol (EST) Across Porcine Mammary Papilla with and without Removal of the Keratin Plug

TABLE 7

Experimental Design for Experiment 8.

| Experiment design | |
|---|---|
| Treatment | 15 mg/ml EST (500 µl) in 50:50 of ethanol:water spiked with 3H EST-permeation of EST across porcine mammary papilla with keratin plugs removed |
| Control | Permeation of above across porcine mammary papilla without keratin plug removal |
| Receptor | 7.4 pH PBS (with 0.05% w/v sodium azide):ethanol (80:20) |
| Skin saturation | Tissue was set up and kept for 12 hours with no donor but receptor |
| Sampling | 200 µl sample each time |

Experimental Procedure

Figure 31:
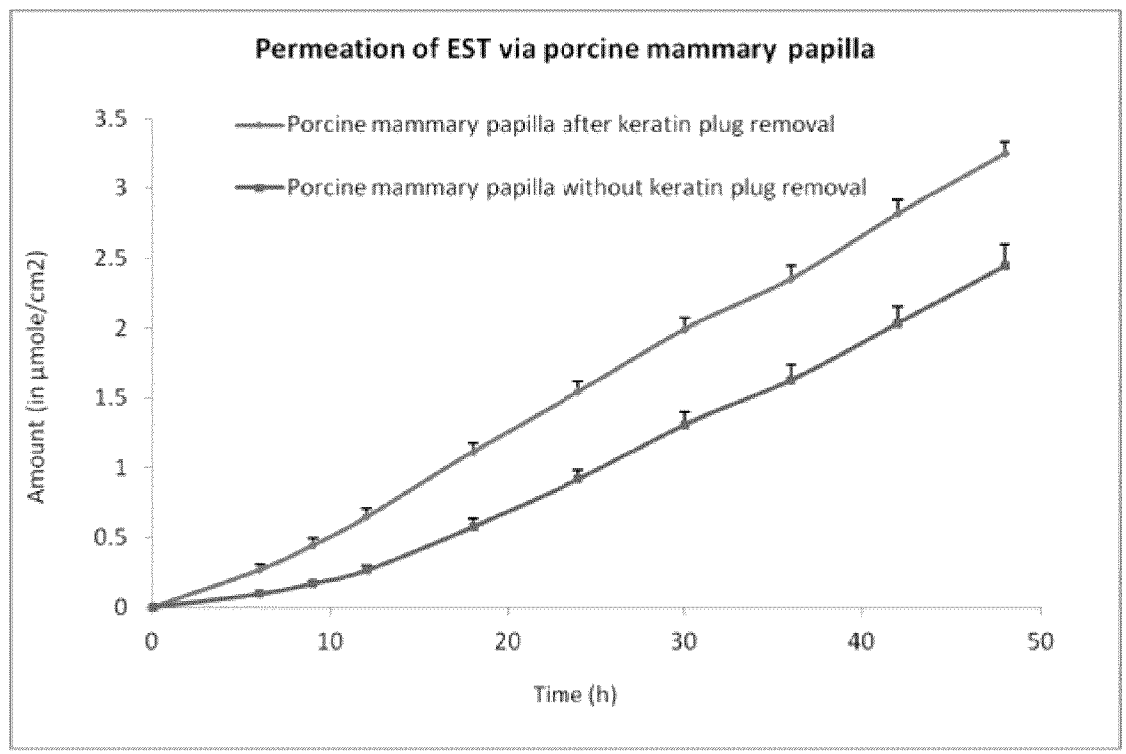
FIG. 31. EST permeation across porcine mammary papilla with and without removal of the keratin plug. Each point represented as mean±SEM (n=4).

Mammary papillae tissues were thawed. Keratin plugs were removed from the mammary papilla tissues using swabs with ethanol. Tissues were set in FDC and kept for saturation for 12 hours. The drug solutions were spiked with radioactive substances. Now 500 µl of the formulation was placed in the donor. Receptor medium was PBS with 7.4 pH. Three 400 µl samples of donor were taken to determine DPM of donors. 200 µl samples were taken from the receptor at pre-determined time points. At the end of 48 hours, tissues were taken, washed, weighed and solubilized using the tissue solubilizer (0.5 M Q ammonium hydroxide in toluene). After 24 hours, it was measured for DPM counts using, Cytoscint® cocktail. Results can be seen in FIG. 31.

Conclusion:

This study suggests that upon removal of the keratin plugs, permeation of EST increases significantly.

Experiment 9

Transmammary Permeation of Dextran (10,000 Da) Across Porcine Mammary Papilla with and without Removal of the Keratin Plug

TABLE 8

Experimental Design for Experiment 9.

| Experiment design | |
|---|---|
| Treatment | 10 mg/ml dextran (500 µl) in 50:50 of ethanol:water spiked with C14 dextran-permeation of dextran across porcine mammary papilla with keratin plugs removed |
| Control | Permeation of above across porcine mammary papilla without keratin plug removal |
| Receptor | 7.4 pH PBS with 0.05% w/v sodium azide |
| Skin saturation | Tissue was set up and kept for 12 hours with no donor but receptor |
| Sampling | 200 µl sample each time |

Experimental Procedure

Figure 32:
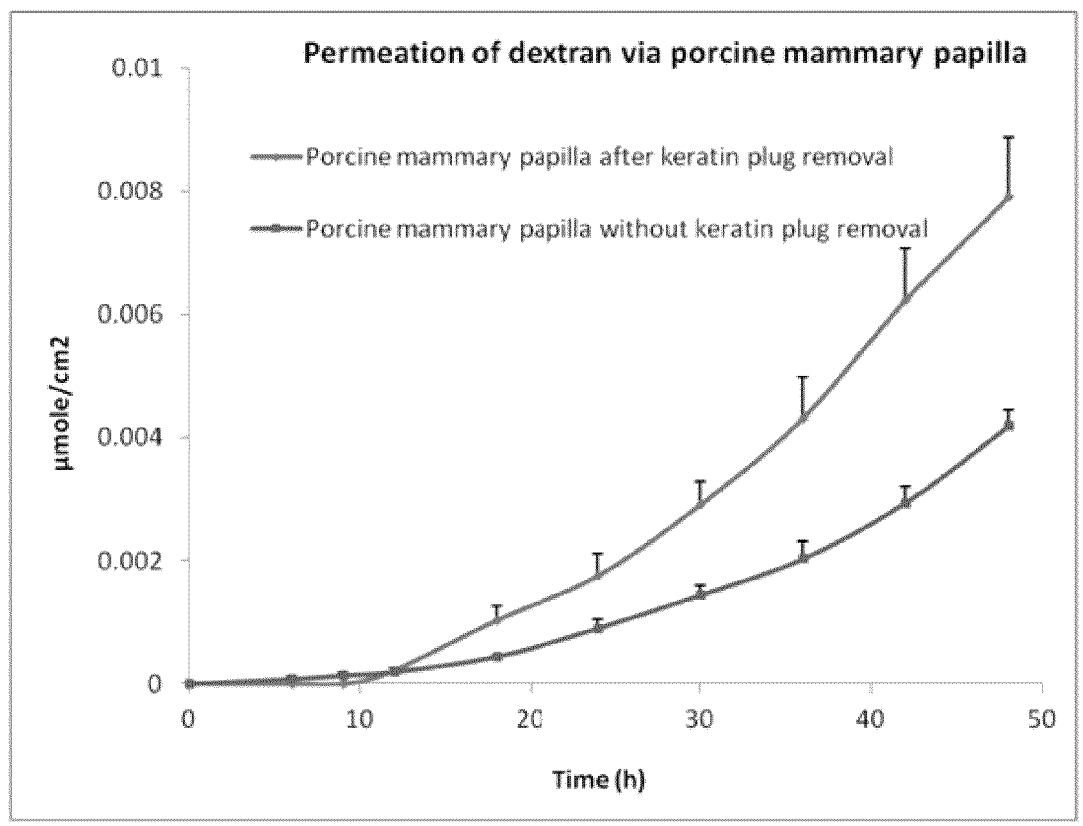
FIG. 32. Shows dextran permeation across porcine mammary papilla with and without removal of the keratin plugs. Each data point is represented as mean±SEM, n=4.

Mammary papillae tissues were thawed. Keratin plugs were removed from the mammary papilla tissues using swabs with ethanol. Tissues were set in FDC and kept for saturation for 12 hours. The drug solutions were spiked with radioactive substances. Now 500 µl of the formulation was placed in the donor. Receptor medium was PBS with 7.4 pH. Three 400 µl samples of donor were taken to determine DPM of donors. 200 µl samples were taken from the receptor at pre-determined time points. At the end of 48 hours, tissues were taken, washed, weighed and solubilized using the tissue solubilizer (0.5 M Q ammonium hydroxide in toluene). After 24 hours, it was measured for DPM counts using, Cytoscint® cocktail. Results can be seen in FIG. 32.

Conclusion:

This study suggests that dextran can be delivered via porcine mammary papilla. Keratin plug plays an important role in the permeation of dextran. Removal of the keratin plugs from the surface of the mammary papilla induces approximately 2 folds increase in the permeation of dextran across the tissues.

Experiment 10

Permeation of Inulin (5000 Da) Across Porcine Mammary Papilla after Removal of the Keratin Plug

TABLE 9

Experimental Design for Experiment 10.

| Experiment design | |
|---|---|
| Donor | 10 mg/ml 5FU (500 µl) in 50:50 ethanol:water spiked with C14 Inulin |
| Control | No control experiment |
| Receptor | 7.4 pH PBS with 0.05% w/v sodium azide |
| Skin saturation | Skin was set up and kept for 12 hours with no donor but receptor |
| Sampling | 200 µl sample each time |

Experimental Procedure

Figure 33:
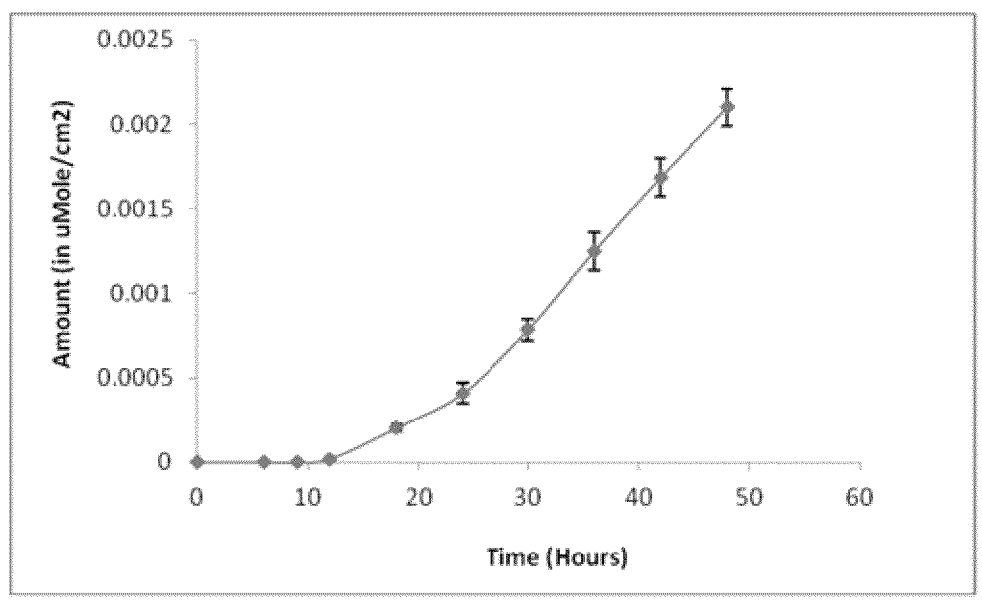
FIG. 33. Shows a tissue permeation profile for Inulin. Each data point is represented as mean±SEM, n=4.
Figure 34:
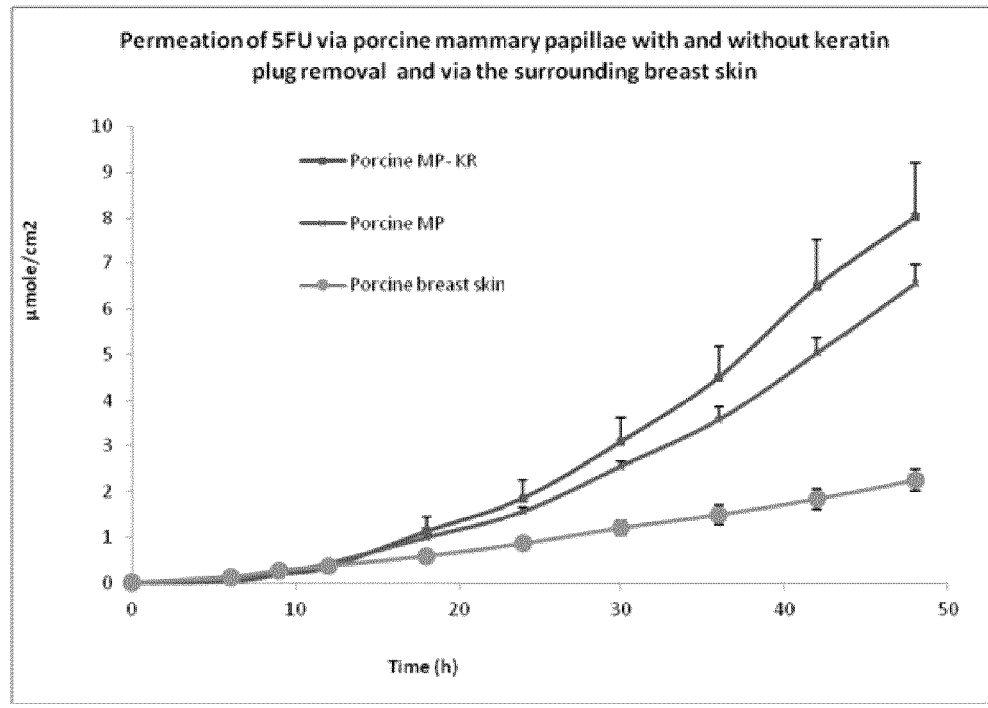
FIG. 34. Permeation of 5FU via porcine mammary papillae with and without keratin plug removal and via the surrounding breast skin. Each data point is represented as mean±SEM, n=4 (Porcine MP-KR is porcine mammary papilla after keratin plug removal; Porcine MP is porcine mammary papilla without keratin plug removal).
Figure 35:
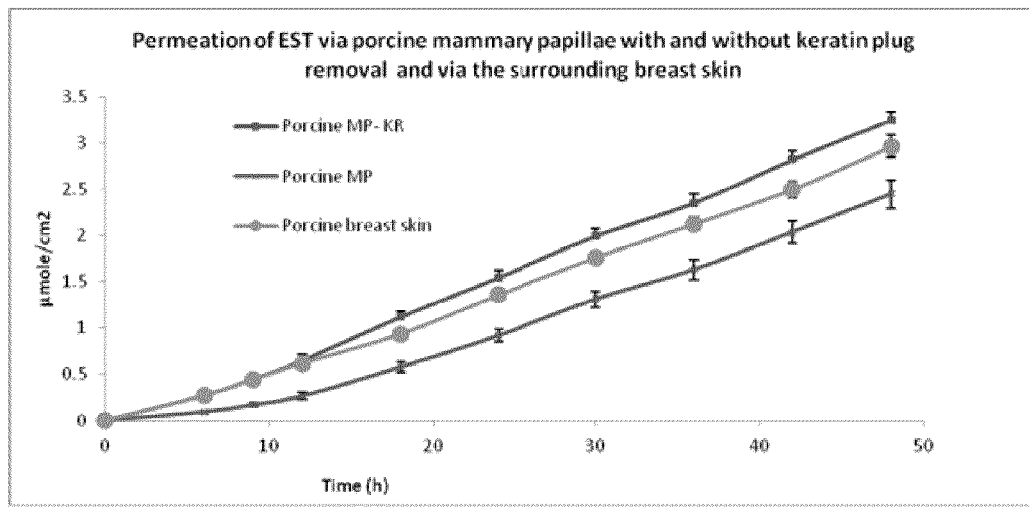
FIG. 35. Permeation of EST via porcine mammary papillae with and without keratin plug removal and via the surrounding breast skin. Each data point is represented as mean±SEM, n=4 (Porcine MP-KR is porcine mammary papilla after keratin plug removal; Porcine MP is porcine mammary papilla without keratin plug removal).
Figure 36:
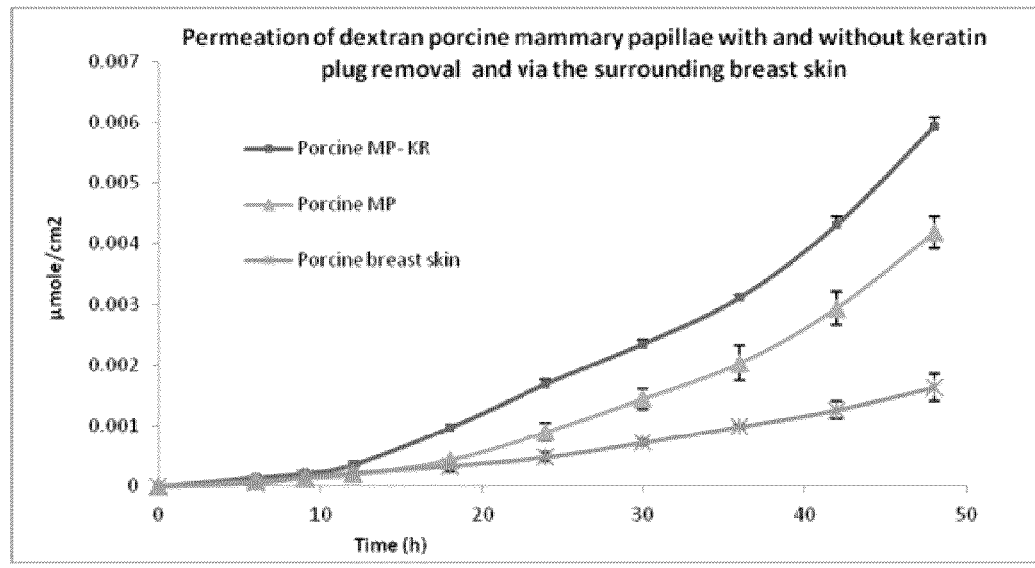
FIG. 36. Permeation of dextran via porcine mammary papillae with and without keratin plug removal and via the surrounding breast skin. Each data point is represented as mean±SEM, n=4 (Porcine MP-KR is porcine mammary papilla after keratin plug removal; Porcine MP is porcine mammary papilla without keratin plug removal).
Figure 37:
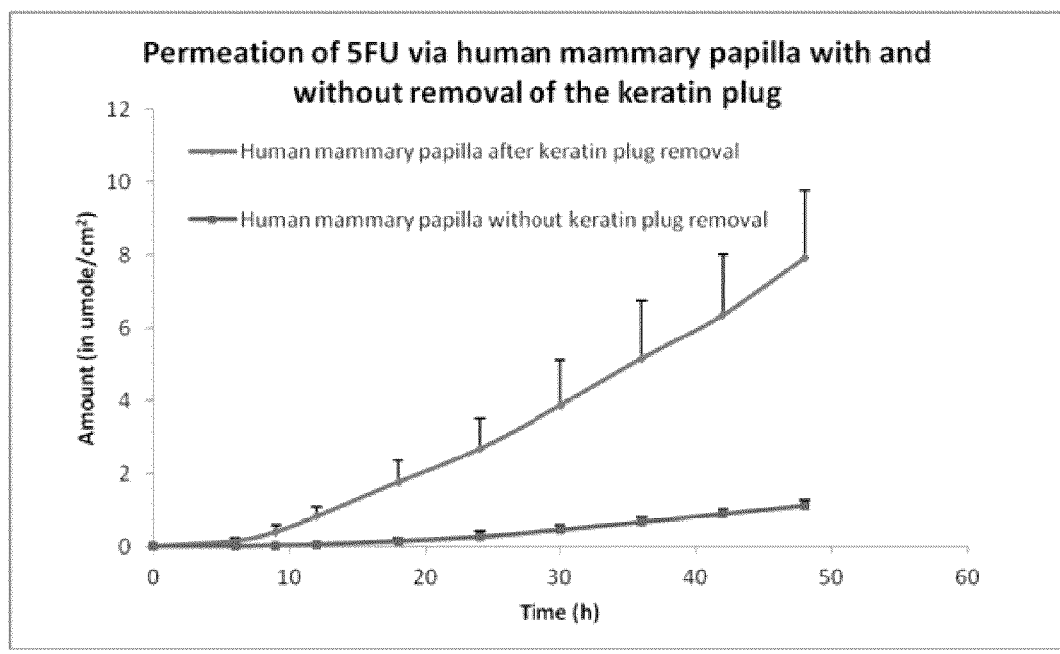
FIG. 37. 5FU permeation across human mammary papilla with and without removal of the keratin plug. Each data point is represent as mean±SEM, n=3.

Mammary papillae tissues were thawed. Keratin plugs were removed from the mammary papilla tissues using swabs with ethanol. Tissues were set in FSD and kept for saturation for 12 hours. The drug solutions were spike with radioactive substances. Now 500 µl of the formulation was placed in the donor. Receptor medium was PBS with 7.4 pH. Three 400 µl samples of donor were taken to determine DPM of donors. 200 µl samples were taken from the receptor at pre-determined time points. At the end of 48 hours, tissues were taken, washed, weighed and solubilized using the tissue solubilizer (0.5 M Q ammonium hydroxide in toluene). After 24 hours, it was measured for DPM counts using, Cytoscint® cocktail. Results can be seen in FIG. 33.

TABLE 10

Drug permeation and retention parameters

| lag time (hr) | Flux (µmole/sq.cm/hr) | cumulative amt. permeated (µmole) | Drug permeation (% of applied dose) | Skin retention (µmole/g of tissue) | Total drug retention in tissue (umole) | Drug retention in tissue (% of applied dose) |
|---|---|---|---|---|---|---|
| 16.78 | 0.000066 | 0.0037 | 0.37 | 0.023 | 0.0083 | 0.83 |
| (1.65) | (0.000006) | (0.0002) | (0.02) | (0.002) | (0.0009) | (0.09) |

Values in parentheses are SEM, n = 4

Discussion:

The results show that inulin could permeate across the porcine mammary papilla. Inulin showed higher lag time (16.7 h) as compared to the small hydrophilic molecule, 5FU (130 Da). In total 18.37 μg of inulin permeated across the tissue at the end of 48 hours which is 0.37% of the dose applied into the donor. The transmammary flux of inulin was 0.33 μg/sq·cm/h which is significantly lesser than the flux of 5FU (10.79 μg/sq·cm/h). This indicated that the transport of macromolecule via mammary papilla is obstructed depending on the size of the molecule. At last, amount of inulin retaining into the tissue was determined. Here total 41.28 μg inulin was found to be retaining into the tissue which is 0.83% of the dose applied over the tissue into the donor chamber.

Conclusion this study suggests that the hydrophilic macromolecules inulin, with size of 5000 Da, can be delivered via mammary papilla. However, the flux of the inulin permeation was found to significantly lower than that of a small hydrophilic molecule 5FU.

Experiment 11

Transdermal Permeation of 5FU, EST and Dextran (10 kDa) Across Porcine Breast Skin (Skin Surrounding Mammary Papillae; it can be Called Abdominal Skin as Well)

TABLE 11

Experimental Design for Experiment 11.

| Experiment design | |
|---|---|
| Treatment | 20 mg/ml 5FU, 15 mg/ml EST and 10 mg/ml dextran (500 μl) in 50:50 of ethanol:water spiked with radioactive compounds to study permeation via porcine breast skin |
| Receptor | 7.4 pH PBS with 0.05% w/v sodium azide or 80:20 of PBS:ethanol |
| Tissue saturation | Tissue was set up and kept for 12 hours with no donor but receptor |
| Sampling | 200 μl sample each time |

Experimental Procedure

Porcine breast skin surrounding mammary papillae was collected and prepared using scalpel or dermatome to remove the underlying fat. Tissues were set in FDC and kept for saturation for 12 hours. The drug solutions were spiked with radioactive substances. Now 500 μl of the formulation was placed in the donor. Receptor medium was PBS with 7.4 pH or 80:20 of PBS:ethanol. Samples of donor were taken in triplicates to determine DPM of donors. 200 μl samples were taken from the receptor at pre-determined time points. At the end of 48 hours, tissues were taken, washed, weighed and solubilized using the tissue solubilizer (0.5 M Q ammonium hydroxide in toluene). After 24 hours, it was measured for DPM counts using, Cytoscint® cocktail. Results can be seen in FIGS. 34-37.

Discussion

Above results suggest that compounds show significantly higher permeation via porcine mammary papilla than porcine breast skin.

Conclusion:

Mammary papilla is a potential route of transport and it has higher permeability for drugs in comparison to the surrounding breast skin, especially for hydrophilic compounds.

Experiment 12

Transmammary Permeation of 5FU Across Human Mammary Papilla with and without Removal of the Keratin Plug

TABLE 12

Experimental Design for Experiment 12.

| Experiment Design | |
|---|---|
| Treatment | 20 mg/ml 5FU (500 μl) in 50:50 of ethanol:water spiked with C14 5FU-permeation of 5FU across human mammary papilla with keratin plugs removed |
| Control | Permeation of above across human mammary papilla without keratin plug removal |
| Receptor | 7.4 pH PBS with 0.05% w/v sodium azide |
| Skin saturation | Tissue was set up and kept for 12 hours with no donor but receptor |
| Sampling | 200 μl sample each time |

Experimental Procedure

Mammary papillae tissues were thawed. Keratin plugs were removed from the mammary papilla tissues using swabs with ethanol. Tissues were set in FDC and kept for saturation for 12 hours. The drug solutions were spiked with radioactive substances. Now 500 μl of the formulation was placed in the donor. Receptor medium was PBS with 7.4 pH. Three 400 μl samples of donor were taken to determine DPM of donors. 200 μl samples were taken from the receptor at pre-determined time points. At the end of 48 hours, tissues were taken, washed, weighed and solubilized using the tissue solubilizer (0.5 M Q ammonium hydroxide in toluene). After 24 hours, it was measured for DPM counts using, Cytoscint® cocktail. Results may be seen in FIG. 37 and Table 13.

TABLE 13

| Human tissue penetration parameters for 5FU. | | | | |
|---|---|---|---|---|
| | lag time (hours) | Flux (μmole/cm$^2$/hour) | cumulative amount permeated (μmole) | Drug retention in tissue (umole/g of tissue) |
| Mammary papilla with keratin plug removal | 8.76 (1.46) | 0.18 (0.05) | 5.06 (1.17) | 7.30 (2.81) |
| Mammary papilla without keratin plug removal | 17.96 (3.80) | 0.03 (0.00) | 0.71 (0.08) | 2.28 (0.04) |

Values in parentheses are SEM. n = 3-4.

Conclusion

This study suggests that 5FU can be delivered via human mammary papilla. Keratin plug plays a big role in the permeation of 5FU. Removal of the keratin plugs from the surface of the mammary papilla induces more than 7 fold increase in the permeation of 5FU across the tissues.

Experiment 13

Transmammary Permeation of EST Across Human Mammary Papilla with and without Removal of the Keratin Plug

TABLE 14

Experimental Design for Experiment 13.

| Experiment design | |
|---|---|
| Donor | 15 mg/ml EST (500 µl) in 50:50 of ethanol:water spiked with 3H EST permeation of EST across human mammary papilla with keratin plugs removed |
| Control | Permeation of above across human mammary papilla without keratin plug removal |
| Receptor | 80:20 mixture of PBS:ethanol |
| Skin saturation | Tissue was set up and kept for 12 hours with no donor but receptor |
| Sampling | 200 µl sample each time |

Experimental Procedure

Figure 38:
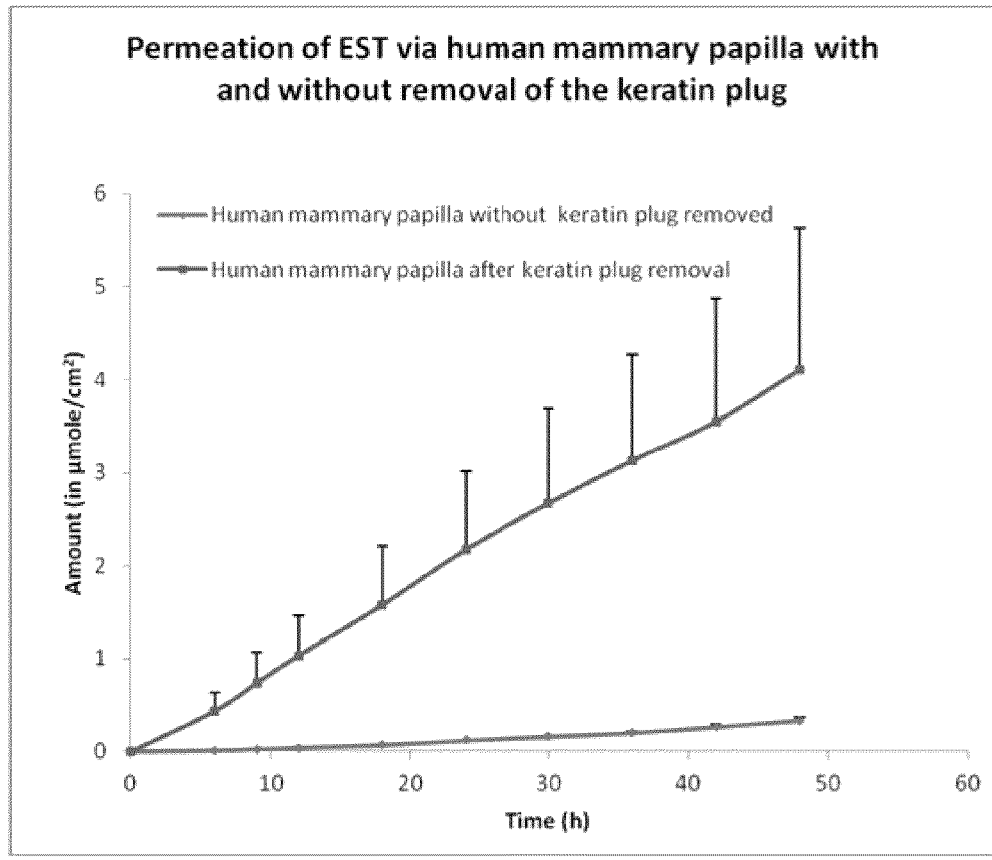
FIG. 38. EST permeation across human mammary papilla with and without removal of the keratin plug. Each data point is represent as mean±SEM, n=3.

Mammary papillae tissues were thawed. Keratin plugs were removed from the mammary papilla tissues using swabs with ethanol. Tissues were set in FDC and kept for saturation for 12 hours. The drug solutions were spiked with radioactive substances. Now 500 µl of the formulation was placed in the donor. Receptor medium was PBS with 7.4 pH. Three 400 µl samples of donor were taken to determine DPM of donors. 200 µl samples were taken from the receptor at pre-determined time points. At the end of 48 hours, tissues were taken, washed, weighed and solubilized using the tissue solubilizer (0.5 M Q ammonium hydroxide in toluene). After 24 hours, it was measured for DPM counts using, Cytoscint® cocktail. Results may be seen in FIG. 38 and Table 15.

Conclusion

This study suggests that EST can be delivered via human mammary papilla. Keratin plug plays a big role in the permeation of EST. Removal of the keratin plugs from the surface of the mammary papilla induces more than 10 fold increase in the permeation of EST across the tissues.

Experiment 14

Transmammary Permeation of Dextran (10,000 Da) Across Human Mammary Papilla with and without Removal of the Keratin Plug

TABLE 16

Experimental Design for Experiment 14.

| Experiment Design | |
|---|---|
| Treatment | 10 mg/ml dextran (500 µl) in 50:50 of ethanol:water spiked with C14 dextran-permeation of dextran across human mammary papilla with keratin plugs removed |
| Control | Permeation of above across human mammary papilla without keratin plug removal |
| Receptor | 7.4 pH PBS with 0.05% w/v sodium azide |
| Skin saturation | Tissue was set up and kept for 12 hours with no donor but receptor |
| Sampling | 200 µl sample each time |

Experimental Procedure

Figure 39:
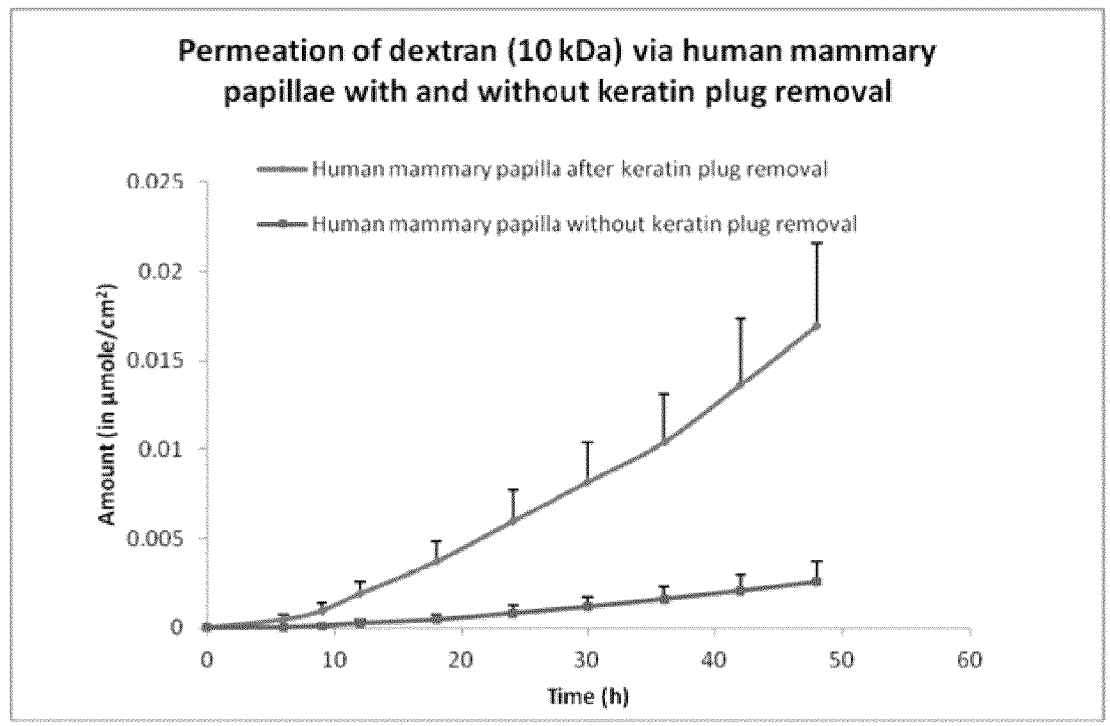
FIG. 39. Dextran permeation across human mammary papilla with and without removal of the keratin plug. Each data point is represent as mean±SEM, n=3.

Mammary papillae tissues were thawed. Keratin plugs were removed from the mammary papilla tissues using swabs with ethanol. Tissues were set in FDC and kept for saturation for 12 hours. The drug solutions were spiked with radioactive substances. Now 500 µl of the formulation was placed in the donor. Receptor medium was PBS with 7.4 pH. Three 400 µl samples of donor were taken to determine DPM of donors. 200 µl samples were taken from the receptor at pre-determined time points. At the end of 48 hours, tissues were taken, washed, weighed and solubilized using the tissue solubilizer (0.5 M Q ammonium hydroxide in toluene). After 24 hours, it was measured for DPM counts using, Cytoscint® cocktail. Results may be seen in FIG. 39 and Table 17.

TABLE 15

Human tissue penetration parameters for EST.

| | lag time (hours) | Flux (µmole/cm$^2$/hour) | cumulative amount permeated (µmole) | Drug retention in tissue (umole/g of tissue)** |
|---|---|---|---|---|
| Mammary papilla with keratin plug removal | 2.08 (0.28) | 0.09 (0.03) | 2.62 (0.97) | 6.25 (2.12) |
| Mammary papilla without keratin plug removal | 7.02 (0.94) | 0.01 (0.00) | 0.58 (0.06) | 1.06 (0.04) |

Values in parentheses are SEM.
*Values multiplied by 1000. n = 3-4.

Results

TABLE 17

Human tissue penetration parameters for dextran.

| | lag time (hours) | Flux (μmole/cm²/hour) | cumulative amount permeated (μmole) | Drug retention in tissue (umole/g of tissue)** |
|---|---|---|---|---|
| Mammary papilla with keratin plug removal | 9.63 (0.90) | 4.31* (0.36)* | 119.42 (19.35)* | 789.33 (99.11)* |
| Mammary papilla without keratin plug removal | 14.74 (1.41) | 0.75* (0.30)* | 16.54 (7.32)* | 89.88 (19.26)* |

Values in parentheses are SEM.
*Values multiplied by 1000. n = 3-4.

Conclusion:

This study suggests that dextran can be delivered via human mammary papilla. Keratin plug plays a big role in the permeation of dextran. Removal of the keratin plugs from the surface of the mammary papilla induces more than 7 fold increase in the permeation of dextran across the tissues.

Experiment 15

In Vitro Drug Transport of Model Compounds, 5FU, EST and Dextran (10,000 Da) Via Porcine Mammary Papilla Vs. Human Mammary Papilla (after Keratin Plug Removal)

TABLE 18

Experimental Design for Experiment 15.

| Experiment design | |
|---|---|
| Donor | 20 mg/ml 5FU spiked with C$^{14}$ 5FU (500 μl) in 1:1 ethanol:water |
| | 15 mg/ml EST (500 μl) ked with 3H EST in 50:50 of ethanol:water spiked with 3H EST |
| | 10 mg/ml dextran (10,000 Da) spiked with C14 dextran (500 μl) in 1:1 of ethanol:water |
| Receptor | For 5FU and dextan- Phosphate buffer (PBS) pH 7.4 with 0.05% w/v sodium azide |
| | For EST- 80:20 of Phosphate buffer (PBS) pH 7.4 with 0.05% w/v sodium azide:ethanol |
| Skin saturation | Tissue was set up and kept for 12 hours with in donor and receptor |
| Sampling | 200 μl sample each time from the receptor |

Experimental Procedure

Figure 40:
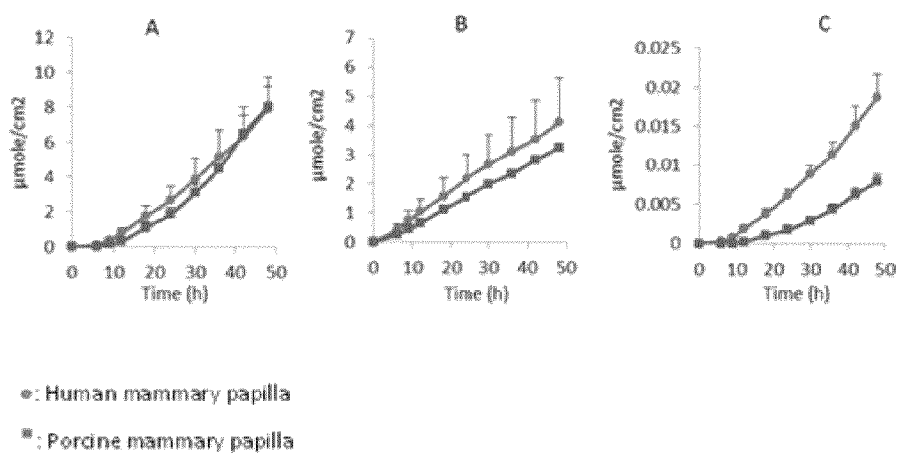
FIG. 40. Profiles of 5FU (A) EST (B) and dextran (C) permeation across human and porcine mammary papilla after pretreatment of keratin plug removal.

Mammary papillae tissues were thawed. Keratin plugs were removed from the mammary papilla tissues using swabs with ethanol. Tissues were set in FDC and kept for saturation for 12 hours. The drug solutions were spiked with radioactive substances. Now 500 μl of the formulation was placed in the donor. Receptor medium was PBS with 7.4 pH. Three 400 μl samples of donor were taken to determine DPM of donors. 200 μl samples were taken from the receptor at pre-determined time points. At the end of 48 hours, tissues were taken, washed, weighed and solubilized using the tissue solubilizer (0.5 M Q ammonium hydroxide in toluene). After 24 hours, it was measured for DPM counts using, Cytoscint® cocktail. Results may be seen in FIG. 40.

Permeation profile for 5FU, EST and dextran via human and porcine mammary papillae, after keratin plug removal, was found to be similar. However, dextran was found to be more permeable via human tissues than porcine tissues. Moreover, as seen from the histology study of the porcine mammary papilla, there is a big difference in the number of ducts in porcine and human mammary papillae. As observed in the dye penetration studies, ducts plan an important role in transmammary drug transport.

Conclusion

This study suggests that porcine mammary papilla can be used as a model for human mammary papilla (when keratin plug is removed from the porcine and human tissues) for drug penetration studies.

Experiment 16

Permeation of 5-Fluorouracil (5FU) Across Human Mammary Papilla and Human Breast Skin

TABLE 19

Experimental Design for Experiment 16.

| Experiment design | |
|---|---|
| Donor | 20 mg/ml 5FU spiked with C14 5FU (500 μl) in 1:1 ehtanol:water |
| Control | Permeation of above across human breast skin |
| Receptor | Phosphate buffer (PBS) pH 7.4 with 0.05% w/v sodium azide |
| Skin saturation | Tissue was set up and kept for 12 hours with PBS in donor and receptor |
| Sampling | 200 μl sample each time from the receptor |
| Donor | 20 mg/ml 5FU spiked with C14 5FU (500 μl) in 1:1 ehtanol:water |
| Control | Permeation of above across human breast skin |
| Receptor | Phosphate buffer (PBS) pH 7.4 with 0.05% w/v sodium azide |
| Skin saturation | Tissue was set up and kept for 12 hours with PBS in donor and receptor |
| Sampling | 200 μl sample each time from the receptor |

Experimental Procedure

Figure 41:
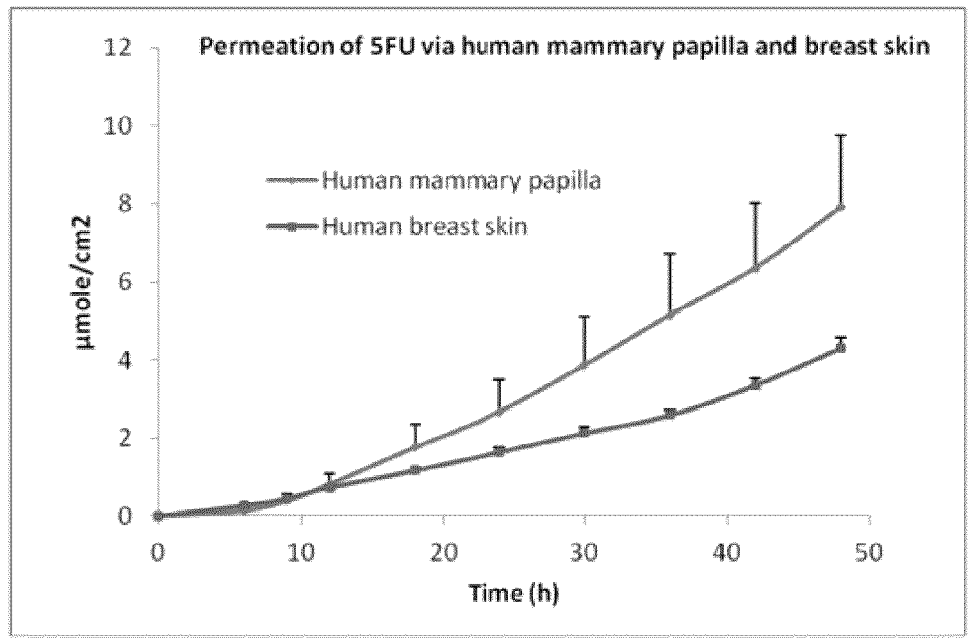
FIG. 41. 5FU permeation across human mammary papilla and human breast skin. Each data point is represented as means±SEM, n=3-4.

Mammary papillae and skin tissues were thawed. Keratin plugs were removed from the mammary papilla tissues using swabs with ethanol. Tissues were set in FDC and kept for saturation for 12 hours. The drug solutions were spiked with radioactive substances. Now 500 μl of the formulation was placed in the donor. Receptor medium was PBS with 7.4 pH. Three 400 μl samples of donor were taken to determine DPM of donors. 200 μl samples were taken from the receptor at pre-determined time points. At the end of 48 hours, tissues were taken, washed, weighed and solubilized using the tissue solubilizer (0.5 M Q ammonium hydroxide in toluene). After 24 hours, it was measured for DPM counts using, Cytoscint® cocktail. Results may be seen in FIG. 41 and Table 20.

TABLE 20

Drug permeation and retention parameters, human tissue penetration parameters for 5FU

| | lag time (hours) | Flux (μmole/cm²/hour) | cumulative amount permeated (μmole) | Drug retention in tissue (umole/g of tissue)** |
|---|---|---|---|---|
| Mammary papilla with keratin plug removal | 8.76 (1.46) | 0.18 (0.05) | 5.06 (1.17) | 7.30 (2.81) |
| breast skin | 3.64 (0.37) | 0.08 (0.01) | 2.69 (0.22) | 9.56 (1.11) |
| Mammary papilla with keratin plug removal | 8.76 (1.46) | 0.18 (0.05) | 5.06 (1.17) | 7.30 (2.81) |
| breast skin | 3.64 (0.37) | 0.08 (0.01) | 2.69 (0.22) | 9.56 (1.11) |

Values in parentheses are SEM. n = 3-4

Discussion:

The results of this study show that permeability of 5FU across human mammary papilla is higher than that across human breast skin. As 5FU permeation across mammary papilla is showing high standard error of mean, the difference is not statistically significant. Higher drug transport could be due to the ducts which may carry drug from the surface of mammary papilla to the deeper tissue. This result supports the hypothesis that milk ducts are playing important role in the transmammary drug transport.

Conclusion:

This study suggests that permeability of 5FU across human mammary papilla is higher than that across human breast skin. Some more studies are required to refine the data and confirm the results.

Experiment 17

Permeation of Estradiol (EST) Across Human Mammary Papilla (after Keratin Plug Removal) and Human Breast Skin

TABLE 21

Experimental Design for Experiment 17.

| Experiment design | |
|---|---|
| Donor | 15 mg/ml EST (500 μl) ked with 3H EST in 50:50 of ethanol:water spiked with 3H EST |
| Control | Permeation of above across human breast skin |
| Receptor | 80:20 mixture of phosphate buffer (pH 7.4):ethanol |
| Skin saturation | Tissue was set up and kept for 12 hours with PBS in donor and receptor |
| Sampling | 200 μl sample each time |

Experimental Procedure

Figure 42:
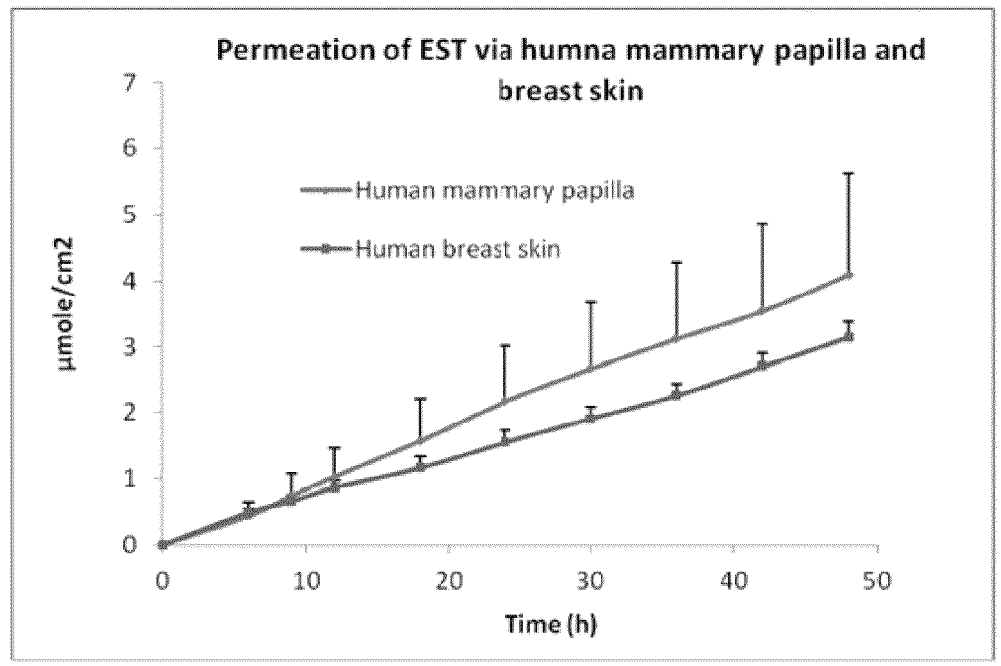
FIG. 42. EST permeation across human mammary papilla and human breast skin. Each data point is represented as means±SEM, n=3.

Mammary papillae and skin tissues were thawed. Keratin plugs were removed from the mammary papilla tissues using swabs with ethanol. Tissues were set in FDC and kept for saturation for 12 hours. The drug solutions were spiked with radioactive substances. Now 500 μl of the formulation was placed in the donor. Receptor medium was PBS with 7.4 pH. Three 400 μl samples of donor were taken to determine DPM of donors. 200 μl samples were taken from the receptor at pre-determined time points. At the end of 48 hours, tissues were taken, washed, weighed and solubilized using the tissue solubilizer (0.5 M Q ammonium hydroxide in toluene). After 24 hours, it was measured for DPM counts using, Cytoscint® cocktail. Results may be seen in FIG. 42 and Table 22.

TABLE 22

Drug permeation and retention parameters, human tissue penetration parameters for EST.

| | lag time (hours) | Flux (μmole/cm²/hour) | cumulative amount permeated (μmole) | Drug retention in tissue (umole/g of tissue) |
|---|---|---|---|---|
| Mammary papilla with keratin plug removal | 2.08 (0.28) | 0.09 (0.03) | 2.62 (0.97) | 6.25 (2.12) |
| breast skin | 0.56 (0.22) | 0.07 (0.01) | 2.10 (0.16) | 2.94 (0.30) |
| breast skin | 0.56 (0.22) | 0.07 (0.01) | 2.10 (0.16) | 2.94 (0.30) |

Values in parentheses are SEM. n = 3-4.

Discussion:

The results of this study show that permeability of EST across human mammary papilla is higher than that across human breast skin. As EST permeation across mammary papilla is showing high standard error of mean, the difference is not statistically significant. Higher drug transport could be due to the ducts which may carry drug from the surface of mammary papilla to the deeper tissue. This result supports the hypothesis that milk ducts are playing important role in the transmammary drug transport.

Conclusion:

This study suggests that permeability of EST across human mammary papilla is higher than that across human breast skin. Some more studies are required to refine the data.

Experiment 18

Permeation of Dextran (10000 Da) Across Human Mammary Papilla and Human Breast Skin

TABLE 23

| Experimental Design for Experiment 18. | |
|---|---|
| Experiment design | |
| Donor | 10 mg/ml Dextran (500 µl) spiked with C14 Dextran in 1:1 of ethanol:water |
| Control | Permeation of above across breast skin |
| Receptor | Phosphate buffer 7.4 pH with 0.05% w/v sodium azide |
| Skin saturation | Tissue was set up and kept for 12 hours with no PBS in donor and receptor chamber of the diffusion cell |
| Sampling | 200 µl sample each time |

Experimental Procedure

Figure 43:
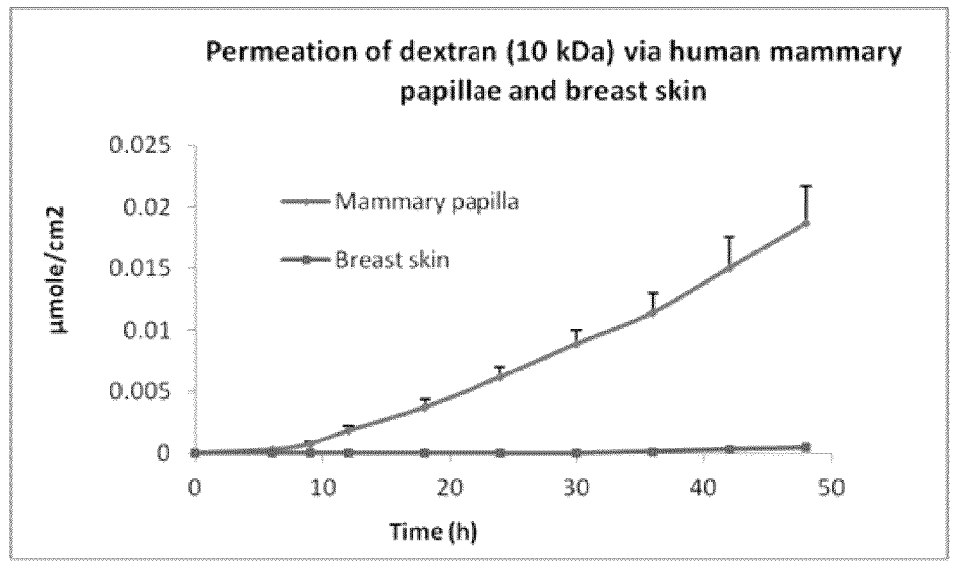
FIG. 43. Permeation of dextran (10 kDa) via human mammary papillae with keratin plug removal and breast skin. Each data point is represented as means±SEM, n=3.

Mammary papillae tissues were thawed. Keratin plugs were removed from the mammary papilla tissues using swabs with ethanol. Tissues were set in FDC and kept for saturation for 12 hours. The drug solutions were spiked with radioactive substances. Now 500 µl of the formulation was placed in the donor. Receptor medium was PBS with 7.4 pH. Three 400 µl samples of donor were taken to determine DPM of donors. 200 µl samples were taken from the receptor at pre-determined time points. At the end of 48 hours, tissues were taken, washed, weighed and solubilized using the tissue solubilizer (0.5 M Q ammonium hydroxide in toluene). After 24 hours, it was measured for DPM counts using, Cytoscint® cocktail. Results may be seen in FIG. 43 and Table 24.

TABLE 24

| Human tissue penetration parameters for dextran. | | | | |
|---|---|---|---|---|
| | lag time (hours) | Flux (µmole/cm$^2$/hour) | cumulative amount permeated (µmole) | Drug retention in tissue (umole/g of tissue) |
| Mammary papilla with keratin plug removal | 9.63 (0.90) | 4.31* (0.36)* | 119.42 (19.35)* | 789.33 (99.11)* |
| breast skin | 30.15 (3.04) | 0.255* (0.07)* | 2.86* (0.41)* | 102.95* (6.30)* |

Values in parentheses are SEM.
*Values multiplied by 1000. n = 3-4.

Discussion:

The results of this study show that dextran which is a 10 kDa hydrophilic molecule can permeate across human mammary papilla. As a control experiment permeation of dextran across surrounding breast skin was also performed. The results suggest that dextran has higher permeability across human mammary papilla than porcine mammary papilla. Moreover permeation of dextran via human mammary papilla was significantly higher than breast skin, which showed no penetration of dextran even with 48 hrs treatment (FIG. 2).

Conclusion:

This study suggests that the hydrophilic macromolecules dextran, with size of 10 kDa, can be delivered via human mammary papilla and it shows higher permeability via human mammary papilla than the surround breast skin and porcine mammary papilla.

Experiment 19

Transmammary Permeation of 5FU Across Human Areola and Human Breast Skin

| Experimental Design for Experiment 19. | |
|---|---|
| Experiment design | |
| Donor | 20 mg/ml 5FU (500 µl) in 50:50 of ethanol:water spiked with C$^{14}$ 5FU |
| Control | Permeation of above across human breast skin |
| Receptor | 7.4 pH PBS with 0.05% w/v sodium azide |
| Skin saturation | Tissue was set up and kept for 12 hours with no donor but receptor |
| Sampling | 200 µl sample each time |

Experimental Procedure

Figure 44:
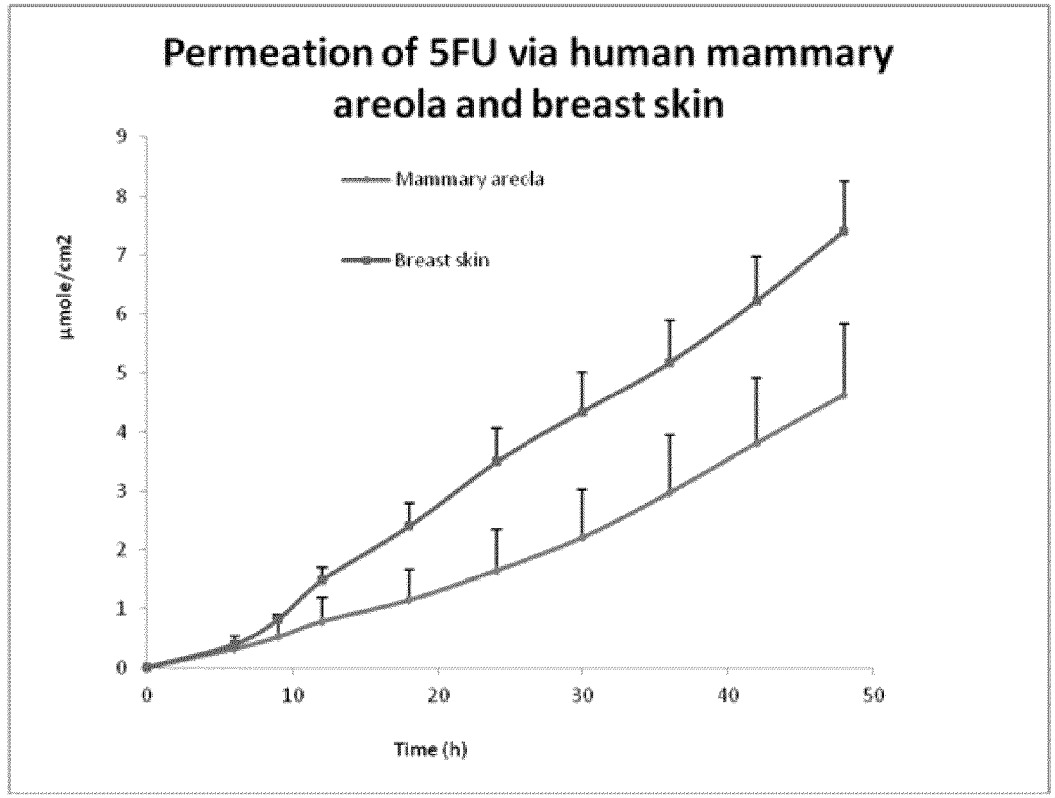
FIG. 44. 5FU permeation across human mammary areola and human breast skin. Each data point is represented as means±SEM, n=4.

Mammary areolae and skin tissues were procured from a cadaver (49 years, Pacific Islander). Tissues were set in FDC and kept for saturation for 12 hours. The drug solutions were spiked with radioactive substances. Now 500 µl of the formulation was placed in the donor. Receptor medium was PBS with 7.4 pH. Three 400 µl samples of donor were taken to determine DPM of donors. 200 µl samples were taken from the receptor at pre-determined time points. At the end of 48 hours, tissues were taken, washed, weighed and solubilized using the tissue solubilizer (0.5 M Q ammonium hydroxide in toluene). After 24 hours, it was measured for DPM counts using, Cytoscint® cocktail. Results may be seen in FIG. 44.

Conclusion:

This results of this study show that permeability of 5FU across human mammary areola is lower than that across human breast skin. Though some more studies need to be performed to refine this data, it probably suggests that permeability of 5FU across mammary areola could be lesser than breast skin.

Experiment 20

Transmammary Permeation of EST Across Human Mammary Areola and Human Breast Skin

TABLE 26

Experimental Design for Experiment 20.

| Experiment design | |
|---|---|
| Donor | 15 mg/ml EST (500 µl) in 50:50 of ethanol:water spiked with 3H EST |
| Control | Permeation of above across human breast skin |
| Receptor | 80:20 mixture of PBS:ethanol |
| Skin saturation | Tisue was set up and kept for 12 hours with no donor but receptor |
| Sampling | 200 µl sample each time |

Experimental Procedure

Figure 45:
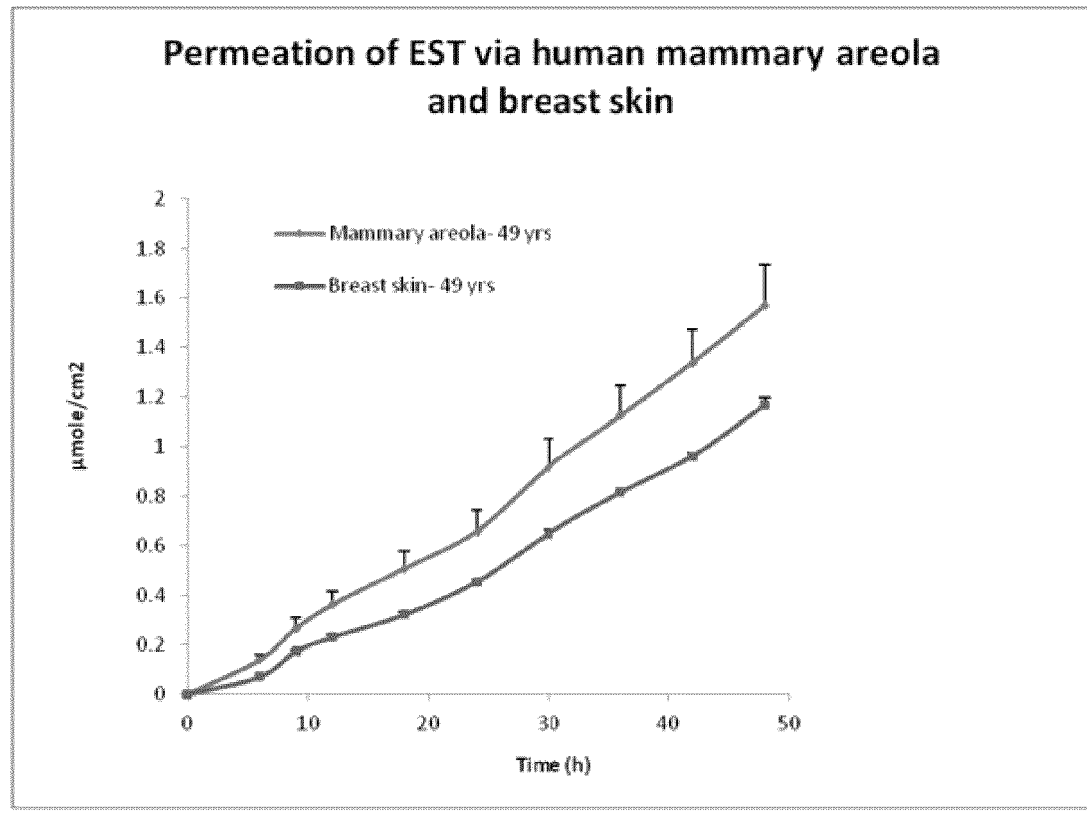
FIG. 45. EST permeation across human mammary areola and breast skin. Each data point is represented as means±SEM, n=4.

Mammary areolae and skin tissues were procured from a cadaver (49 years, Pacific Islander). Tissues were set in FDC and kept for saturation for 12 hours. The drug solutions were spiked with radioactive substances. Now 500 µl of the formulation was placed in the donor. Receptor medium was PBS with 7.4 pH. Three 400 µl samples of donor were taken to determine DPM of donors. 200 µl samples were taken from the receptor at pre-determined time points. At the end of 48 hours, tissues were taken, washed, weighed and solubilized using the tissue solubilizer (0.5 M Q ammonium hydroxide in toluene). After 24 hours, it was measured for DPM counts using, Cytoscint® cocktail. Results may be seen in FIG. 45.

Discussion:

This results of this study show that permeability of EST across human mammary areola is similar or higher than that across human breast skin. Though some more studies need to be performed to refine this data, it probably suggests that permeability of EST across mammary areola is at least similar to breast skin.

Conclusion:

This study suggests that permeability of EST across human mammary papilla areola is similar or higher than that across human breast skin. Some more studies are required to refine the data and confirm the results.

Experiment 21

Transmammary Permeation of Dextran (10,000 Da) Across Human Mammary Areola and Breast Skin

TABLE 27

Experimental Design for Experiment 21.

| Experiment design | |
|---|---|
| Treatment | 10 mg/ml dextran (500 µl) in 50:50 of ethanol:water spiked with C14 dextran-permeation of dextran across human mammary papilla with keratin plugs removed |
| Control | Permeation of above across human mammary papilla without keratin plug removal |
| Receptor | 7.4 pH PBS with 0.05% w/v sodium azide |
| Skin saturation | Tissue was set up and kept for 12 hours with no donor but receptor |
| Sampling | 200 µl sample each time |

Experimental Procedure

Figure 46:
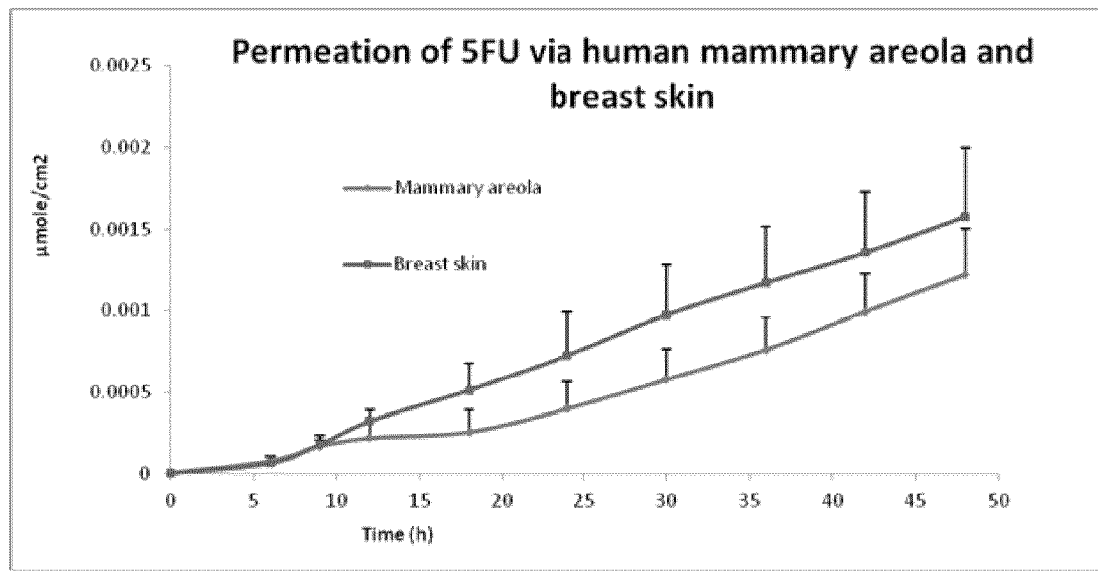
FIG. 46. Dextran permeation across human mammary areola and breast skin. Each data point is represented as means±SEM, n=4.

Mammary areolae and skin tissues were procured from a cadaver (49 years, Pacific Islander). Tissues were set in FDC and kept for saturation for 12 hours. The drug solutions were spiked with radioactive substances. Now 500 µl of the formulation was placed in the donor. Receptor medium was PBS with 7.4 pH. Three 400 µl samples of donor were taken to determine DPM of donors. 200 µl samples were taken from the receptor at pre-determined time points. At the end of 48 hours, tissues were taken, washed, weighed and solubilized using the tissue solubilizer (0.5 M Q ammonium hydroxide in toluene). After 24 hours, it was measured for DPM counts using, Cytoscint® cocktail. Results may be seen in FIG. 46.

Conclusion:

The results of this study show that permeability of dextran across human mammary areola is similar to that across human breast skin.

Experiment 22

Biodistribution of 5FU in Rats after Transdermal, Transmammary and Intravenous Injection of 5FU Procedure:

For animal studies 7-10 weeks old Female Sprague-Dawley rats, purchased from the Charles River Breeding Laboratories (Wilmington, Mass.), were used. The animals were given water and food ad libitum and maintained in a climate controlled environment. The experimental protocol was approved by our Institutional Animal Care and Use Committee. The animals were observed for 4 weeks before starting the experiment.

Rats were anesthetized by Isoflurane inhalation using an anesthesia device (VetEquip-VE 2848, Pleasanton, Calif.). Keratin plugs were removed from the surface of the mammary papilla by gentle rubbing with cotton gauze soaked in ethanol. A duct of mammary papilla was cannulated with a 34-gauge, blunt-ended needle attached to a syringe and 100 µl of 0.4% Trypan Blue solution was slowly infused into the mammary gland while the opening was visualized under a dissection microscope (Celestron-44202, Torrance, Calif.). Immediately after the injection animal was euthanized. Following sacrifice, the gland was exposed for visualization.

Abdominal hair of the rats was removed 24 h before the treatment using a hair clipper. On the day of treatment animals were anesthetized using Isoflurane. Before treatment surrounding breast skin was covered with scotch tape to limit the drug exposure to the mammary papilla. For drug treatment 250 µl of 5FU solution (10 mg/ml) was applied onto a single mammary papilla using a hilltop chamber. Drug treatment was continued for 6 h under anesthesia.

Tail of the rat was wiped with warm water to locate the vein. Solution of 5FU was prepared in 0.9% NaCl (10 mg/ml)

and 50 μl of the solution was injected into the vein using 27-gauge, ½", needle attached to a syringe.

Blood samples were collected from the retro-orbital plexus of the animals using heparinized glass capillaries. Upon topical drug application, blood aliquots were collected right before drug application, every 15 minutes till one hour after starting the drug application and then every hour till 6 hours, when the drug application was removed. In animals with intravenous drug administration, blood samples were collected right before drug application and then every three or five minutes after drug application till 15 minutes or 30 minutes when the animals were sacrificed after blood collection. The blood samples were collected into the heparinized tubes and then centrifuged at 10,000 rpm for 15 minutes, within two hours after blood collection. After centrifugation, supernatant (plasma) was collected and mixed with scintillation cocktail for radioactivity analysis.

After collecting the last blood sample, rats were euthanized by $CO_2$ asphyxiation and opened from the abdominal side. First of all treated mammary papilla or skin was collected followed by mammary gland. After this other vital organs including kidneys, liver, spleen, lungs, brain and heart were harvested. All the tissues were weighed followed by mechanical homogenization. After this, the homogenate was mixed with commercially available tissue solubilizer (Biosol™, National Diagnostics, Atlanta, Ga.) and incubated at 50° C. for 24 hours. Solubilized tissues were mixed with 30% v/v hydrogen peroxide solution and again incubated at 50° C. for 4 hours. Finally, the decolorized solutions of the tissues were mixed with scintillation cocktail to determine radioactivity content.

Results:

In vitro studies showed feasibility of transmammary delivery in human. However, considering the complex nature of the biological system, it is important to study the feasibility of this approach in an animal model. To this end, transmammary delivery of a model compound, 5FU—which is currently used in breast cancer therapy in the form an intravenous injection, was studied in SD rats.

For comparison transdermal as well as intravenous delivery of 5FU was also studied, as control groups. For topical application, i.e. transmammary and transdermal, drug treatment was given for 6 hours. For intravenous drug administration the study was performed for 30 minutes (~two half-lives of 5FU) after the injection. Initially a study was performed for the period of 6 hours after intravenous injection of 5FU but no amount of drug was observed in the body. Due to short elimination half-life of 5FU, most of the drug might have got washed off from the system (data not shown).

One of the goals of the animal studies was to analyze amount of drug that reaches in to the mammary tissues upon localized topical delivery of the model compound 5FU. It is important to know whether the drug reaches into the mammary gland of the breast which exists into the underlying tissues, upon topical application. To determine exact location of the mammary gland into the SD rats, 0.4% trypan blue was injected into a duct of a mammary papilla into the rat. Immediately after the injection, animal was euthanized and its abdomenal side was opened. Blue colored ductolobular network (mammary gland) was clearly visible into the underlying tissues.

Figure 47:
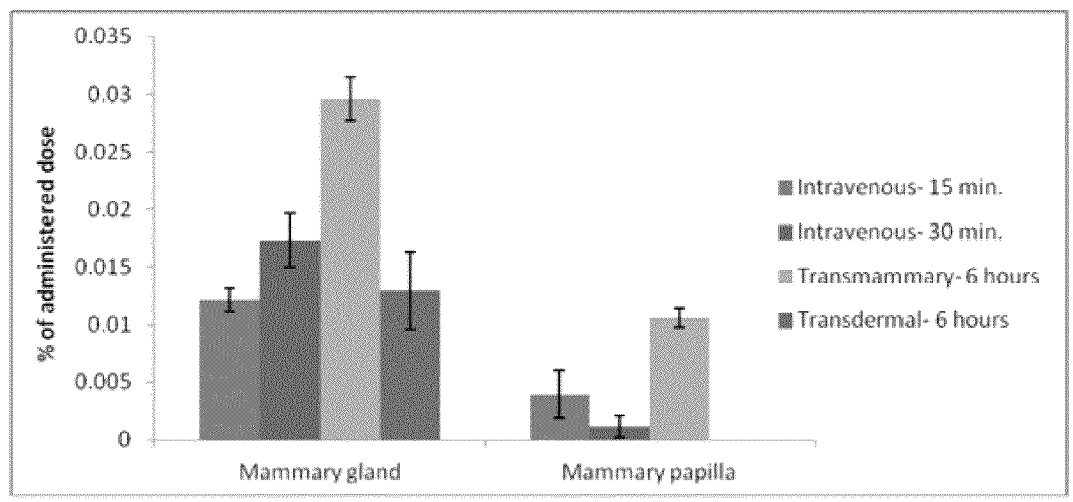
FIG. 47. Retention of 5FU in mammary tissues after intravenous, transmammary and transdermal treatment. Each value is represented as means±SEM (* and **p<0.05 when compared with corresponding value, in intravenous injection treatment group and topical transdermal treatment group respectively, by two tail unpaired t-test, n=3.

As shown in the diagram (FIG. 47), 5FU was found to be accumulated into the mammary gland in all the treatment groups. However, highest amount of 5FU in mammary gland was observed in case of transmammary treatment followed by intravenous and transdermal treatments. Transmammary treatment induced significant retention of 5FU into the mammary papilla. Intravenous injection showed some accumulation of 5FU into the mammary papilla while in case of transdermal treatment, no 5FU was observed into the mammary papilla. Apart from mammary tissues, drug accumulation was also determined in other organs of the rat body. The results show that upon topical application (transmammary and transdermal) 5FU retention into the vital organs of the rat, including, kidneys, heart, liver, lungs, spleen and brain, was several folds lower than that after intravenous injection. Profile of 5FU in plasma showed that 5FU was quickly eliminating from the blood after intravenous injection. In case of topical delivery, no amount of 5FU was observed into the blood. This could be due to lower amount of drug reaching in the systemic circulation along with simultaneous elimination from the body.

Discussion

In vivo studied were performed to analyze fate of the drug when applied topically over mammary papilla. Retention of the model compound 5FU in mammary tissue, including mammary gland and mammary papilla, was highest among all three groups. Accumulation of the drug into the mammary gland suggests that the drug was able to get transported into the deeper breast. Transdermal treatment of 5FU had shown accumulation of the drug into the mammary gland. This suggests that topical treatment of the drug on the entire breast, i.e. mammary papilla and the surrounding skin could be an option when mammary papilla alone may not provide enough area to reach the therapeutic level of the drug into the breast tissue.

5FU accumulation in other organs was highest upon intravenous injection which justifies the adverse effects of the injectable preparations used for breast cancer chemotherapy. As 5FU is mainly metabolized and excreted by liver and kidneys highest drug accumulation was observed in those organs in all treatment groups. However, topical delivery had shown relatively minimal retention of drug in any of the organs. Drug concentration in plasma was below the level of detection in case of topical treatments.

Figure 48:
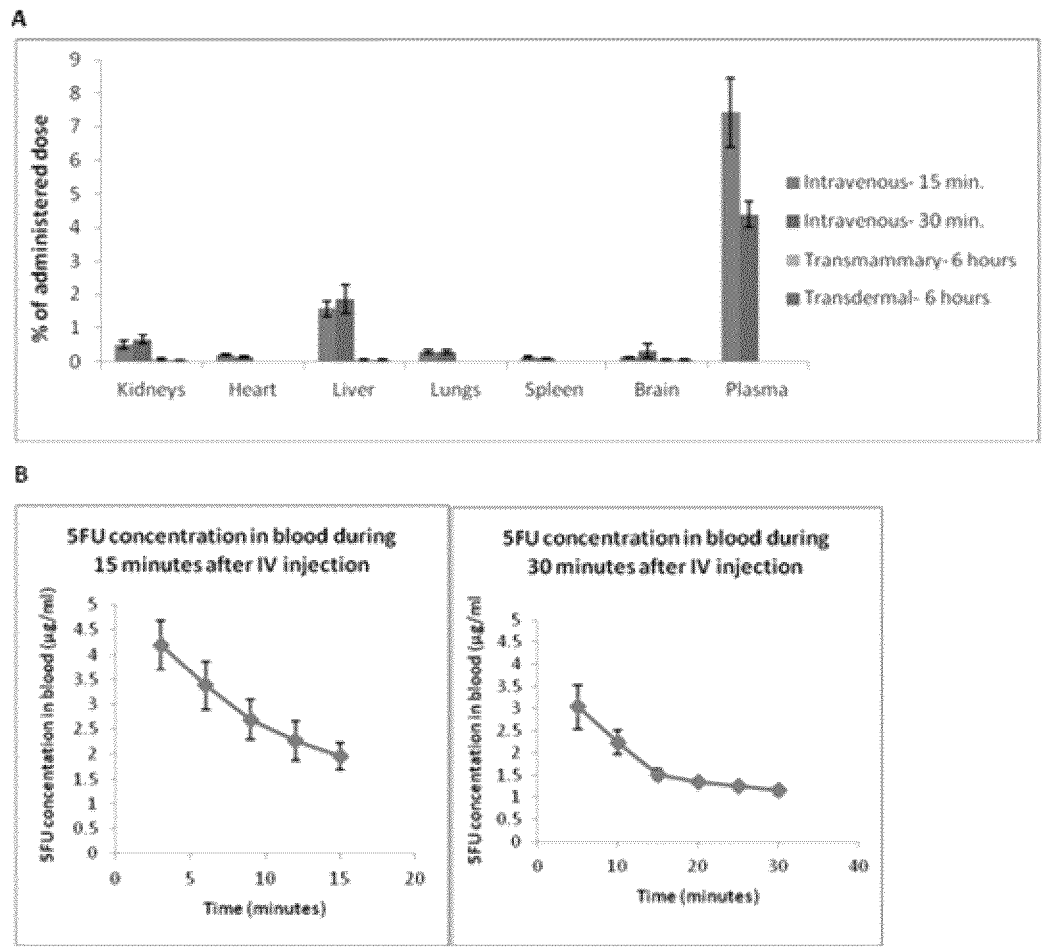
FIG. 48. (A): Retention of 5FU in vital organs of rat after intravenous, transmammary and transdermal treatment. (B): Amount of 5FU in plasma after intravenous injection. No drug was detected in the blood at any time points after topical treatments. Each value is represented as means±SEM (*p<0.05 when compared with corresponding value, in intravenous injection treatment group and topical transdermal treatment group, by two tail unpaired t-test, n=3).

Profile of 5FU in plasma showed fast elimination of the drug from the blood. As reported into the literature a two compartment model profile was observed. The in vivo data suggests that 5FU can be delivered to the mammary tissues with minimal exposure of the drug into the blood and other vital organs of the body (see, e.g., FIG. 48).

Conclusion

In-vivo data suggests feasibility of this approach for localized delivery and minimal system absorption. The findings can be translated to clinical application by developing suitable formulations and devices for application on the breast.

Experiment 23

Biodistribution of 5FU in 9 Weeks Old Female Sprague-Dawley Rats 6 Hours after Administration of Intraductal and Intravenous Injection of 10 mg/ml 5FU in Saline Procedure:

The hair on the skin of the rats was removed using a hair removing formulation. The treatment was given after 24 hours to make sure the skin is recovered if damaged or altered due to the hair removal treatment.

Figure 49:
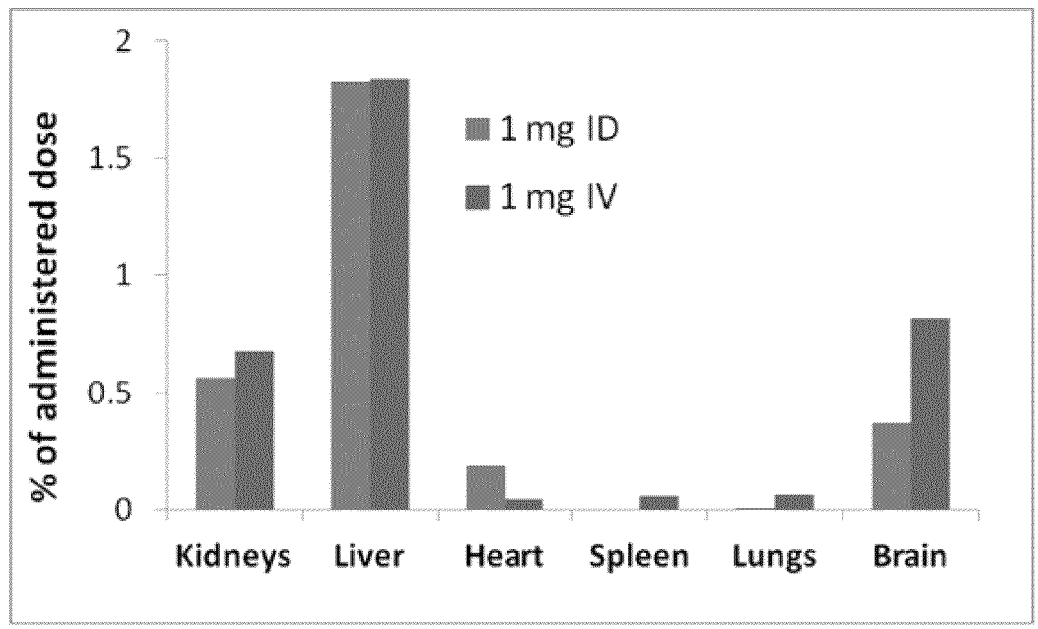
FIG. 49. Percentage of total given dose (1 mg) of 5FU retaining into the organs of rats, 6 hours after intraductal (ID) and intravenous injection (IV). (n=1).

Next day, the rats were placed under controlled Isoflurane anesthesia. Now 500 μl of Blood samples were collected from each animal before beginning the experiment, by retro-orbital technique, as a control. For intraductal injection the mammary papilla to be treated was gently wiped with an alcoholic cotton swab to remove the keratin plug. Now 100 μl of 5FU solution in saline (10 mg/ml) was injected into the duct of the mammary papilla under a stereo-microscope. After this the animal was removed from anesthesia and placed into the cage. In case of intravenous injection, similar to intraductal, 100 μl of 5FU solution in saline (10 mg/ml) was injected into the tail vein and the animal was placed into the cage for 6 hours. At the end of 6 hours 500 μl of blood sample was collected. After this the rats were euthanized. Now for intraductal injection the treated area of the rat was cleaned with water. The rat was opened from the abdominal skin. Treated mammary papilla and mammary gland existing underneath the treated mammary papilla was excised and collected. Lateral mammary papilla and mammary gland was collected along with distant mammary papilla and mammary gland, as controls. Followed by this other organs including heart, brain, liver, spleen, kidneys and lungs were collected. In case of intravenous treatment, blood was collected and mammary tissues (mammary papilla, mammary gland and surrounding breast skin) was collected along with other organs including heart, brain, liver, spleen, kidneys and lungs. All the tissues were weighed and then mechanically homogenized to extract the drug. The homogenates were mixed with hydrogen peroxide solution (30% v/v) and then radioactivity into the samples was measured by liquid scintillation counting. Similarly blood samples were centrifuged and the supernatants were analyzed by scintillation counting. Results may be seen in FIG. 49, Table 28 and Table 29.

Results:

TABLE 28

Amount of 5FU retaining into the mammary papillae after intraductal and intravenous injection.

| Tissue source | Treatment | Drug per gram tissue of mammary papilla (μmole/g) |
|---|---|---|
| Rat-intraductal in vivo | Injection followed by 6 hours | 1.36 |
| Rat-intravenous in vivo | Injection followed by 6 hours | 0 |

TABLE 29

Amount of 5FU retaining into the mammary tissues (mammary gland, mammary papilla and the surrounding breast skin) after intraductal and intravenous injection.

| Tissue/Blood | Drug per gram tissue (μmole/g) | |
|---|---|---|
| | intraductal | Intravenous |
| Mammary gland treatment | 0 | 0 |
| Mammary papilla | 1.36 | 0 |
| Surrounding skin | 0.23 | 0 |

Conclusion:

This study suggests that intraductal and intravenous injection of 5FU does not show high retention of 5FU in mammary tissues in rats. However significant amount of 5FU in vital organs of the body including kidneys, liver and brain may show adverse effect of the drug in the rats.

Experiment 24

Biodistribution of 5FU in 9 Weeks Old Female Sprague-Dawley Rats 30 Minutes after Administration of Intraductal and Intravenous Injection of 10 mg/Ml 5FU in Saline Procedure:

The hair on the skin of the rats was removed using a hair removing formulation. The treatment was given after 24 hours to make sure the skin is recovered if damaged or altered due to the hair removal treatment.

Figure 50:
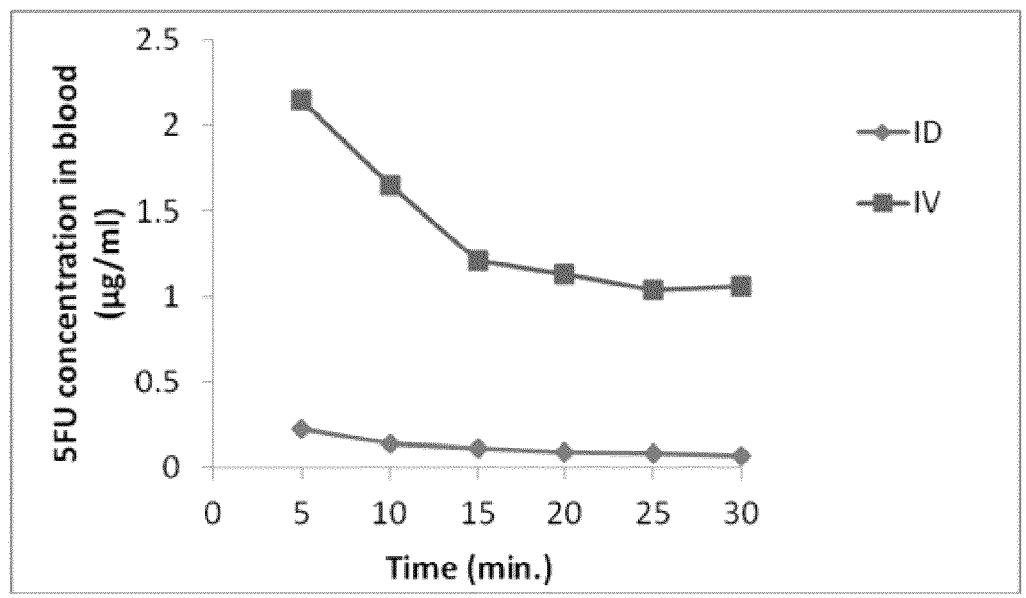
FIG. 50. 5FU pharmacokinetic profile in rat serum after intravenous (IV) and intraductal (ID) administration of 0.5 mg 5FU in saline (10 mg/ml) (n=1).

Next day, the rats were placed under controlled Isoflurane anesthesia. Now 500 μl of Blood samples were collected from each animal before beginning the experiment, by retro-orbital technique, as a control. For intraductal injection the mammary papilla to be treated was gently wiped with an alcoholic cotton swab to remove the keratin plug. Now 50 μl of 5FU solution in saline (10 mg/ml) was injected into the duct of the mammary papilla under a stereo-microscope. After this the animal was removed from anesthesia and placed into the cage. In case of intravenous injection, similar to intraductal, 50 μl of 5FU solution in saline (10 mg/ml) was injected into the tail vein and the animal was placed into the cage for 30 minutes. At the end of 30 minutes 500 μl of blood sample was collected. After this the rats were euthanized. Now for intraductal injection the treated area of the rat was cleaned with water. The rat was opened from the abdominal skin. Treated mammary papilla and mammary gland existing underneath the treated mammary papilla was excised and collected. Lateral mammary papilla and mammary gland was collected along with distant mammary papilla and mammary gland, as controls. Followed by this other organs including heart, brain, liver, spleen, kidneys and lungs were collected. In case of intravenous treatment, blood was collected and mammary tissues (mammary papilla, mammary gland and surrounding breast skin) was collected along with other organs including heart, brain, liver, spleen, kidneys and lungs. All the tissues were weighed and then mechanically homogenized to extract the drug. The homogenates were mixed with hydrogen peroxide solution (30% v/v) and then radioactivity into the samples was measured by liquid scintillation counting. Similarly blood samples were centrifuged and the supernatants were analyzed by scintillation counting. Results may be seen in FIG. 50, Tables 30-31.

TABLE 30

Amount of 5FU retaining into the mammary papillae after intraductal and intravenous injection.

| Tissue source | Treatment | Drug per gram tissue of mammary papilla (μmole/g) |
|---|---|---|
| Rat-intraductal in vivo | Injection followed by 30 min | 0.16 |
| Rat-intravenous in vivo | Injection followed by 30 min | 0 | n = 1

TABLE 31

Amount of 5FU retaining into the mammary tissues (mammary gland, mammary papilla and the surrounding breast skin) after intraductal and intravenous injection.

| | Drug per gram tissue (μmole/g) | |
|---|---|---|
| Tissue/Blood | ID (30 min) | IV (30 min) |
| Mammary gland treatment | 0.018 | 0.009 |
| Mammary papilla | 0.16 | 0 |
| Surrounding skin | 0.03 | 0 |

Conclusion:

This study suggests that intraductal and intravenous injection of 5FU does not show high retention of 5FU in mammary tissues in rats. However significant amount of 5FU in vital organs of the body including kidneys, liver and brain may show adverse effect of the drug in the rats.

Experiment 25

Penetration of α-Santalol into Porcine Mammary Papilla (without Keratin Plug Removal) after Treatment of 6 Hours, 48 Hours and a Disposition Study with 6 Hours Treatment and 48 Hours Permeation

TABLE 32

Experimental Design for Experiment 25.

| Experiment design | |
|---|---|
| Donor | 500 μl of 5% α-santalol v/v in 2:1 of ethanol:phosphate buffer (PBS) with pH 7.4 |
| Control | No control experiment |
| Receptor | 1:1 of ethanol:PBS |
| Treatment | total 3 experiments: 1) 6 hours study with 6 hours treatment 5) 6 hours treatment and 48 hours disposition study and 3) 48 hours study with 48 hours treatment |
| Skin saturation | Tissue was set up and kept for 12 hours with no drug in donor chamber of the diffusion cell (only PBS) |
| Sampling | 200 μl sample each time |

Hydroalcoholic Solution:

| α-santalol | 5% v/v |
|---|---|
| 2:1 of ethanol:phosphate buffer | q.s. |

Figure 51:
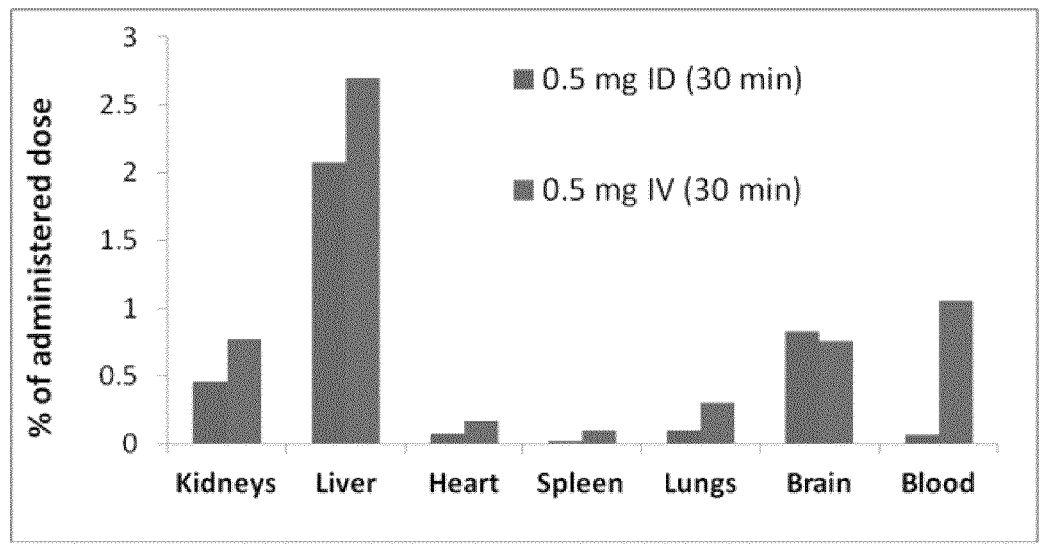
FIG. 51. Percentage of total given dose of 5FU retaining into the organs of rats after intraductal and intravenous injection (after 30 min or 6 h; n–1).

Experiment procedure—Mammary papillae were setup in FSD and kept for saturation for 12 hours. Then 500 μl of drug formulation was added in the donor. Three 200 μl samples of donor were taken to determine GCMS area of donors. Now 200 μl samples were collected from the receptor on each time point. After 48 hours, mammary papillae were taken, washed, cut into 2 mm thick sections, weighed and solubilized using the tissue solubilizer (1M NaOH). After 24 hours, santalol was extracted using ethyl acetate and it was measured for area by GCMS. Results may be seen in FIG. 51 and Table 33.

Results:

TABLE 33

Retention of α-santalol into porcine mammary papilla.

| Mode | Tissue retention (μmole/g tissue) | Tissue retention (% of applied dose) |
|---|---|---|
| 6 h treatment | 5.21 (0.41) | 2.20 (0.19) |
| 6 hours treatment 48 h disposition study | 5.34 (0.52) | 2.01 (0.12) |
| 48 h treatment | 35.52 (3.69) | 15.30 (2.20) |

Values in parentheses are SEM (n = 3)

Results and Discussion

The drug retention into the tissue data shows that α-santalol tends to retain into the tissue and was not found into the receptor in any of the experiments. With longer treatment, higher amounts of drug was found to be penetrating and retaining into the tissue. This could be due to the highly lipophilic nature of α-santalol which can bind with the fat into the tissue. With 6 h treatment and 6 h treatment followed by 48 h disposition study, similar amount of α-santalol was found into the tissue which indicated that the drug does not displace from the tissue towards receptor over the time, which could be due to string binding of the drug into the tissue. Now 6 h as well as 48 h studies show that significant amount of drug is penetrating into the tissue and further studies may be able to answer these questions. It is important to note that these studies were performed without removal of the keratin plug from the surface of the mammary papilla tissues. Removal of the keratin plug may allow α-santalol to permeate across the tissue, as shown with our other studies.

Conclusion

α-santalol can be delivered into the mammary papilla by topical application. Deeper penetration of the drug into the tissues needs to be determined in an animal model.

Experiment 26

Penetration of α-Santalol from Hydroalcoholic Solution and Microemulsion Via Porcine Mammary Papilla after Keratin Plug Removal Pretreatment

TABLE 34

Experimental Design for Experiment 26.

| Experiment design | |
|---|---|
| Donor | 500 μl of w/o microemulsion with 25% v/v α-santalol |
| Control | 400 μl 5% v/v α-santalol solution in 2:1 (ethanol:PBS) |
| Receptor | 1:1 of ethanol:Phosphate buffer (PBS) with pH 7.4 |
| Treatment | α-santalol in donor and sampling for 48 hours |
| Skin saturation | Skin was set up and kept for 12 hours with no drug in donor chamber (only PBS) and 1:1 ethanol:PBS in receptor chamber of the diffusion cell |
| Sampling | 400 μl sample each time |

Formulation:
Microemulsion:

| Polysorbate 80 | 35% v/v |
|---|---|
| Ethanol | 35% v/v |

| | |
|---|---|
| α-santalol | 25% v/v |
| Water | 5% v/v |

Hydroalcoholic Solution:

| | |
|---|---|
| α-santalol | 5% v/v |
| 2:1 of ethanol:phosphate buffer | q.s. |

Microemulsion preparation—First 35% polysorbate 80 (Tween 80) was taken and mixed with ethanol. After this 25% α-santalol was added in this and vortexed. After this, 5% water was added into this drop by drop and vortexed. This emulsion was thoroughly mixed and vortexed.

Experimental Procedure

Figure 52:
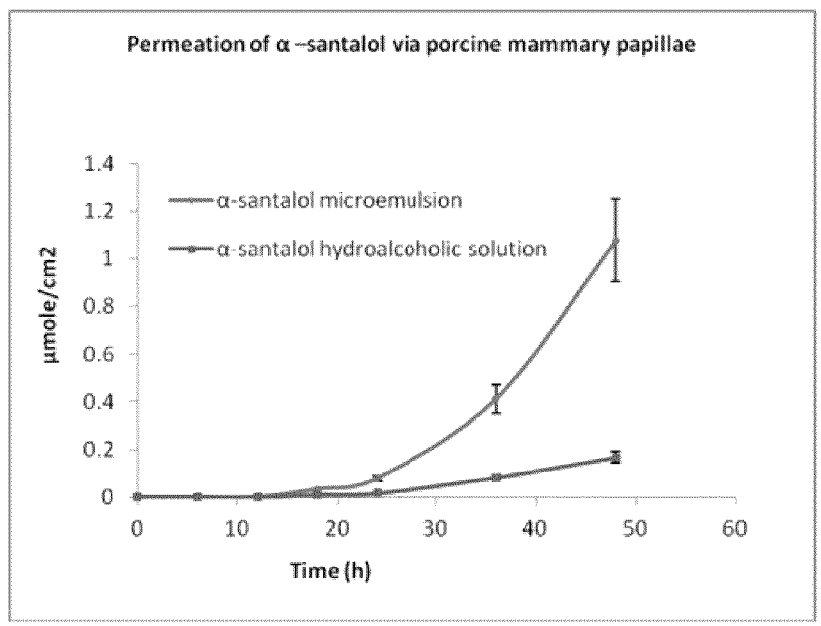
FIG. 52. Permeation of α-santalol via porcine mammary papillae. Each data point is represented as mean±SEM, n=3.

Porcine mammary papillae were thawed from the freezer and then keratin plug was removed from the surface of these tissues by gentle rubbing with an alcoholic cotton swabs. These tissues were washed and set in Franz diffusion cells and left for 12 hours for saturation with 1:1 ethanol:PBS in receptor and PBS in donor. After 12 hours, solution and microemulsion were placed in the donor (500 μl). Donor compartments were covered with parafilm. Samples from receptor (400 μl each) were withdrawn at 6, 12, 18, 24, 36 and 48 hours for GC-MS analysis. These samples were dried by nitrogen flush and then reconstituted in ethyl acetate for analysis. At the end of 24 hours, tissues were removed from diffusion cells and were thoroughly washed and blotted dried (this was repeated 3 times). After that tissues were weighed and cut into small pieces. Now α-santalol was extracted from these tissues using ethyl acetate (3 times). The samples were analyzed by GCMS. Results may be seen in FIG. 52 and Table 35.

Results:

TABLE 35

Parameters of α-santalol permeation and retention into porcine mammary papilla

| Mode | lag time (h) | Flux (μmole/ sq.cm/h) | cumulative amount permeated (μmole) | Drug permeation (% of applied dose) | Drug in tissue μmole/g tissue |
|---|---|---|---|---|---|
| Solution | 21.67 (0.41) | 0.006 (0.001) | 0.11 (0.01) | 0.12 (0.02) | 14.78 (2.78) |
| Microemulsion | 23.42 (0.09) | 0.042 (0.007) | 0.69 (0.11) | 0.15 (0.02) | 57.7 (3.41) |

Values in parentheses are SEM (n = 3)

Results and discussion: The study suggests that α-santalol was able to permeate across mammary papilla. It is important to note that the study was performed after removal of the keratin plug from the surface of the mammary papilla. Keratin plug removal pretreatment seems to enhancing permeation of α-santalol via porcine mammary papilla. From this study it is evident that microemulsion induces significantly higher permeation of α-santalol across mammary papilla than hydralcoholic solution. From the flux and cumulative amount of drug permeation values the increase is approximately 6-7 folds. Drug retention at the end of 48 h treatment is 4 fold higher in case of microemulsion than solution. Now if we look at the values of % of dose applied in donor chamber, it is not very different in case of microemulsion and solution. The reason for this could be, microemulsion has 25% v/v concentration of α-santalol while the solution has 5% v/v concentration. So, though the total amount of drug permeated is 6 folds higher in case of microemulsion, the % of the total applied does is similar.

Conclusion

Microemulsion with 25% v/v or α-santalol is significantly better in terms of permeation and retention of α-santalol via mammary papilla, than hydroalcoholic solution of 5% v/v α-santalol. Further studies with same concentration of α-santalol in these formulations need to be performed to prove the superiority of α-santalol microemulsion.

Experiment 27

Topical Transmammary Delivery of Tamoxifen with and without α-Santalol Via Porcine Mammary Papilla

TABLE 36

Experimental Design for Experiment 27.

| Experiment design | |
|---|---|
| Donor | 10 mg/ml TAM (400 μl) in 3:1 ethanol:water with 5% α-santalol spiked with 3H-estradiol |
| Receptor | 30:70 of ethanol 7.4 PBS with 0.05% w/v sodium azide |
| Control | 10 mg/ml TAM (400 μl) in 3:1 ethanol:water without 5% α-santalol spiked with 3H-estradiol |
| Tissue saturation | Tissue was set up and kept for 12 hours with water in donor and 30:70 ethanol 7.4 PBS in receptor |

Formulation:
Hydroalcoholic Solution with α-Santalol:

| | |
|---|---|
| Tamoxifen | 1% w/v |
| α-santalol | 5% v/v |
| 3:1 of ethanol:water | q.s. |

Hydroalcoholic Solution without α-Santalol:

| | |
|---|---|
| Tamoxifen | 1% w/v |
| 3:1 of ethanol:water | q.s. |

Experimental Procedure

Figure 53:
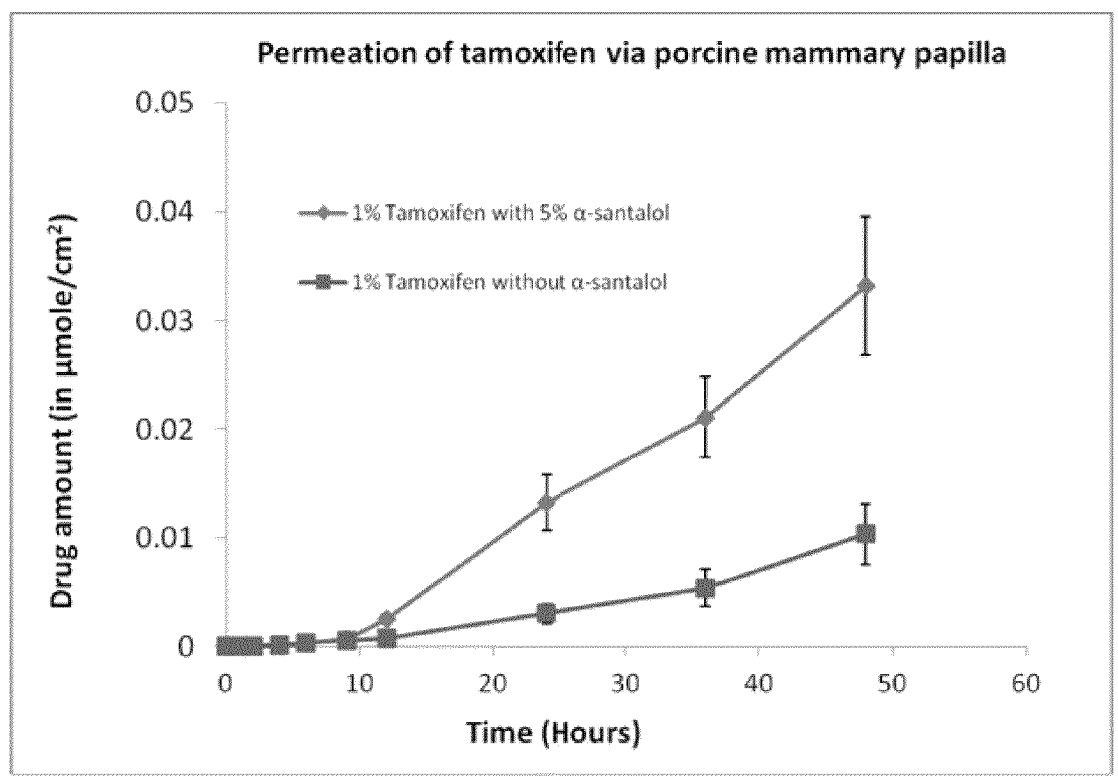
FIG. 53. Permeation of tamoxifen, with and without 5% α-santalol, via porcine mammary papilla. Each data point is represented as mean±SEM, n=3.

Mammary papilla tissues were set in FSD and kept for saturation for 12 hours. The drug solutions were spiked with 4 μl 3H TAM per 3 ml solution. 400 μl of the drug formulation was placed in the donor compartment. Three 200 μl each, samples of drug formulations were taken to determine DPM of donors. From the receptor, 200 μl samples were taken at every time point. After 48 hours, tissues were taken, washed, cut in four sections, weighed and solubilized using the tissue solubilizer. After 24 hours, DPM counts were measured from each section of the tissue using scintillation cocktail. Results may be seen in FIG. 53 and Table 37.

Results

TABLE 37

Drug permeation and retention parameters

| Mode | lag time (hr) | Flux (μmole/sq.cm/hr) | cumulative amt. permeated (μmole) | % of total applied dose permeated across the tissue | Skin retention (umole/gram tissue) | % of total applied dose retention in the tissue |
|---|---|---|---|---|---|---|
| 1% TAM in 3:1 EoH:H2O with 5% santalol | 8.84 (0.29) | 0.00083 (0.00002) | 0.06 (0.011) | 0.54 (0.10) | 8.57 (1.92) | 41.03 (6.75) |
| 1% TAM in 3:1 EoH:H2O without santalol | 13.67 (0.96) | 0.00032 (0.00005) | 0.018 (0.005) | 0.17 (0.04) | 1.71 (0.43) | 9.62 (1.52) |

Values in parentheses are SEM

Discussion

From the Tissue permeation data it is evident that tamoxifen can permeate across mammary papilla. When given in combination with α-santalol, permeation of tamoxifen is significantly higher with lesser lag time in comparison to the control group. This indicates the role of α-santalol in enhancing permeation of tamoxifen. Previous studies have shown that α-santalol fluidizes the lipids of the stratum corneum which is considered to be the main mechanism for its permeation enhancer properties. Now, being a highly lipophilic molecule (log P ~7), tamoxifen is not expected to go across mammary papilla. This difficult to happen phenomenon is happening here probably due to the unique structure of mammary papilla which may carry the drug downwards from the surface through the ducts. Here α-santalol is showing significantly higher permeation (~3-4 folds) of tamoxifen which could be due to higher penetration of the drug into the tissue. This drug can be transported downwards either via the connective tissue or via the ducts, if the drug enters into the ducts either from the surface or from the connective tissue by crossing the epithelial layer. Drug retention studies show that approximately 40% of the applied dose is retained by the tissue. Drug retention is much lower when drug was treated without α-santalol.

Conclusion

Altogether, the results of this study suggest that tamoxifen can be delivered via mammary papilla. Penetration and transport of tamoxifen via mammary papilla was substantially enhanced when given in combination with 5% α-santalol. As both, tamoxifen and α-santalol, have proven efficacy against breast cancer, this combination has great potential for breast cancer therapy when delivered via transmammary route.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

We claim herein:

1. A composition for the treatment of a condition affecting breast tissue comprising an alcoholic component, a therapeutic agent, and an effective carrier, the composition being adapted for transdermal permeation through the mammary papilla, areola, or a combination thereof, and into underlying breast tissue, wherein said carrier is an extract of sandalwood oil wherein said extract comprises α-santalol, and wherein said therapeutic agent is selected from 5-fluorouracil, cyclophosphamide, tamoxifen, adriamycin, danazol, progesterone, doxorubicin, paclitaxel, cisplatin, or docetaxel.

2. The composition of claim 1, wherein the composition is a microemulsion.

3. The composition of claim 1, wherein the composition is a hydroalcoholic solution.

4. The composition of claim 1, wherein the composition comprises at least 5% α-santalol (v/v).

5. The composition of claim 1, wherein the composition comprises between about 5% to about 25% α-santalol (v/v).

6. A composition comprising α-santalol, an alcohol, optionally a surfactant, and a compound selected from the group consisting of 5-fluorouracil, cyclophosphamide, tamoxifen, adriamycin, danazol, progesterone, doxorubicin, paclitaxel, cisplatin, docetaxel, nitrosoureas, camptothecins, lipophilic statins, retinoids, and daunomycin.

7. A method of treating a subject with breast cancer comprising: (a) applying sufficient alcohol to the outer surface of mammary papillae tissue of the subject to remove the keratin plug therein; and (b) administering the composition of claim 6 to the alcohol treated mammary papillae at a sufficient does to produce a therapeutic effect.

8. The method of claim 7, wherein said surface is dry prior to the administering step.

9. The method of claim 7, wherein the composition comprises α-santalol, an alcohol, a surfactant and tamoxifen in the form of a microemulsion.

10. The method of claim 7, wherein the composition comprises between about 5% to about 25% α-santalol (v/v).

* * * * *